United States Patent [19]
Tsuruoka et al.

[11] Patent Number: 5,331,551
[45] Date of Patent: Jul. 19, 1994

[54] ENDOSCOPE IMAGE RECORDING SYSTEM FOR COMPRESSING AND RECORDING ENDOSCOPE IMAGE DATA

[75] Inventors: Takao Tsuruoka, Hachioji; Keiichi Hiyama, Akishima; Kazunari Nakamura, Hachioji; Yutaka Konomura, Tachikawa; Masahide Kanno; Shinichiro Hattori, both of Hachioji, all of Japan

[73] Assignee: Olympus Optical Co., Ltd., Tokyo, Japan

[21] Appl. No.: 558,551

[22] Filed: Jul. 27, 1990

[30] Foreign Application Priority Data

| Oct. 2, 1989 | [JP] | Japan | 1-258050 |
| Oct. 2, 1989 | [JP] | Japan | 1-258051 |
| Oct. 2, 1989 | [JP] | Japan | 1-258052 |
| Oct. 4, 1989 | [JP] | Japan | 1-260725 |
| Oct. 5, 1989 | [JP] | Japan | 1-260842 |

[51] Int. Cl.⁵ .......................... A61B 1/04; H04N 7/18
[52] U.S. Cl. .................... 364/413.13; 348/71
[58] Field of Search ............ 364/413.01, 413.02, 364/413.13, 413.19, 413.22; 358/43, 98, 128; 128/6

[56] References Cited

U.S. PATENT DOCUMENTS

| 4,819,077 | 4/1989 | Kikuchi et al. | 358/98 |
| 4,845,553 | 7/1989 | Konomura et al. | 358/98 |
| 4,914,512 | 4/1990 | Sekiguchi | 358/98 |
| 4,920,413 | 4/1990 | Nakamura et al. | 358/98 |
| 4,926,247 | 5/1990 | Nagasaki et al. | 358/43 |
| 4,928,172 | 5/1990 | Uehara et al. | 358/98 |
| 4,961,110 | 10/1990 | Nakamura | 358/98 |
| 5,001,556 | 3/1991 | Nakamura et al. | 358/98 |
| 5,031,036 | 7/1991 | Kikuchi et al. | 358/98 |
| 5,081,524 | 1/1992 | Tsuruoka et al. | 358/32 |

Primary Examiner—Roy N. Envall, Jr.
Assistant Examiner—A. Bodendorf
Attorney, Agent, or Firm—Armstrong, Westerman, Hattori, McLeland & Naughton

[57] ABSTRACT

An endoscope image signal photoelectrically converted by an image sensing device in an endoscope is compressed by an image compressing apparatus and then recorded in a recording apparatus, whereby the number of image frames recordable in the recording apparatus can be increased. Also, the image compression is effectively performed, for example, by changing a compression ratio dependent on a quantity of respective image information contained in plural components of the endoscope image signal, whereby a quantity of information actually recorded can be reduced.

36 Claims, 34 Drawing Sheets

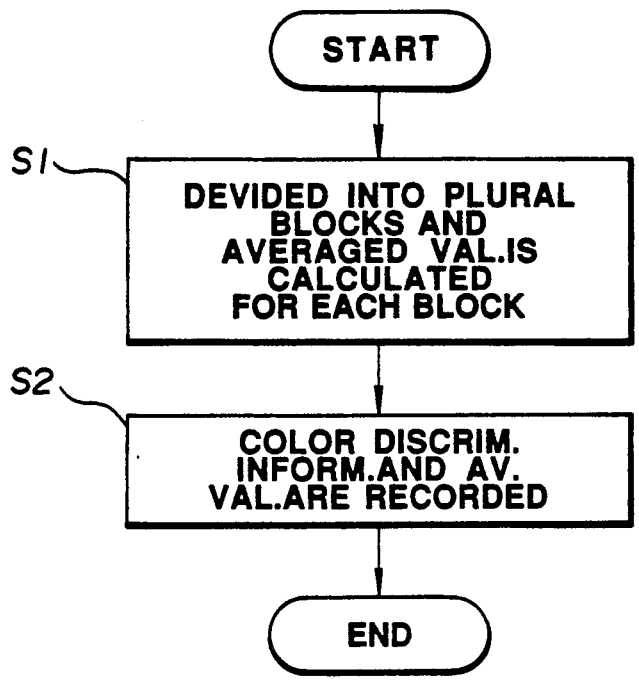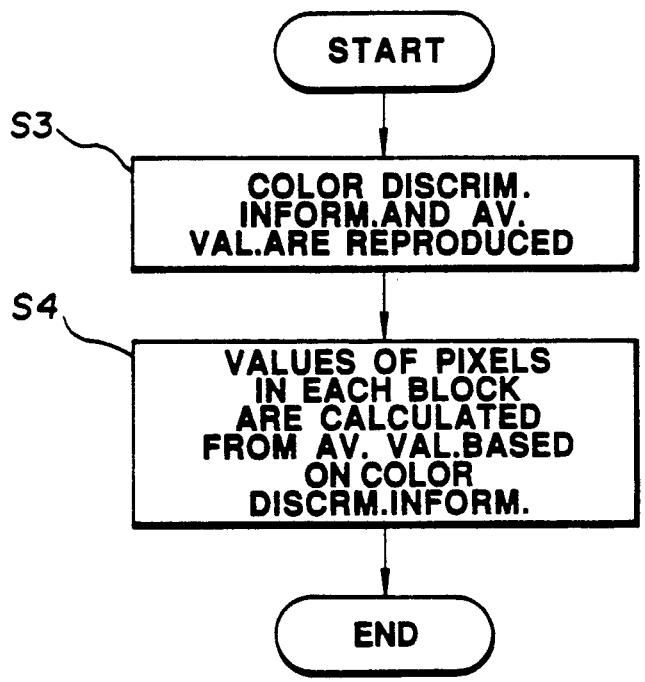

FIG. 7
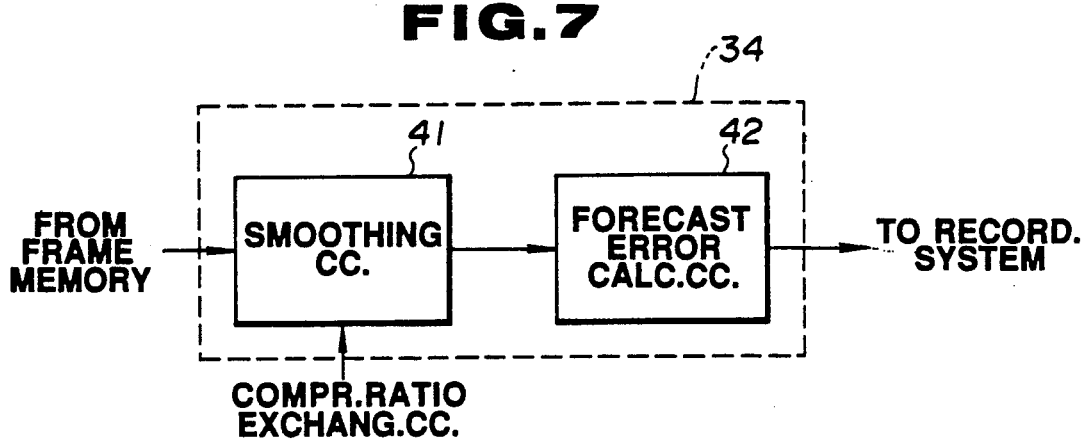
FIG. 8
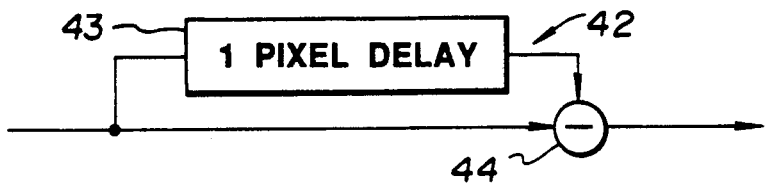
FIG. 9
$x(i-1,j-1)$    $x(i,j-1)$    $(xi+1,j-1)$
$x(i-1,j)$    $x(i,j)$
FIG. 10
| k/8 | k/8 | k/8 |
|-----|-----|-----|
| k/8 | 1-k | k/8 |
| k/8 | k/8 | k/8 |

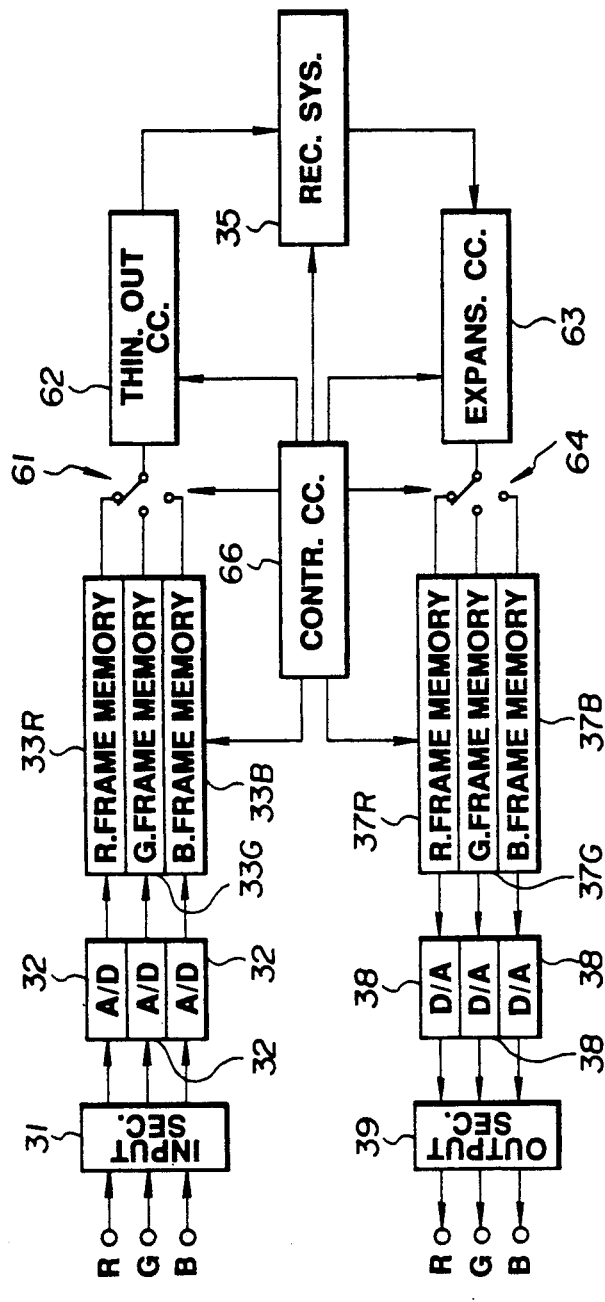
FIG.15
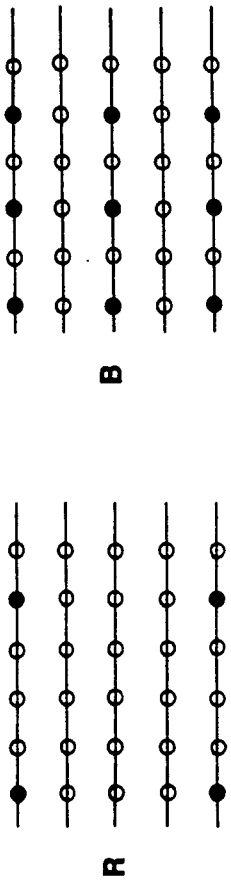
FIG.16b
FIG.16a

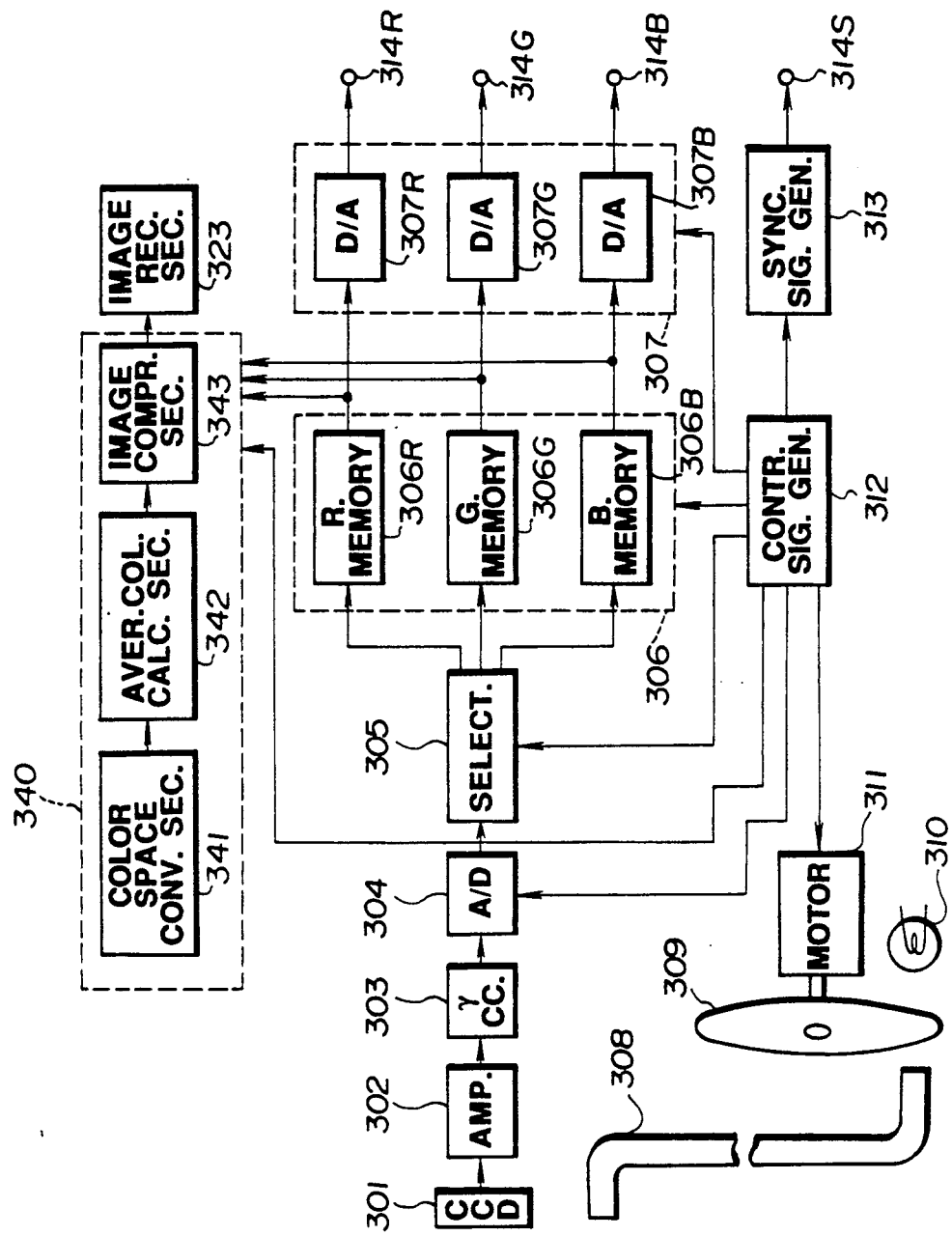

ENDOSCOPE IMAGE RECORDING SYSTEM FOR COMPRESSING AND RECORDING ENDOSCOPE IMAGE DATA

BACKGROUND OF THE INVENTION

Field of the Invention and Description of the Relevant Art

The present invention relates to an endoscope image recording system for compressing and recording endoscope image data.

Recently, there have widely been used endoscopes of which elongate insert sections are inserted into body cavities to observe organs or the like related with the body cavities, and which permit a variety of medical treatment using appliances inserted through appliance channels as required.

There have also been practiced electronic endoscopes in which solid imaging devices such as CCD's are provided at the respective distal ends of the endoscope insert sections.

In some cases, endoscope images picked up by such electronic endoscopes or TV cameras connected to the eyepiece sections of fiberscopes are not only observed by TV monitors, but also recorded on image recording apparatus for later diagnosis or analysis. When recording endoscope images like such cases, there arises a problem of requiring a memory unit with large capacity because the image data contain a large quantity of data. Another problem is in that when transmitting the image, the transmission speed becomes slow.

OBJECTS AND SUMMARY OF THE INVENTION

An object of the present invention is to provide an endoscope image recording system which can increase the number of image frames recordable.

Another object of the present invention is to provide en endoscope image recording system which can increase the number of image frames with little reduction in the image quality.

Still another object of the present invention is to provide an endoscope image recording system which can perform image compression dependent on a quantity of image information for effective recording.

An endoscope image recording system of the present invention includes compression means for compressing an endoscope image signal from image sensing means of an endoscope, and digital recording means for digitally recording a compressed image data compressed by the compression means, thereby enabling to increase the number of image frames recordable in the recording means.

Also, in the present system, the image compression is effectively performed dependent on a quantity of information of the endoscope image signal from the image sensing means, whereby a quantity of image data actually recorded in the recording means is reduced to relatively increase a quantity of image data virtually recordable in the recording means.

BRIEF DESCRIPTION OF THE DRAWINGS

FIGS. 1 through 6 are concerned with a first embodiment of the present invention in which:

FIG. 1 is a block diagram showing the configuration of an image recording apparatus;

FIG. 2 is an explanatory view showing the entire of an endoscope image recording system;

FIG. 3 is a block diagram showing the configuration of an observation apparatus;

FIG. 4 is a flowchart showing a recording operation of the image recording apparatus;

FIG. 5 is a flowchart showing a reproducing operation of the image recording apparatus.

FIGS. 7 through 10 are concerned with a second embodiment of the present invention in which:

FIG. 7 is a block diagram showing the configuration of the compression circuit;

FIG. 8 is a block diagram showing the configuration of a forecast error calculating circuit;

FIG. 9 is a representation for explaining the manner of calculating a forecast error; and FIG. 10 is an explanatory view of a smoothing filter.

FIGS. 11 through 14 are concerned with a third embodiment of the present invention in which:

FIG. 11 is a block diagram showing the configuration of an image recording apparatus;

FIG. 12 is a block diagram showing the configuration of a forecast error calculating circuit;

FIG. 13 is a block diagram showing the configuration of a band exchanging circuit; and FIG. 14 is a graphic representation showing bands passing through respective LPF's.

FIGS. 15 and 16 are concerned with a fourth embodiment of the present invention in which:

FIG. 15 is a block diagram showing the configuration of an image recording apparatus; and FIGS. 16a and 16b are an explanatory view for explaining a thinning-out operation.

FIGS. 17 through 19 are concerned with a fifth embodiment of the present invention in which:

FIG. 17 is a flowchart showing a recording operation of an image recording apparatus;

FIG. 18 is a flowchart showing a reproducing operation of the image recording apparatus.

FIGS. 21 through 23 are concerned with a seventh embodiment of the present invention in which:

FIG. 21 is an explanatory view showing the entire configuration of an endoscope image filing system;

FIG. 22 is a block diagram for explaining the internal configuration of an endoscope apparatus; and FIG. 23 is a block diagram showing the configuration of a scope image data compressing apparatus.

FIGS. 25 and 26 are concerned with a ninth embodiment of the present invention in which:

FIG. 25 is a view showing the entire configuration of the ninth embodiment; and

FIG. 26 is a block diagram showing the configuration of a scope image data compressing apparatus.

FIGS. 28 through 31 are concerned with an eleventh embodiment of the present invention in which:

FIG. 28 is a view showing the entire configuration of the eleventh embodiment;

FIG. 29 is a block diagram showing the configuration of a scope image data compressing apparatus;

FIGS. 32 through 35 are concerned with a twelfth embodiment of the present invention in which:

FIG. 32 is a view showing the entire configuration of the twelfth embodiment;

FIG. 33 is a block diagram showing the configuration of a scope image data compressing apparatus.

FIGS. 36 and 37 are concerned with a thirteenth embodiment of the present invention in which:

FIG. 36 is a view showing the entire configuration of the thirteenth embodiment; and FIG. 37 is a block diagram showing the configuration of a scope image data compressing apparatus.

FIGS. 38 through 43 are concerned with a fourteenth embodiment of the present invention in which:

FIG. 38 is a view showing the entire configuration of the fourteenth embodiment;

FIG. 39 is a block diagram showing the configuration of an image compressing apparatus;

FIG. 40 is a block diagram showing the configuration of a video processor;

FIG. 41 is a graphic representation showing one example of distribution of the endoscope image data over an RGB space;

FIG. 42 is a graphic representation showing one example of distribution of the endoscope image data over a uniform color space.

FIGS. 44 and 45 are concerned with a fifteenth embodiment of the present invention in which:

FIG. 44 is a block diagram showing the configuration of an image compressing apparatus in the fifteenth embodiment.

FIGS. 46 and 47 are concerned with a sixteenth embodiment of the present invention in which:

FIG. 46 is a view showing the entire configuration of the sixteenth embodiment; and FIG. 47 is a block diagram showing the internal configuration of FIG. 46.

DETAILED DESCRIPTION OF PREFERRED EMBODIMENTS

Figure 2:
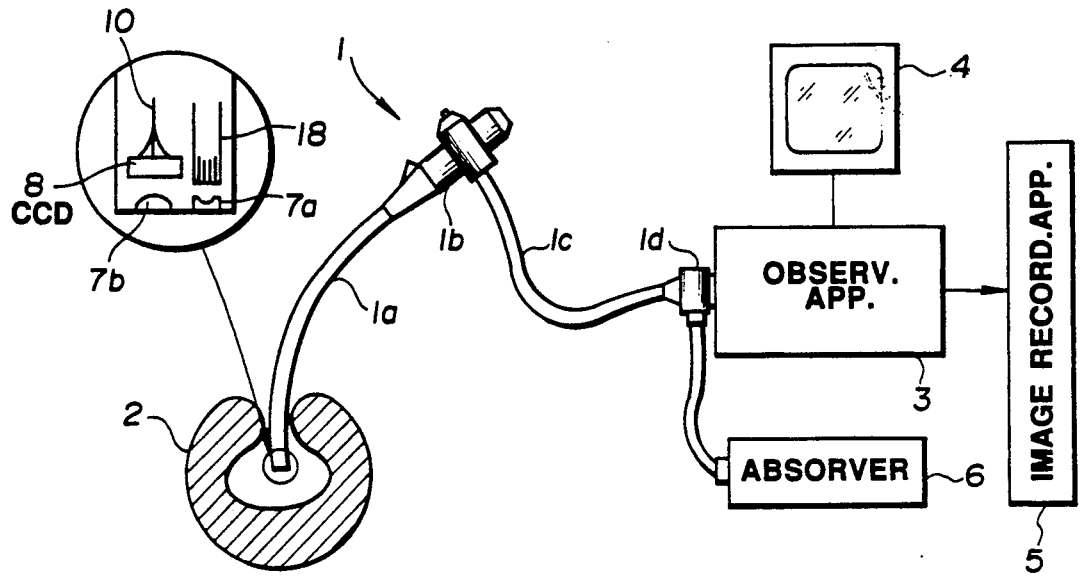

An endoscope image recording system of a first embodiment comprises, as shown in FIG. 2, an electronic endoscope 1; an observation apparatus 3 and an absorber 6 to both of which the electronic endoscope 1 is connected; and a monitor 4 and an image recording apparatus 5 which are connected to the observation apparatus 3.

The electronic endoscope 1 has an elongate insert section 1a which is flexible, for example, and inserted into a living body 2, an operating section 1b having a larger diameter and continuously provided at the rear end of the insert section 1a, and a universal cord 1c extended from the operating section 1b. Provided at the rear end of the universal cord 1c is a connector 1d which is connected to the observation apparatus (video processor) 3.

There are formed an illumination window and an observation window at the distal end of the insert section 1a of the electronic endoscope 1. A light directing lens 7a is fitted inside the illumination window, and a light guide 18 is provided behind the light directing lens 7a in facing relation thereto. The light guide 18 is extended through the insert section 1a, the operating section 1b and the universal cord 1c for connection with the connector 1d. An objective lens system 7b is provided inside the observation window, and a solid imaging device 8, e.g., a CCD, is disposed at a focus position of the objective lens system 7b. An output signal of the CCD 8 is applied to the observation apparatus 3 through a bundle of signal lines 10 which are extended through the insert section 1a, the operating section 1b and the universal cord 1c for connection with the connector 1d.

Figure 3:
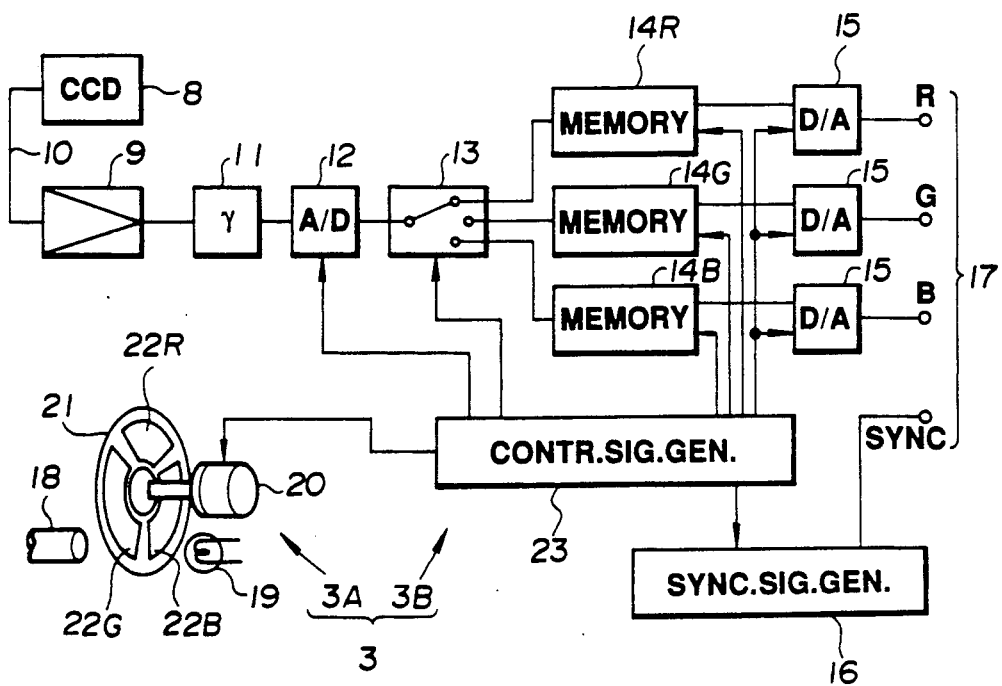

The observation apparatus 3 is constituted as shown in FIG. 3.

The observation apparatus 3 comprises a light source section 3A for supplying a beam of illumination light to the light guide 18, and a signal processing section 3B for processing a signal output from the CCD 8. The light source section 3A includes a lamp 19 for emitting a beam of white light, and a rotating filter 21 provided between the lamp 19 and the incident end of the light guide 18 and driven by a motor 20 to rotate about its axis. The rotating filter 21 has three filters 22R, 22G, 22B arranged in the circumferential direction with equal angular distances and capable of passing beams of lights corresponding to wavelength regions of red (R), green (G) and blue (B) therethrough, respectively, so that the filters 22R, 22G, 22B successively enter a path of the illumination light upon rotation of the motor 20. Then, the three beams of light time-serially separated by the rotating filter 21 corresponding to the respective wavelength regions of R, G, B are emitted from the distal end of the insert section 1a of the electronic endoscope 1 through the light guide 18 and the light directing lens 7a.

Further, the signal processing section 3B in the observation apparatus 3 has an amplifier 9 which amplifies the output signal of the CCD 8 to a voltage level within a predetermined range, followed by $\gamma$ correction in a $\gamma$ correction circuit 11. The signal having been subjected to the $\gamma$ correction is converted to a digital signal by an A/D converter 12, and then selectively input through a selector switch 13 to memories 14R, 14G, 14B corresponding to R, G, B so that R, G and B images are stored in the memories 14R, 14G, 14B, respectively. The data in the memories 14R, 14G, 14B are read out at the timing of a standard TV signal simultaneously, and converted to analog signals by respective D/A converters 15, 15, 15. These analog R, G, B image signals are delivered from RGB signal output terminals 17 with a synchronizing signal SYNC from a synchronizing signal generator 16 for being applied to a monitor 4, an image recording apparatus 5 and others. The motor 20, the A/D converter 12, the selector switch 13, the memories 14R, 14G, 14B, the D/A converters 15, and the synchronizing signal generator 16 are all controlled by a control signal generator 23.

Figure 1:
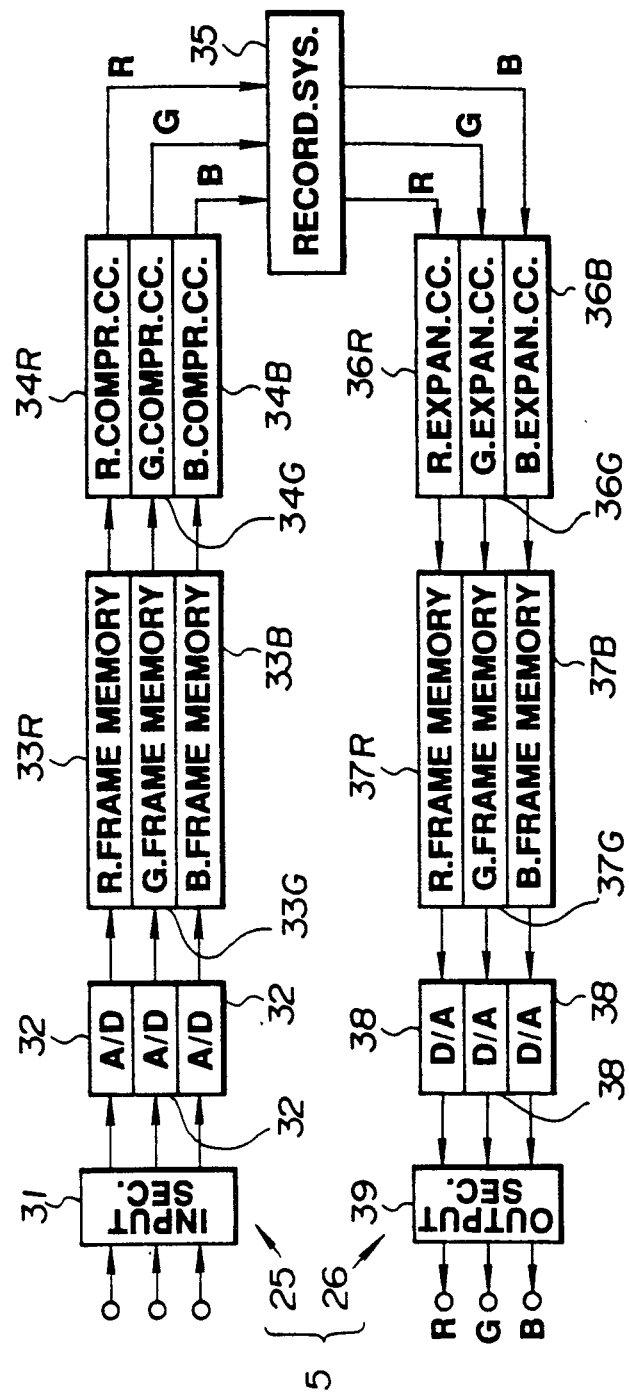

The image recording apparatus 5 inclusive of a scope image data compressing apparatus will be described below by referring to FIG. 1.

The R, G, B image signals output from the observation apparatus 3 are applied through an input section 31 of a compressed image data generator 25, i.e., a generator for creating image data to be recorded actually, for being converted to digital signals by A/D converters 32, 32, 32 and then temporarily stored in an red (R) frame memory 33R, a green (G) frame memory 33G and a blue (B) frame memory 33B, respectively. The R, G, B image signals read out of the frame memories 33R, 33G, 33B are compressed at different compression ratios by an R compression circuit 34R, a G compression circuit 34G and a B compression circuit 34B to create compressed image data, respectively, and are then recorded in a recording system 35 such as an optical disk or magnetic disk.

In reproducing the image data, the compressed R, G, B image data are read out of the recording system 35 and separately expanded by an R expansion circuit 36R, a G expansion circuit 36G and a B expansion circuit 36B for restoring the data, respectively, the circuits 36R, 36G and 36B constituting a part of an image signal restoring section 26 which creates signals approximate to the image signals prior to the compression. The respective restored R, G, B image data are temporarily stored in an R frame memory 37R, a G frame memory 37G and a B frame memory 37B. Then, R, G, B image signals are read out of the frame memories 37R, 37G, 37B in synchronism with the TV signal and converted to analog image signals by D/A converters 38, 38, 38, respectively. Afterward, the analog image signals are delivered from an output section 39 to be displayed on the monitor 4 or any other display, for example.

Operations of the compression circuits 34R, 34G, 34B and the expansion circuits 36R, 36G, 36B will be described below by referring to FIGS. 4 through 6.

In the compression circuit 34 (representative of 34R, 34G, 34B), as shown in FIG. 4, the entire input image is divided into plural blocks each comprising the predetermined number of pixels, and an average value of respective density values in each block is calculated in a step S1. The aforesaid average value is then recorded in the recording system 35 along with color discriminating information in a step S2. In this embodiment, the number of pixels in one block is set to be 9 for an R image, 2 for a G image and 4 for a B image. Accordingly, the image data are recorded after being compressed to about 1/9 for the R image, about ½ for the G image, and about ¼ for the B image.

Meanwhile, in the expansion circuit 36 (representative of 36R, 36G, 36B), as shown in FIG. 5, the color discriminating information and the average value of each block are reproduced in a step S3. Then, pixels constituting one block are restored based on the color discriminating information in a step S4, by using the aforesaid average value as density values of the respective pixels in the block.

Figure 6A:
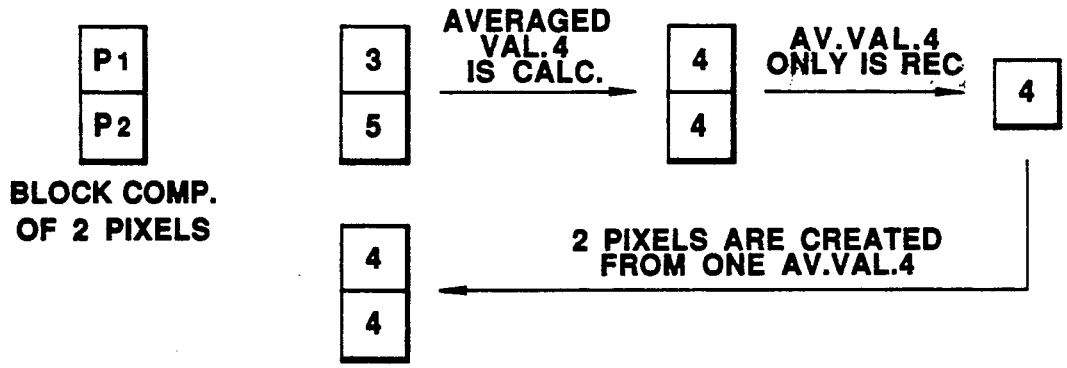
FIGS. 6a, 6b, and 6c are an explanatory view for explaining a compressing operation of a compression circuit.
Figure 6B:
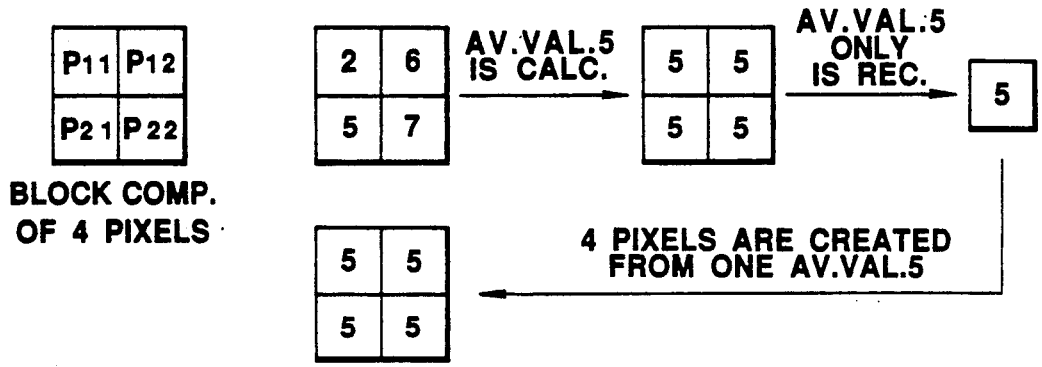
Figure 6C:
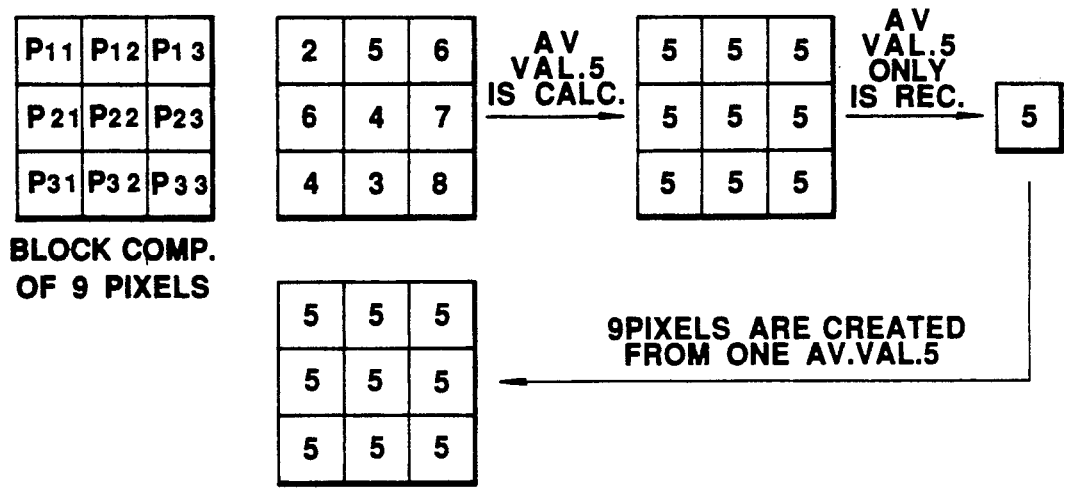

FIG. 6 shows one example of the compressing and expanding operation with concrete density values put in blocks. FIG. 6a is related to the G image, FIG. 6b is related to the B image, and FIG. 6c is related to the G image, respectively. For the G image, as shown in FIG. 6a, the entire input image is divided into plural blocks each comprising two pixels $P_1$, $P_2$. By way of example, an average value (4) of respective density values (3, 5) of the pixels in one block is calculated and then recorded in the recording system 35. In reproducing, density values (4, 4) of two pixels are created from one average value (4) reproduced out of the recording system 35. For the B image, as shown in FIG. 6b, one block comprises four pixels $P_{11}$, $P_{12}$, $P_{21}$, $P_{22}$. Likewise, an average value (5) of respective density values (2, 6, 5, 7) of the pixels in one block is calculated and then recorded in the recording system 35. In reproducing, density values (5, 5, 5, 5) of four pixels are created from thee average value (5). For the R image, as shown in FIG. 6c, one block comprises nine pixels $P_{11}$–$P_{13}$, $P_{21}$–$P_{23}$, $P_{31}$–$P_{33}$. Likewise, an average value (5) of respective density values (2, 5, 6, 6, 4, 7, 4, 3, 8) of the pixels in one block is calculated and then recorded in the recording system 35. In reproducing, density values of nine pixels are created from the average value (5).

In the case of the compressing and expanding operation as mentioned above, with the number of pixels in one block increasing, the compression ratio becomes higher and the resolution in reproducing is deteriorated. The relationship of the number of pixels in one block, the compression ratio and the resolution in reproducing among the R, G, B images is given by Table 1 below.

TABLE 1

| Image | R Image | B Image | G Image |
| --- | --- | --- | --- |
| Number of pixels in one block | 9 | 4 | 2 |
| Compression ratio | high | med. | low |
| Resolution in reproducing | poor | med. | good |

As will be seen from the foregoing, out of the three R, G, B images jointly constituting an endoscope image, the R image corresponding to an image component of the longest wavelength is data-compressed at a higher compression ratio than the other G, B images in this embodiment. Generally, an R image among endoscope images has the relatively flat form with a less high-frequency (spatial frequency) component. Therefore, the R image does not so contribute to display of the color and shape of the morbid or diseased location which is important for diagnosis, while the G and B images rather contain more important information. Accordingly, even if the compression ratio is increased and the resolution in reproducing is lower to some extent for the R image, the diagnosis will not be affected significantly.

Further, because the G image has the most important information for diagnosis, the compression ratio of the G image is retained to be low in this embodiment by taking great account of the resolution in reproducing.

With this embodiment, as described above, the endoscope image data can be compressed by making use of features of the endoscope image at a high compression ratio and with the simple configuration in a manner such that diagnosis will not be affected by a reduction in the image quality in reproducing.

In other words, this embodiment has a merit of increasing the number of image frames recordable in the recording system 35 as recording means, while suppressing a reduction in the image quality in reproducing.

Next, a second embodiment will be described.

This embodiment is different from the first embodiment in a compression circuit 34 and an expansion circuit 36 which are provided to process the R, G, B image signals.

The compression circuit 34 of this embodiment comprises a smoothing circuit 41 and a forecast error calculating circuit 42, as shown in FIG. 7. The image signals from the frame memories 33R, 33G, 33B are smoothed by the smoothing circuit 41 and forecast-coded by the forecast error calculating circuit 42, following which the coded signals are recorded in the recording system 35.

The smoothing circuit 41 is designed to smooth the image signals by a two-dimensional filter comprising 3×3 (pixels) as shown in FIG. 10. This filter sets, as a density value of each pixel after smoothing, the sum of the product resulted from multiplying a density value of that pixel by $(1-k)$ and the products resulted from multiplying respective density values of eight pixels surrounding that respective density values of eight pixels surrounding that pixel by $(k/8)$. Incidentally, k $(0<k<1)$ is a smoothing factor. A greater value of k implies a greater smoothing effect, and a smaller value of k implies a smaller smoothing effect. The value of the smoothing factor k is changed over by a compression ratio exchanging circuit which is able to vary the value of k with dip switches, for example. By optionally setting the value of the smoothing factor k, the band of spatial frequency after smoothing can be decided. Thus, as the smoothing effect increases with the greater value of k, the high-frequency component of the image is degraded.

The forecast error calculating circuit 42 is designed, as shown in FIG. 8, such that the input data is delayed one pixel by a one-pixel delay line 43, and the delayed data is subtracted from the original next input data by a subtracter 44 to determine the difference between the current input data and the preceding input data of one pixel before. As illustrated in FIG. 9, assuming the density value of a pixel (i, j) to be x(i, j), a forecast error signal $\Delta x(i, j)$ output from the precast error calculating circuit 42 is expressed by:

$$\Delta x(i, j) = x(i, j) - x(i-1, j).$$

Since this forecast error signal has a value smaller than the input data, a quantity of data to be recorded in the recording system 35 is reduced correspondingly.

On the other hand, the expansion circuit 36 restores the original data by adding a forecast signal, i.e., the preceding data of one pixel before, to the forecast error signal reproduced from the recording system 35. Unlike the first embodiment, the expansion circuit 36 is identical in the circuit configuration and operation for all of R, G, B in this embodiment.

Here, when the smoothing factor k for the smoothing circuit 41 is set larger, the high-frequency component of the image is deteriorated, but the forecast error signal has a relatively small value as a whole because of the greater smoothing effect, with the result that a quantity of data to be recorded is reduced. In short, the compression ratio is high. conversely, when k is set smaller to reduce the smoothing effect, the high-frequency component of the image is not deteriorated and the forecast error signal has a relatively large value as s whole, but with the result that a quantity of data to be recorded is also reduced. In short, the compression ratio is low. In this way, by optionally setting the smoothing factor k for the smoothing circuit 41, it is possible to set the compression ratio on demand.

In this embodiment, the smoothing factors k for the smoothing circuits 41 in the compression circuits 34 are set for the respective image signals such that the compression ratios are in the order of R, B, G from the highest, as with the first embodiment. The relationship of the smoothing factor k, the compression ratio and the resolution in reproducing among the R, G, B images is given by Table 2 below.

TABLE 2

| Image | R Image | B Image | G Image |
|---|---|---|---|
| Smoothing factor k | large | med. | small |
| Compression ratio | high | med. | low |
| Resolution in reproducing | poor | med. | good |

In this embodiment, as described above, the resolution is lowered and the compression ratio is increased for the R image which raises no problem in viewpoint of diagnosis even with the lowered resolution, while keeping high the resolution of the G image which is important for diagnosis, like the first embodiment.

Other configuration, operation and advantageous effect are similar to those of the first embodiment.

Figure 11:
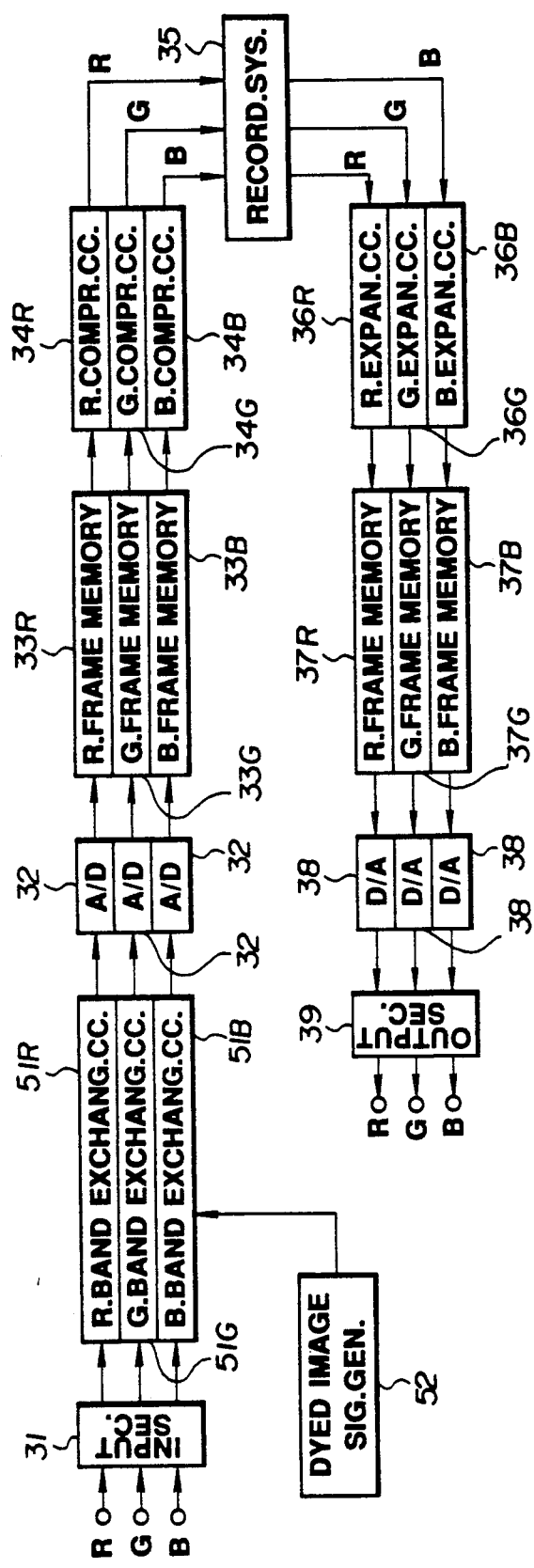

In a third embodiment, as shown in FIG. 11, an R band exchanging circuit 51R, a G band exchanging circuit 51G and a B band exchanging circuit 51B are provided between the input section 31 and the A/D converters 32, 32, 32 in the first embodiment.

Figure 12:
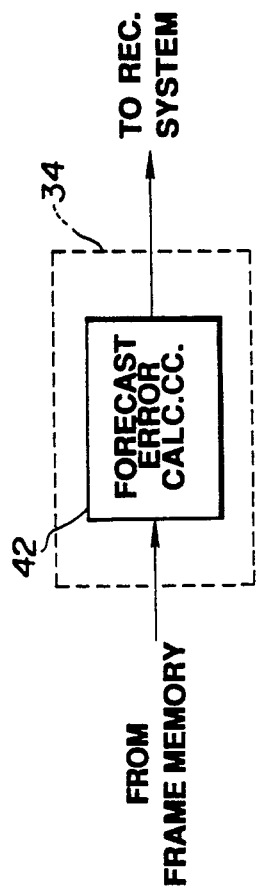

Further, as shown in FIG. 12, a compression circuit 34 in this embodiment has a forecast error calculating circuit 42 similar to that in the second embodiment. In this embodiment, however, the compression circuit 34 is identical in the circuit configuration and operation for all of R, G, B, unlike the second embodiment. In addition, an expansion circuit 36 restores the original data by adding a forecast signal, i.e., the preceding data of one pixel before, to the forecast error signal reproduced from the recording system 35, as with the second embodiment. The expansion circuit 36 is also identical in the circuit configuration and operation for all of R, G, B.

Figure 13:
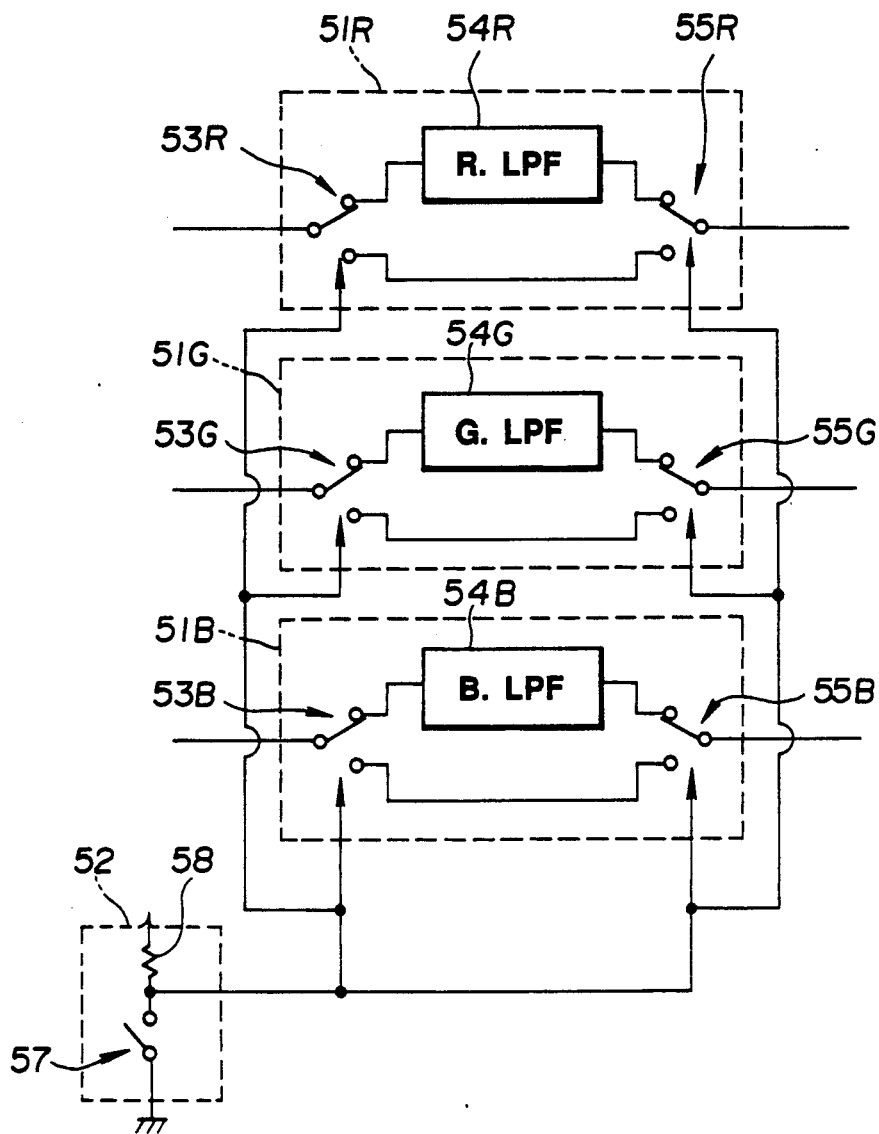

The band exchanging circuits 51R, 51G, 51B are constituted as shown in FIG. 13.

Figure 14:
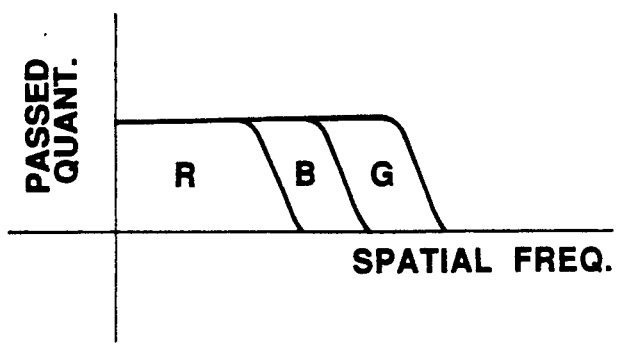

Input terminals of the band exchanging circuits 51R, 51G, 51B serve also as input terminals of selector switches 53R, 53G, 53B each being of 1-input, 2-output type, respectively. One output terminals of the selector switches 53R, 53G, 53B are connected to input terminals of an red (R) low-pass filter (hereinafter abbreviated to as LPF) 54R, a green (G) LPF 54G and a blue (B) LPF 54B, respectively. Output terminals of the LPF's 54R, 54G, 54B are connected to one input terminals of selector switches 55R, 55G, 55B each being of the 2-input, 1-output type, respectively. Further, the other output terminals of the selector switches 53R, 53G, 53B are connected to the other input terminals of the selector switches 55R, 55G, 55B, respectively. Outputs of the selector switches 55R, 55G, 55B then serve as outputs of the band exchanging circuits 51R, 51G, 51B. The respective frequency bands passing through the LPF's 54R, 54G, 54B are set as shown in FIG. 14. As will be seen, the R LPF 54R has a characteristic to remove the high-frequency component, the G LPF 54G has a characteristic to hardly remove the high-frequency component, and the B LPF 54B has an intermediate characteristic between the above twos.

The selector switches 53R, 53G, 53B and the selector switches 55R, 55G, 55B are both changed over by a signal from a dyed image signal generator 52. The dyed image signal generator 52 has a switch 57, to one terminal of which a source voltage is applied through a resistor 58 and the other terminal of which is grounded. The voltage being applied to one terminal of the switch 57 causes the selector switches 53R, 53G, 53B and the selector switches 55R, 55G, 55B to change over.

Operation of this embodiment will now be described.

When recording a normal image, the switch 57 of the dyed image signal generator 52 is turned off. Upon receiving this turning-off signal, the selector switches 53R, 53G, 53B and the selector switches 55R, 55G, 55B are both changed over to select the circuit paths including the LPF's 54R, 54G, 54B. This allows the R, G, B image signals to pass through the LPF's 54R, 54G, 54B, respectively. As to the R image signal, therefore, the high-frequency component is removed away and a quantity of data in the forecast error signal produced by the compression circuit 34R is considerably reduced. As to the B image signal, the high-frequency component still higher than that removed away for the R image signal is removed away, resulting in that a quantity of data in the forecast error signal is slightly reduced. As to the G image signal, since the high-frequency component is hardly removed away, a quantity of data in the forecast error signal is large, but the resolution is not deteriorated.

While the passing bands of the R, G, B signals are limited by the respective smoothing circuits 41 of the compression circuits 34R, 34G, 34B in a digital manner in the second embodiment, they are limited by the respective LPF's 54R, 54G, 54B of the band exchanging circuits 51R, 51G, 51B in an analog manner in this embodiment.

Then, when recording a dyed image, the switch 57 of the dyed image signal generator 52 is turned on. Upon receiving this turning-on signal, the selector switches 53R, 53G, 53B and the selector switches 55R, 55G, 55B are both changed over to select the circuit paths bypassing the LPF's 54R, 54G, 54B. Therefore, the R, G, B image signals are all directly output without passing through the respective LPF's 54R, 54G, 54B, and hence are not subjected to a band limitation. As a result, the compression ratio in the compression circuit 34 for the dyed image becomes smaller than that for the dyed image.

The reason why the image signals are not subjected to a band limitation in the case of the dyed image is as follows.

For the normal image, each of the R, G, B image signals, particularly the R image signal, has the relatively small high-frequency component and hence there occurs substantially no appreciable difference between the reproduced image and the original image even when subjected to the band limitation. On the contrary, detailed shapes appear clearly and distinctly in the dyed image. Therefore, the band limitation results in an obviously discernable reduction in the image quality as compared with the original image.

With this embodiment, as described above, the respective images can be exchanged in the resolution and compression ratio dependent on their characteristics.

Other configuration, operation and advantageous effect are similar to those of the first embodiment.

Incidentally, the first and second embodiments may also be arranged so as to record original images directly for dyed images, without compressing them through division into blocks or smoothing.

A fourth embodiment shown in FIG. 15 is to compress image data by thinning-out of sampling points.

In this embodiment, as shown in FIG. 15, the output terminals of the frame memories 33R, 33G, 33B in the first embodiment are connected to input terminals of a selector switch 61 of the 3-input, 1-output type, respectively. The selector switch 61 has an output terminal connected to a thinning-out circuit 62. An output of the thinning-out circuit 62 is then recorded in the recording system 35.

An output terminal of the recording system 35 is connected to an expansion circuit 63, an output terminal of which is in turn connected to an input terminal of a selector switch 64 of the 1-input, 3-output type. Output terminals of the selector switch 64 are connected to the frame memories 37R, 37G, 37B in the first embodiment, respectively.

The frame memories 33R, 33G, 33B, 37R, 37G, 37B, the selector switches 61, 64, the thinning-out circuit 62, the recording system 35, and the expansion circuit 63 are all controlled by a control circuit 66.

In this embodiment, the frame memories 33R, 33G, 33B are read successively so that R, G, B signals are time-serially input to the thinning-out circuit 62 through the selector switch 61 which is changed over for each of the R, G, B signals. Depending on the input signal, the thinning-out circuit 62 changes the number of pixels thinned out and processes the R, G, B signals time-serially. For example, as shown in FIG. 16a, the R signal is processed to record one pixel for every 4×4 pixels (i.e., 16 pixels) and, as shown in FIG. 16b, the B signal is processed to record one pixel for every 2×2 pixels (i.e., 4 pixels). As to the G signal, all pixels are recorded without being thinned out. Note that black circles represent those pixels which are recorded and while circles represent those pixels which are thinned out, in FIGS. 16a and 16b.

The recording system 35 successively reproduces the R, G, B signals which are input to the expansion circuit 63. Depending on the input signal, the expansion circuit 63 changes the number of pixels expanded and process the R, G, B signals time-serially. More specifically, the R signal is processed to create data of 16 pixels from one pixel data, and the B signal is processed to create data of 4 pixels from one pixel data. As to the G signal, the readout data is output directly without being expanded. The R, G, B signals time-serially delivered from the expansion circuit 63 are stored in the frame memories 37R, 37G, 37B through the selector switch 64 changed over for each of the R, G, B signals, respectively.

As stated before, even if the R signal is recorded and then reproduced through thinning-out of sampling points, the quality of the reproduced image is hardly deteriorated. In this embodiment, therefore, the thinning-out ratio of the R signal, i.e., the compression ratio of data, is set larger than that of other signals.

Other configuration, operation and advantageous effect are similar to those of the first embodiment.

Next, a fifth embodiment of the present invention will be described below.

While an image is compressed using an average value of respective density values of pixels in each block in the foregoing first embodiment, a representative value is used instead of the average value in this fifth embodiment.

Figure 17:
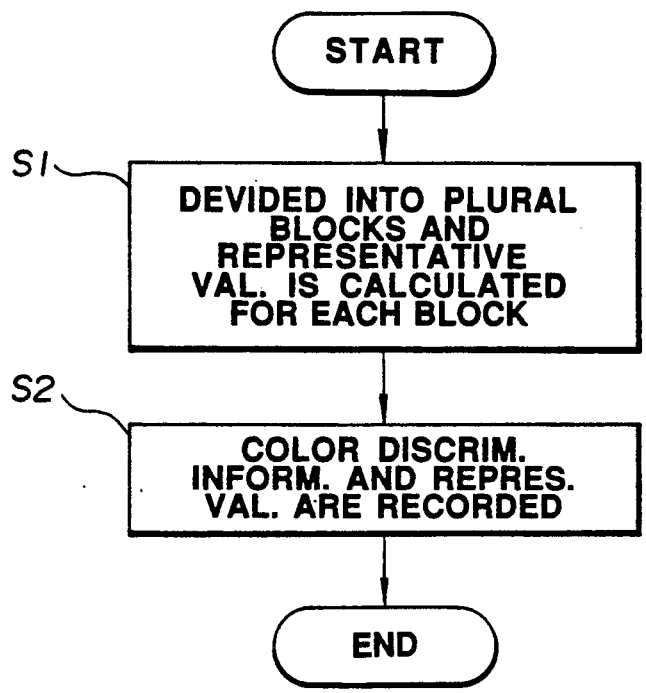
Figure 18:
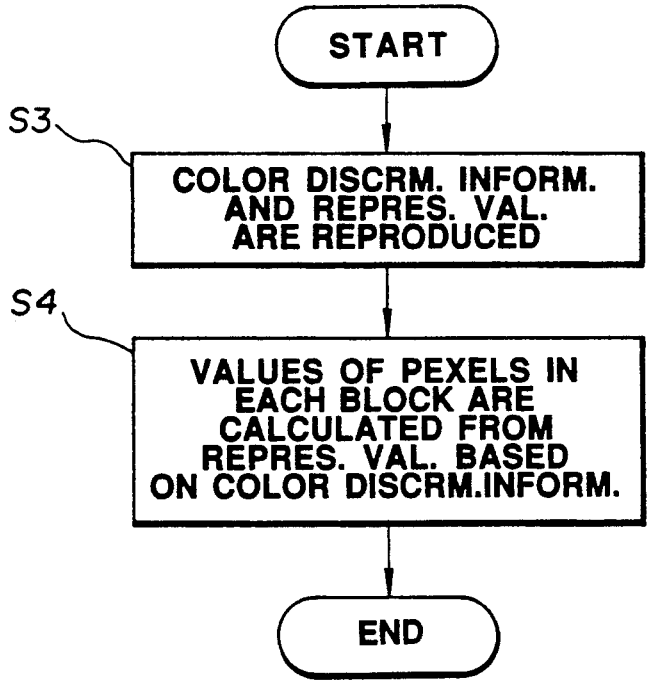

Accordingly, this embodiment performs the processing as shown in a flowchart of FIG. 17 instead of that for the compression circuit 34 as shown in the flowchart of FIG. 4, as well as the processing as shown in a flowchart of FIG. 18 instead of that for the expansion circuit 36 as shown in the flowchart of FIG. 5. FIGS. 17 and 18 are identical to FIGS. 4 and 5 except for replacing the average value in the latter with the respresentative value in the former.

In this embodiment, the representative value is determined through steps of arranging the density values of the pixels in each block in smaller order and selecting the value at the middle as a representative value.

Figure 19A:
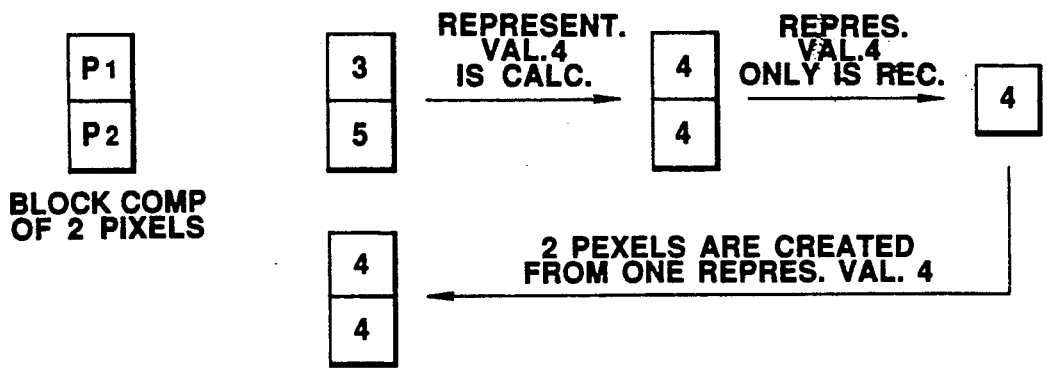
FIGS. 19a, 19b, and 19c are an explanatory view for explaining a compressing operation of a compression circuit.
Figure 19B:
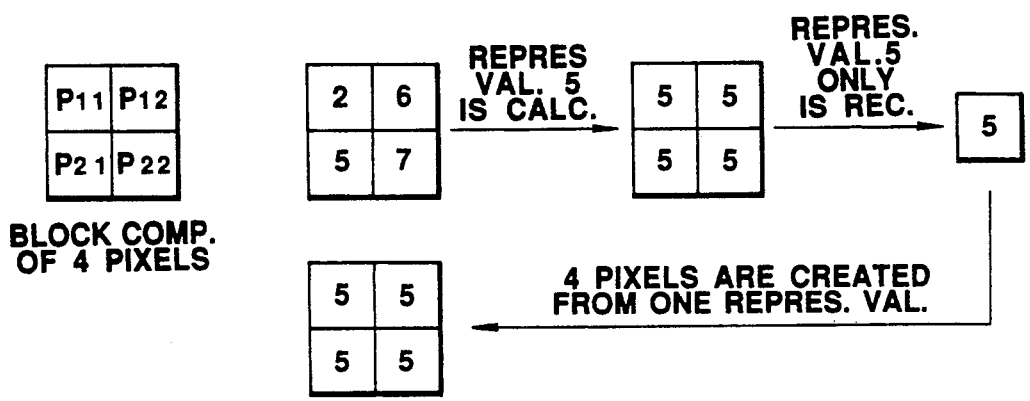
Figure 19C:
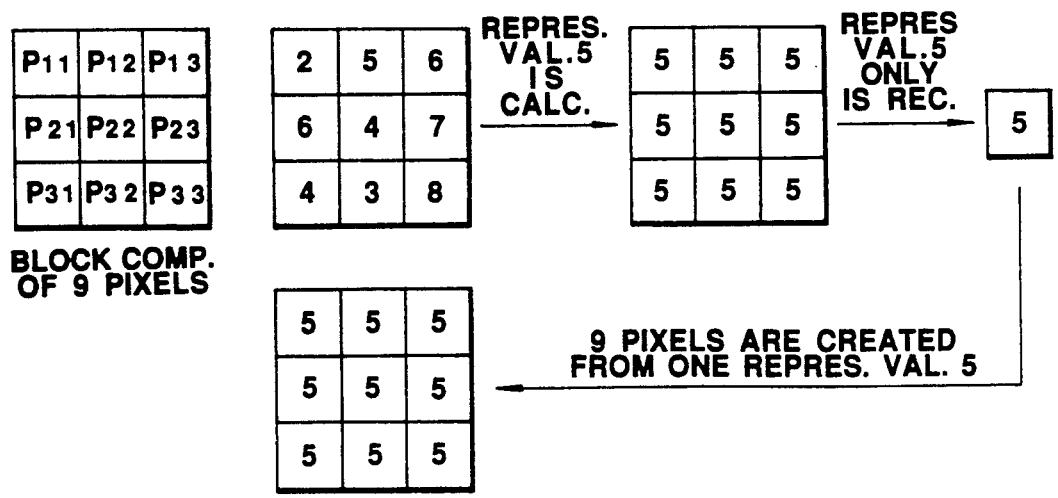

FIGS. 19a, 19b and 19c show explanatory views in which concrete density values (hereinafter abbreviated to simply as values) are put in for respective pixels in each of R, G, B blocks.

For the R block, as shown in FIG. 19a, one block comprises two pixels which have values (3, 5) by way of example. These values are arranged to be (3, 5) in smaller order. Here, the larger value (5) is selected as a representative value.

For the B block, as shown in FIG. 19b, the values of four pixels are arranged to be (2, 5, 6, 7) in smaller order. Although either (5) or (6) corresponds to the value at the middle, the larger one (6) is selected here as a representative value.

For the G block, as shown in FIG. 19c, the values of nine pixels are arranged to be (2, 3, 4, 4, 5, 6, 6, 7, 8) in smaller order. Therefore, the middle value (5) is selected as a representative value.

Thus, in this fifth embodiment, the image data are compressed using the representative values instead of the average values in the first embodiment. In other points, the fifth embodiment is constituted similarly to the first embodiment. Moreover, the advantageous effect of the fifth embodiment is substantially the same as that of the first embodiment.

Figure 20:
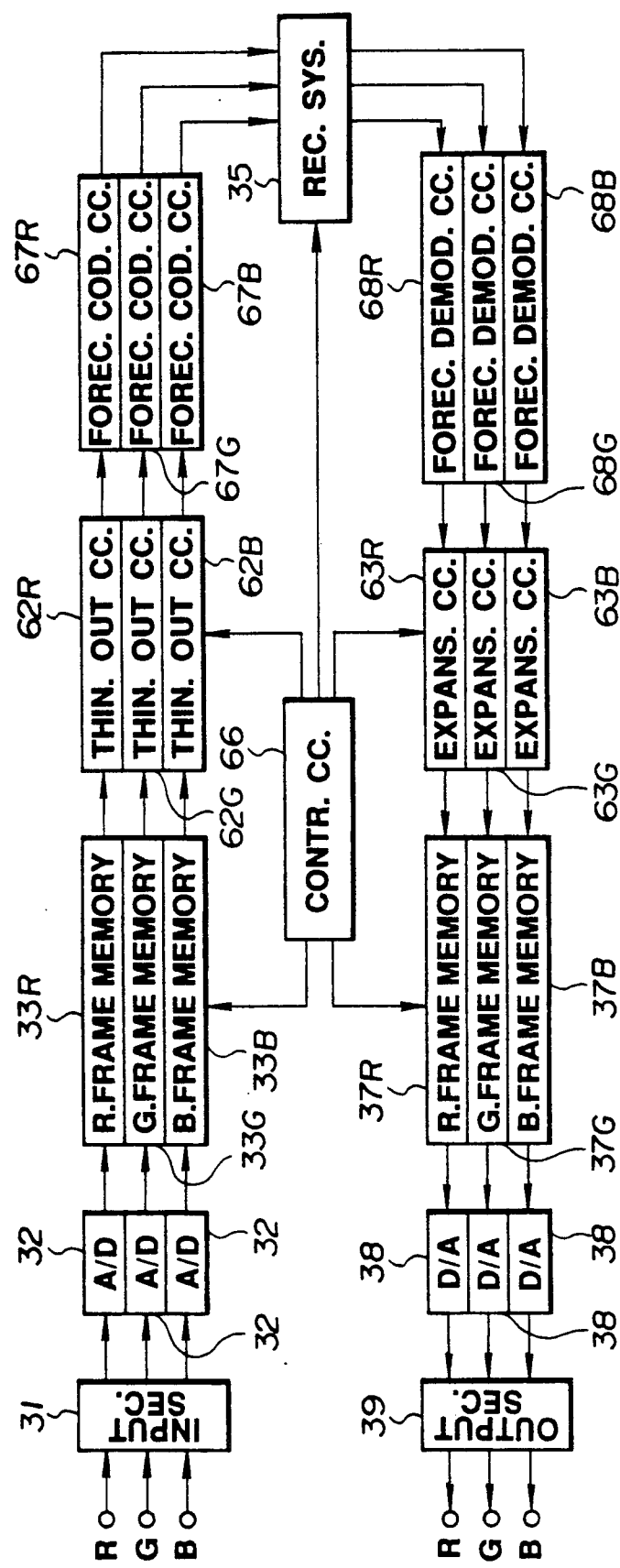
FIG. 20 is a block diagram showing the configuration of an image recording apparatus according to a sixth embodiment of the present invention.

FIG. 20 shows the configuration of a principal part of a sixth embodiment of the present invention.

On the basis of the fourth embodiment shown in FIG. 15, this sixth embodiment is constituted to carry out the forecast coding process in addition to the thinning-out process, as well as the forecast decoding process in addition to the expanding process.

More specifically, the R, G, B image data read out of the frame memories 33R, 33G, 33B are subjected to the thinning-out process in thinning-out circuits 62R, 62G, 62B and then subjected to the forecast coding process in forecast coding circuits 67R, 67G, 67B, respectively. The resultant compressed image data are recorded in the recording system.

In reproducing, the compressed R, G, B image data reproduced out of the recording system 35 are respectively input to forecast decoding circuits 68R, 68G, 68B for being subjected to the forecast decoding process which corresponds to the reverse of the above forecast coding process, and then applied to expansion circuits 63R, 63G, 63B for being expanded to restore those pixels which have been thinned out in the thinning-out process.

Other configuration and operation are similar to those of the fourth embodiment.

With the fifth embodiment, it is possible to set the compression ratio greater than that in the fourth embodiment and hence to increase the number of image frames recordable.

Figure 21:
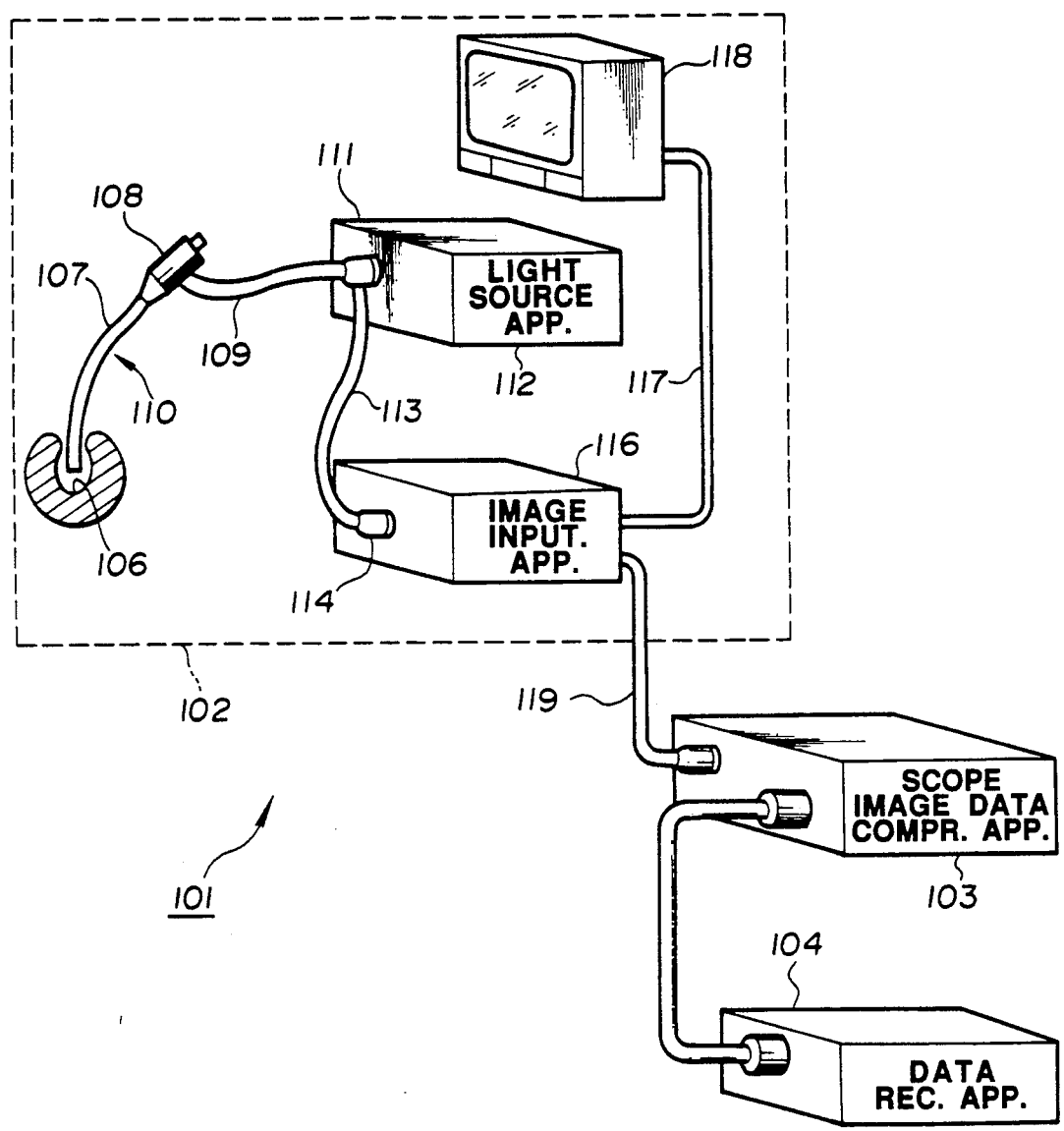

FIG. 21 shows an endoscope image filing apparatus according to a seventh embodiment of the present invention.

In FIG. 21, an endoscope image filing apparatus 101 comprises an endoscope apparatus 102, a scope image data compressing apparatus 103, and a data recording apparatus 104.

The endoscope apparatus 102 includes an electronic scope 110 having a flexible and elongate insert section 107 which is inserted into a location 106 to be observed, an operating section 108 continuously provided at the rear end of the insert section 107, and a universal cable 109 laterally extended from the operating section 108.

Provided at the rear end of the universal cable 109 is a connector 111 which is connected to a light source apparatus 112 for supplying a beam of illumination light to the connector 111. A signal cable 113 is laterally extended from the connector 111, and a connector 114 provided at the rear end of the signal cable 113 is connected to an image inputting apparatus 116. The image inputting apparatus 116 is capable of processing an image signal obtained by the electronic scope 110 to create a video signal comprising three RGB primary color signals, for example, so that an endoscope image can be observed by a TV monitor 118 through a cable 117. The video signal created by the image inputting apparatus 116 is also sent out to the scope image data compressing apparatus 103 through a cable 119. The scope image data compressing apparatus 103 is in turn connected to the data recording apparatus 104 through a cable 121.

The endoscope apparatus 102 will now be described in detail by referring to FIG. 22.

At the distal end of the insert section 107 of the electronic scope 110, there is disposed the emergent end face of a light guide 122 formed by a bundle of fibers through which the illumination light supplied from the light source apparatus 112 is emitted to the observed location 106. The light guide 122 is extended through the insert section 107, the operating section 108 and the universal cable 109 up to the connector 111, and the illumination light is supplied to the light guide 122 by connecting the connector 111 to the light source apparatus 112.

At the distal end of the insert section 107, there is also provided an objective lens 123. A CCD 124 as a solid imaging device 8 is disposed such that its image sensing surface locates at a focus position of the objective lens 123. Connected to the CCD 124 is a bundle of signal lines 126 (indicated by a single line for simplicity) which transmit therethrough an electric signal resulted from photoelectrically converting an object image focused on the image sensing surface of the CCD 124, and a drive clock signal for driving the CCD 124. The signal lines 126 are extended through the insert section 107, the operating section 108 and the universal cable 109 to the connector 111, from which the signal lines 126 are further extended through a signal cable 113 to a connector 114.

The light source apparatus 112 includes a light source lamp 131. Along an optical path connecting the light source lamp 131 and the incident end face of the light guide 122, there are disposed a collimator lens 132 for turning a divergent beam of illumination light from the light source lamp 131 into a parallel beam, a rotating filter 133, and a condenser lens 134 for condensing the parallel illumination light to enter the incident end face of the light guide 122, in this order from the side of the light source lamp 131. The rotating filter 133 is in the form of a disk, and has color transmission filters 134R, 134G, 134B arranged in the circumferential direction with equal angular distances and capable of passing beams of red (R), green (G) and blue (B) light therethrough, respectively, for example. The illumination light converted by the collimator lens 132 to a parallel beam enters those color transmission filters 134R, 134G, 134B. The rotating filter 133 is driven by a motor 135 to rotate for supplying three beams of red, green and blue light to the light guide 122 time-serially.

By connecting the aforesaid connector 114 to the image inputting apparatus 116, the signal lines 126 are connected to an image processing section 136 provided in the image inputting apparatus 116. The image processing section 136 functions to apply the drive clock signal for driving the CCD 124, and convert an electric signal sent out from the CCD 124 to RGB video signals, followed by outputting it. The image processing section 136 also functions to control a balance between image signal levels of the R, B signals, and the like. In addition, it further functions to superpose patient data, an error message or the like, which is sent from a control section 137 described later, on the RGB video signals. An output of the image processing section 136 is delivered to an image memory 138. Depending on a control signal from the control section 137, the image memory 138 passes directly the RGB video signals applied thereto, or stores the RGB video signals temporarily as a still picture to be capable of repeatedly outputting it. An output of the image memory 138 is branched such that one branched output is delivered to a TV monitor 118 for displaying an image of the observed location 106 on a screen, and the other branched output is delivered to the scope image data compressing apparatus 103.

The control section 137 is connected to both a data inputting section 139 such as a keyboard, for example, and a communication interface 130. With a keying operation by a user, the data inputting section 139 applies the patient data such as the name and the date of birth of each patient, and a control signal for image recording (releasing) or the like, the patient data being delivered to the image processing section 136 to be superposed on the RGB video signals as indicated before. Further, the control signal is delivered to the communication interface 130, as well as to the image memory 138 as mentioned above. The communication interface 130 comprises an interface section for serial transmission in accordance with the RS-232C standards, for example, to make inputting and outputting of the data and the control signal with respect to the exterior under control of the control section 137. The communication interface 130 also makes inputting and outputting of the data and the control signal with respect to the scope image data compressing apparatus 103.

The RGB video signals, the data and the control signal are delivered to the scope image data compressing apparatus 103 through the cable 119.

Figure 23:
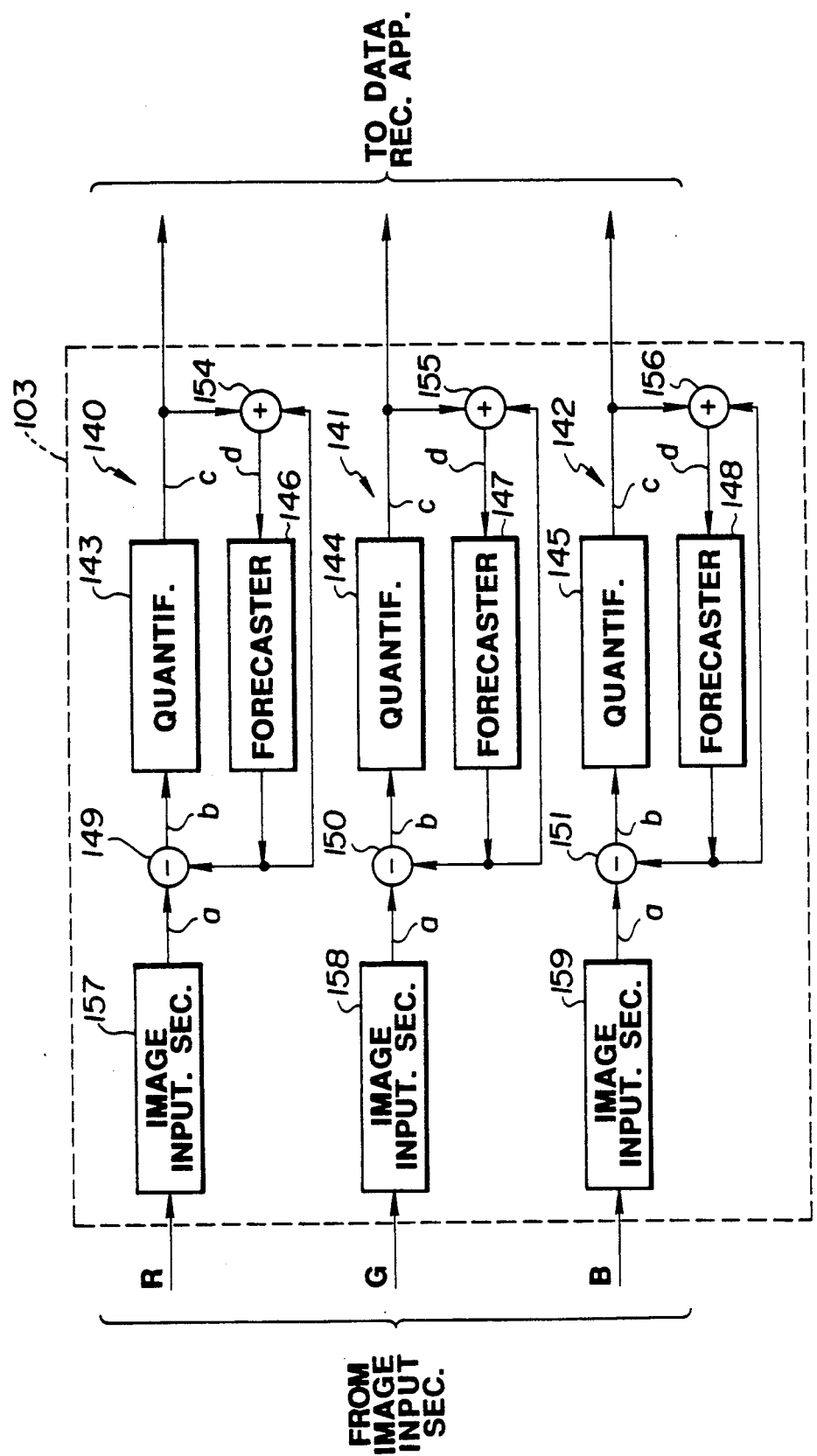

The scope image data compressing apparatus 103 will now be described by referring to FIG. 23.

The image memory 138 is connected to each of image inputting section 157, 158, 159 of the scope image data compressing apparatus 103 so that the RGB video signals are converted to respective digital signals. The image inputting sections 157, 158, 159 have their output terminals connected to forecast coders 140, 141, 142 such that the R signal is input to the forecast coder 140, the G signal is input to the forecast coder 141, and the B signal is input to the forecast coder 142, respectively.

The forecast coders 140, 141, 142 have quantizers 143, 144, 145 as quantizing means, forecasters 146, 147, 148, subtracters 149, 150, 151, and adders 154, 155, 156, respectively. The quantizers 143, 144, 145 quantize the input signals, and the forecasters 146, 147, 148 perform forecast coding. Because the forecast coders 140, 141, 142 all have the same configuration, the following description will be made by taking the forecast coder 140 as an example. The R signal applied to the forecast coder 140 is applied to one input terminal of the subtracter 149. An output terminal of the subtracter 149 is connected to an input terminal of the quantizer 143 for quantizing the R signal. The quantized image data is branched in order to be delivered to the data recording apparatus 104 at one branch and to an input terminal of the adder 154 at the other branch. An output terminal of the adder 154 is connected to an input terminal of the forecaster 146, and an output of the forecaster 146 is connected to the other input terminal of the subtracter 149 and the other input terminal of the adder 154.

The following Table 3 shows a code allocating table used in the forecast coder 140 to which the R signal is applied. As will be seen from the Table 3, a forecast error $\Delta P$ applied to the quantizer 143 is quantized into seven gradations, i.e., 3 bits.

TABLE 3

| $\Delta P$ | $-1 \sim +1$ | $+2 \sim +6$ | $-6 \sim -2$ | $+7 \sim +15$ | $-15 \sim -7$ | $+16 \sim +255$ | $-255 \sim -16$ |
|---|---|---|---|---|---|---|---|
| Output Value | 0 | +4 | −4 | +10 | −10 | +20 | −20 |
| Code | 1 | 2 | 3 | 4 | 5 | 6 | 7 |

The following Table 4 shows a code allocating table used in the forecast coders 141, 142 to which the G and B signals are applied, respectively. As will be seen from the Table 4, a forecast error $\Delta P$ applied to the quantizers 144, 145 is quantized into fifteen gradations, i.e., 4 bits.

TABLE 4

| $\Delta P$ | $-1 \sim +1$ | $+2 \sim +3$ | $-2 \sim -3$ | $+4 \sim +6$ | $-6 \sim -4$ | $+7 \sim +9$ | $-9 \sim -7$ | $+10 \sim +15$ |
|---|---|---|---|---|---|---|---|---|
| Output Value | 0 | +2 | −2 | +5 | −5 | +8 | −8 | +12 |
| Code | 1 | 2 | 3 | 4 | 5 | 6 | 7 | 8 |
| $\Delta P$ | $-15 \sim -10$ | $+16 \sim +25$ | $-25 \sim -16$ | $+26 \sim +35$ | $-35 \sim -26$ | $+36 \sim +255$ | $-255 \sim -36$ | |
| Output Value | −12 | +20 | −20 | +30 | −30 | +50 | −50 | |
| Code | 9 | 10 | 11 | 12 | 13 | 14 | 15 | |

Operation of the scope image data compressing apparatus 103 thus constituted will be described below.

Prior to recording an image, the user selects an ID input mode by the data inputting section 139 of the endoscope apparatus 102, and enters the patient data such as the name and the date of birth of a patient. When the ID input mode is selected, the control section 137 superposes the patient data on the RGB video signals, and also outputs a signal to the scope image data compressing apparatus 103 via the communication interface 130 to confirm whether or not the apparatus 103 is in a state able to communicate. In response to this, the scope image data compressing apparatus 103 transmits a signal, indicating a state able to communicate, to the communication interface 130. The signal indicating a state able to communicate is sent from the communication interface 130 to the control section 137 which then displays such an indication on the screen of the TV monitor 118, for example. Upon seeing the indication, the user enters a release signal from the data inputting section 139. When the control section 137 receives the release signal, it inhibits writing of the new image data into the image memory 138 so that the image memory 138 brings the image into a standstill and outputs the same image data repeatedly. Furthermore, the control section 137 transmits the release signal from the communication interface 130 to the scope image data compressing apparatus 103. Upon sensing the release signal sent thereto, the scope image data compressing apparatus 103 starts operating the forecast coders 140, 141, 142.

Operations of the forecast coders 140, 141, 142 will now be described by referring to Tables 5 and 6 below.

TABLE 5

|  | (1) | (2) | (3) | (4) | (5) |
|---|---|---|---|---|---|
| Original image data a | +12 | +6 | +20 | +4 | 0 |
| Subtracter output b | +12 | −4 | +14 | −12 | −6 |
| Quantizer output c | +10 | −4 | +10 | −10 | −4 |
| Code | 4. | 3 | 4 | 5 | 3 |
| Adder output d | +10 | +6 | +16 | +6 | +2 |

Note that (1), (2), (3), (4), (5) in the above Table stand for pixels of each image.

At the outset, in the forecast coder 140 to which the R signal is applied, original image data $a = +12$ of the pixel (1) in the Table 5 is input to the subtracter 149. In the absence of preceding data, the subtracter 149 delivers the input data to the quantizer 143 directly. The quantizer 143 quantizes the input data in accordance with the code allocating table given by the Table 3, followed by delivering an output $c = +10$ to both the data recording apparatus 104 and the adder 154. In the absence of preceding data, the adder 154 applies the delivered image data, as an output d, directly to the forecaster 146, and output data of the forecaster 146 is delivered to both the subtracter 149 and the adder 154.

Then, when original image data $a = +6$ of the pixel (2) is applied, the output b of the subtracter 149 becomes −4 resulted by subtracting the preceding image data +10 from the current image data +6. The output $b = −4$ of the subtracter 149 is quantized in accordance with the code allocating table given by the Table 3, and the quantized output $c = −4$ is delivered to both the data recording apparatus 104 and the adder 154. The adder 154 adds the preceding data +10 to the current data −4, and delivers the sum +6 as its output d. This output d of the adder 154 is delivered through the forecaster 146 to both the subtracter 149 and the adder 154. Subsequently, forecast coding will be performed in a like manner, with the result that respective image data are output as any one of seven codes, i.e., a 3-bit signal, and recorded in the data recording apparatus 104.

Meanwhile, in the forecast coder 141 to which the G signal is applied, original image data $a = +1$ of the pixel (1) in the Table 6 is input to the subtracter 150. In the absence of preceding data, the subtracter 150 delivers the input data to the quantizer 144 directly. The quantizer 144 quantizes the input data in accordance with a code allocating table given by the Table 4, followed by delivering 0 to both the data recording apparatus 104 and the adder 155. In the absence of preceding data, the adder 155 applies the delivered image data directly to the forecaster 147, and output data of the forecaster 147 is delivered to both the subtracter 150 and the adder 155.

Then, when original image data $a = +6$ of the pixel (2) is applied, the output of the subtracter 150 becomes $b = +6$ resulted by subtracting the preceding image data 0 from the current image data $a = +6$. The output $b = +6$ of the subtracter 150 is quantized in accordance with a code allocating table given by the Table 4, and the quantized output $c = +5$ is delivered to both the data recording apparatus 104 and the adder 155. The adder 155 adds the preceding data 0 to the current data +5, and delivers an output $d = +5$. This output d of the adder 155 is delivered through the forecaster 147 to both the subtracter 150 and the adder 155. Subsequently, forecast coding will be performed in a like manner, with the result that respective image data are output as any one of fifteen codes, i.e., a 4-bit signal, and recorded in the data recording apparatus 104.

As with the above forecast coder 141, the forecast coder 142 outputs the image data as a 4-bit signal to be recorded in the data recording apparatus 104.

TABLE 6

|  | (1) | (2) | (3) | (4) | (5) |
|---|---|---|---|---|---|
| Original image data a | +1 | +6 | +35 | +2 | 0 |
| Subtracter output b | +1 | +6 | +30 | −32 | −6 |
| Quantizer output c | 0 | +5 | +30 | −30 | −5 |
| Code | 1 | 4 | 12 | 13 | 5 |
| Adder output d | 0 | +5 | +35 | +5 | 0 |

Note that (1), (2), (3), (4), (5) in the above Table stand for pixels of each image.

With this embodiment, as described above, by quantizing the R image into a 3-bit signal, a quantity of image data can be reduced as compared with the case of quantizing all of the RGB images using 4-bit forecast errors, enabling to record a larger quantity of image correspondingly.

Figure 24:
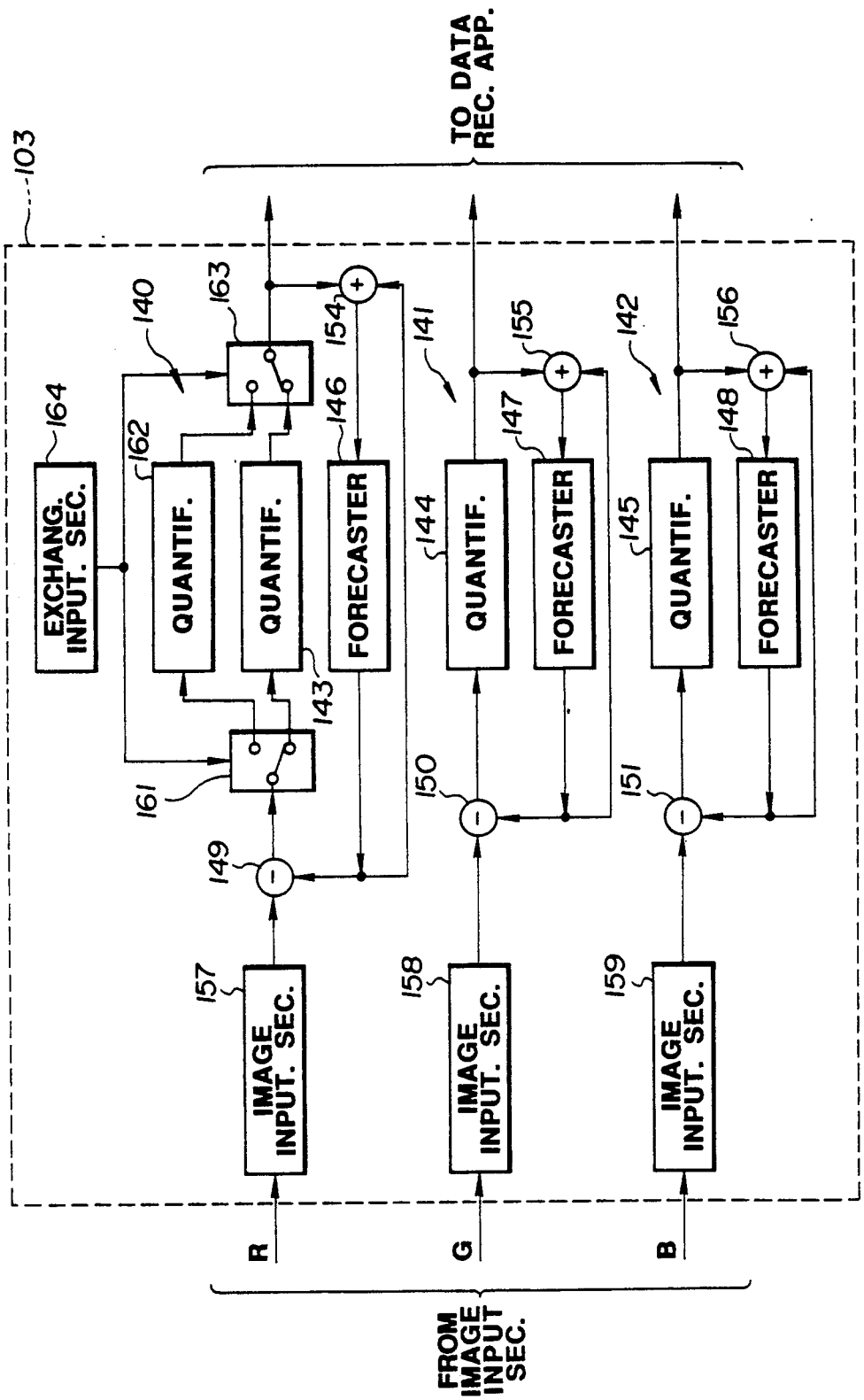
FIG. 24 is a block diagram showing the configuration of a scope image data compressing apparatus according to an eighth embodiment of the present invention.

FIG. 24 is a block diagram for explaining the configuration an scope image data compressing apparatus according to an eighth embodiment of the present invention.

In this embodiment, a 4-bit quantizer is additionally provided in parallel to the aforesaid 3-bit quantizer 143 used in the seventh embodiment, allowing either the 4-bit or 3-bit quantizer to be selectively employed by operating an exchange switch.

In a forecast coder 140 of this embodiment, the signal from the image inputting section 157 is applied to one input terminal of the subtracter 149. The subtracter 149 has its output terminal connected to an input terminal of an exchange switch 161. The exchange switch 161 has one output terminal connected to a quantizer 162, and the other output terminal connected to the quantizer 143. The quantizer 162 performs quantization into a 4-bit signal in accordance with a code allocating table given by the Table 4, while the quantizer 143 performs quantization into a 3-bit signal in accordance with the Table 3 as stated in connection with the seventh embodiment.

An output terminal of the quantizer 143 is connected to one input terminal of the exchange switch 163, and an output terminal of the quantizer 162 is connected to the other input terminal of the exchange switch 163. An output terminal of the exchange switch 163 is branched in order to be connected to the data recording apparatus 104 at one branch and to the adder 154 at the other branch.

The exchange switches 161, 163 are controlled in their operations by an exchange inputting section 164 such that those two switches are simultaneously changed over to select either the quantizer 163 or the quantizer 143.

Other configuration and operation are similar to those of the seventh embodiment.

In this embodiment, the provision of the exchange inputting section 164 makes it possible to select either one of the 3-bit quantizer 143 and the 4-bit quantizer 162 as required.

Although there causes no problem in a normal endoscope image even when a 3-bit code is allocated to the R signal for quantization, allocation of the 3-bit code may not suffice the required gradations for a dyed image because a quantity of information in the R component is increased. With this embodiment, however, in the case of an image such as a dyed image which requires more graduations, 4-bit gradations can be assigned to that image through an operation from the exterior. It is hence possible to provide gradations as many as desired even for a particular endoscope image.

The above mentioned embodiments are not limited in application to frame-sequential type electronic endoscopes using RGB signals, and also applicable to single-plate type electronic endoscopes for decoding a composite video signal. The endoscope may be of the type having an image sensing device at the distal end, or of the type introducing an object image to the exterior through an image guide formed of optical fibers and receiving the image by an image sensing device.

In the above mentioned embodiments, taking into account a feature that the spatial frequency component of a component image corresponding to the longest wavelength region, i.e., of a red component image in the endoscope image, is concentrated in a lower frequency range than other component images, the compression ratio for a component image corresponding to the longest wavelength region is set to the greatest value when recording the respective component images. As a result, a quantity of image information can be reduced to record the larger number of image frames.

In short, the above mentioned embodiments are arranged to perform the image compression in a less wasteful and more efficient manner by making use of a feature of the endoscope image.

Next, there will be described embodiments in which the image compression is efficiently performed by making use of correlation in an image to increase the number of image frames recordable.

Figure 25:
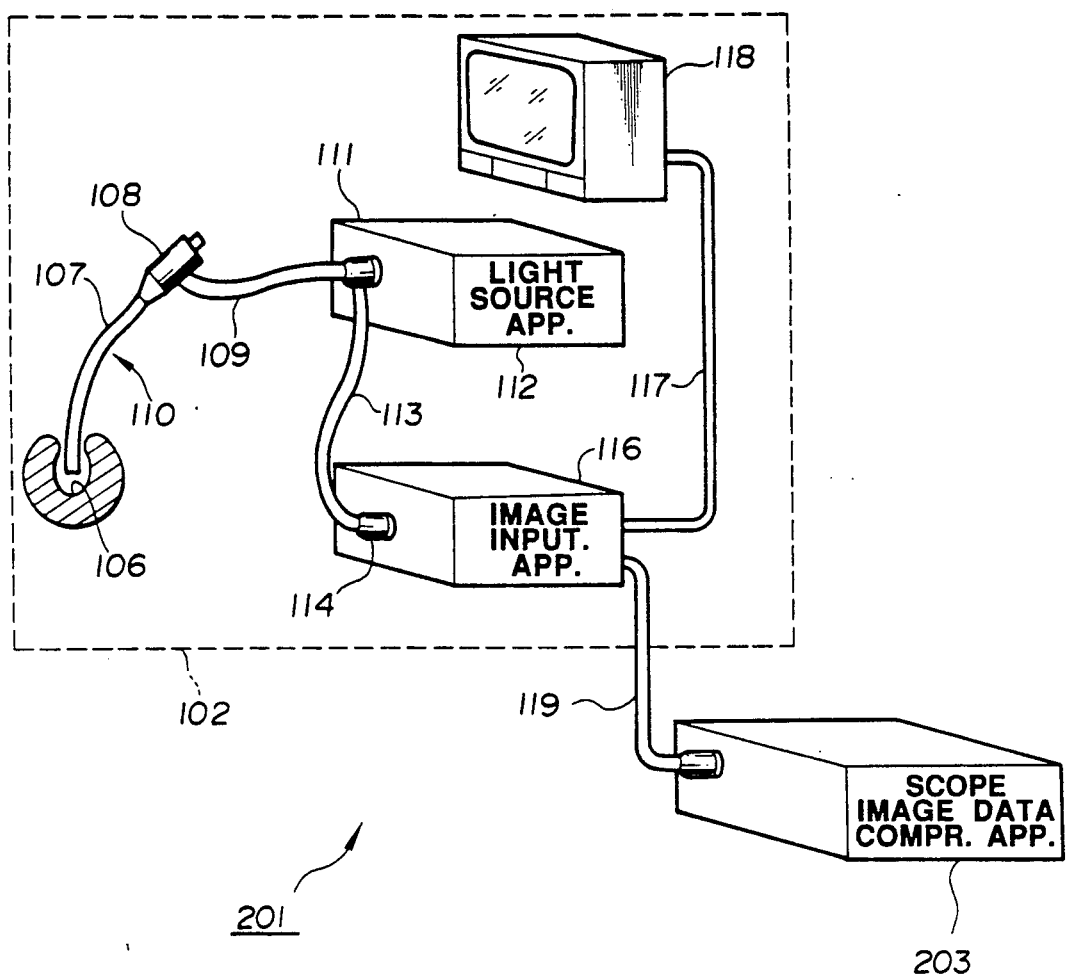

An endoscope image filing apparatus 201 of a ninth embodiment shown in FIG. 25 comprises an endoscope apparatus 102 and a scope image data compressing apparatus 203.

Figure 22:
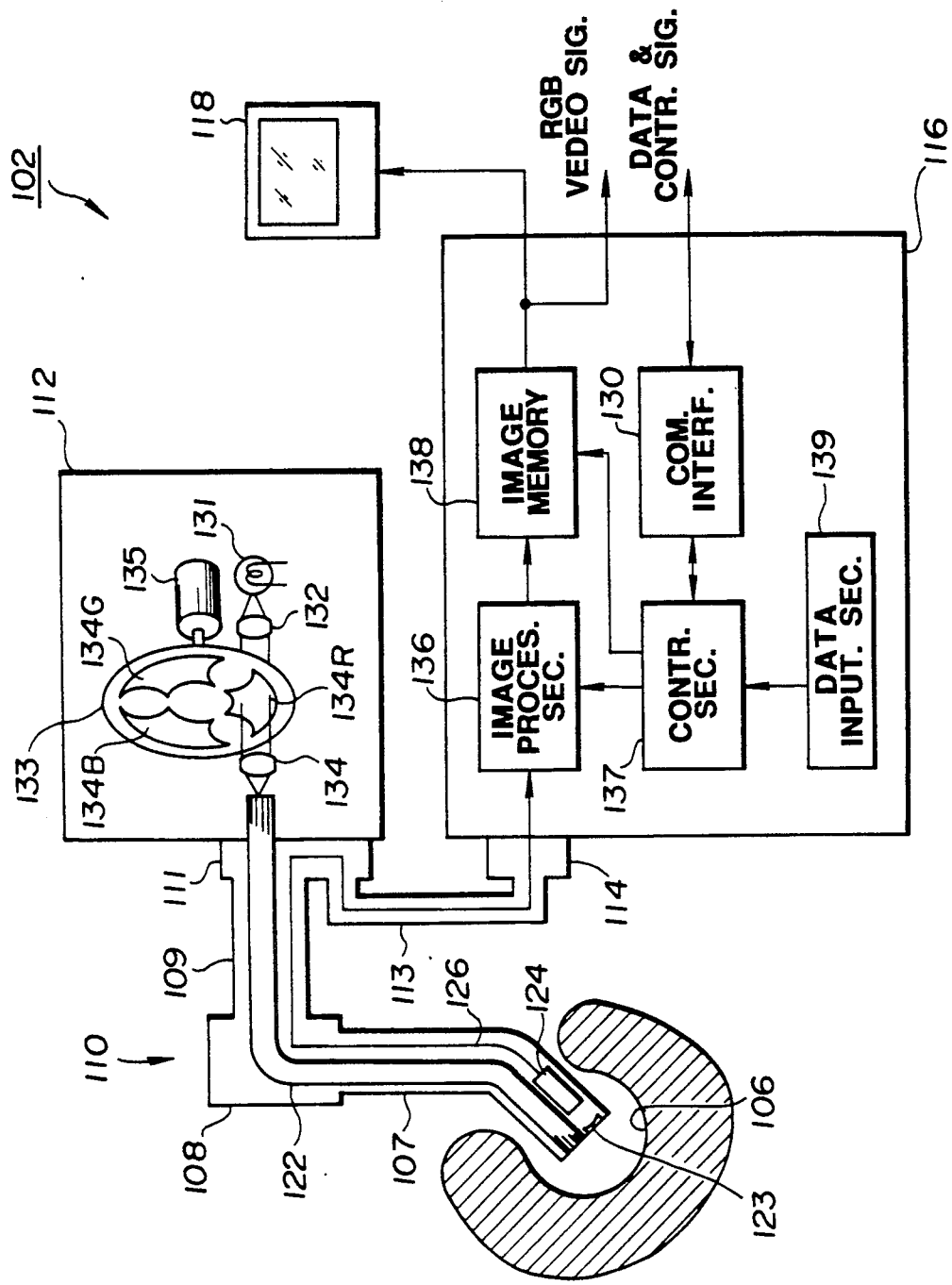

The configuration of the endoscope apparatus 102 is the same as that shown in FIGS. 21 and 22, and hence is not described here.

Figure 26:
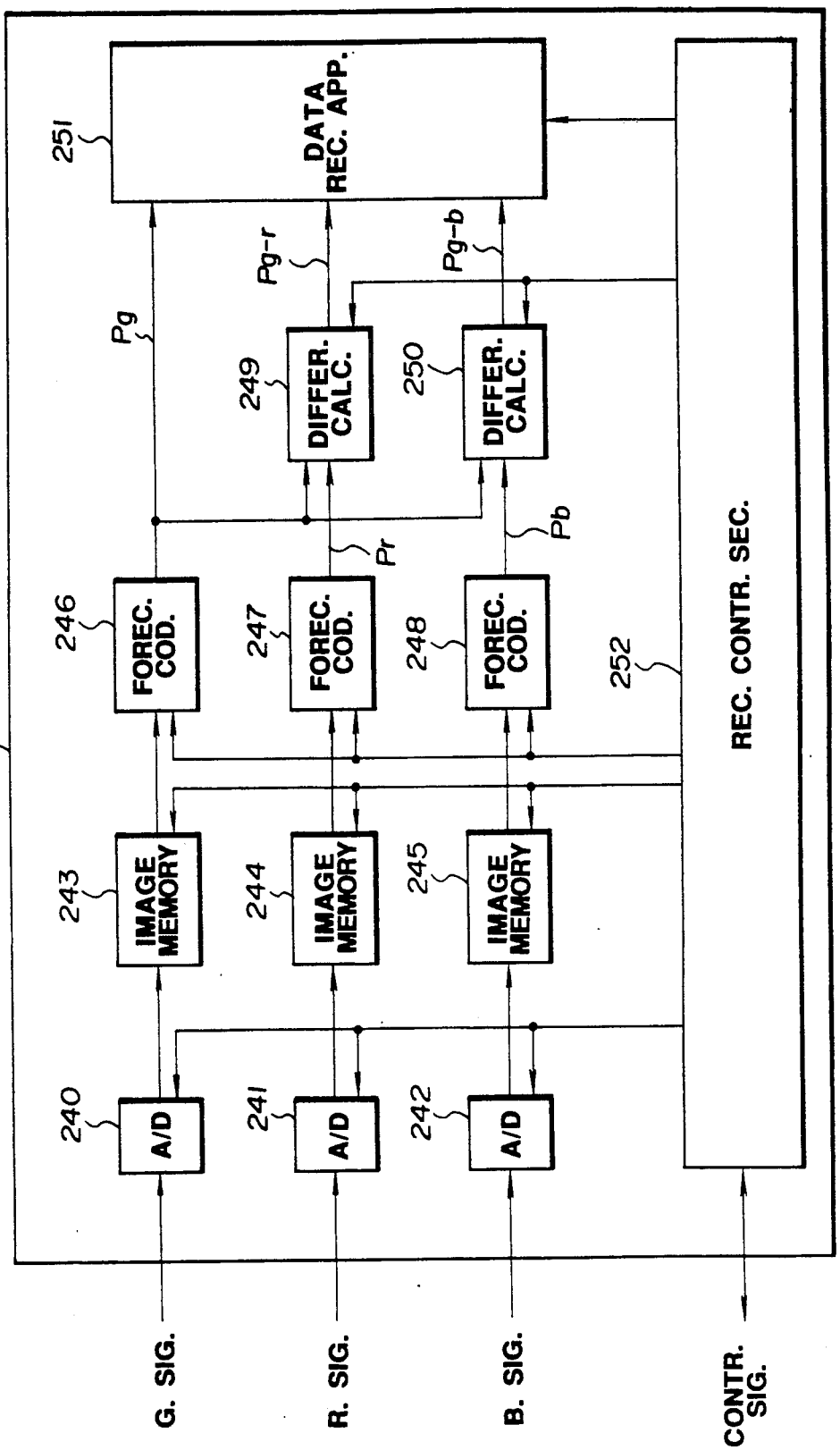

The scope image data compressing apparatus 203 is constituted as shown in FIG. 26.

The image memory 138 (see FIG. 22) in the image inputting apparatus 116 is connected to each of A/D converters 240, 241, 242 of the scope image data compressing apparatus 203, so that G, R and B signals are input to the A/D converters 240, 241 and 242, respectively. The RGB video signals are converted to digital signals by the A/D converters 240, 241, 242. The A/D converters 240, 241, 242 are connected to image memories 243, 244, 245, and these image memories 243, 244, 245 are connected to forecast coders 246, 247, 248 as first compression means, respectively. An output terminal of the forecast coder 246 is connected to both a data recording apparatus 251 and one input terminals of differential calculators 249, 250 as second compression means. An output terminal of the forecast coder 247 is connected to the other input terminal of the differential calculator 249, and an output terminal of the forecast coder 248 is connected to the other input terminal of the differential calculator 250.

Output terminals of the differential calculators 249, 250 are connected to the data recording apparatus 251.

Further, a recording control section 252 is connected to the aforesaid control section 137 through the communication interface 130 in the image inputting apparatus 116 for controlling the A/D converters 240, 241, 242, the image memories 243, 244, 245, the forecast coders 246, 247, 248, the differential calculators 249, 250 and the data recording apparatus 251 in accordance with a control signal sent from the control section 137.

Operation of the scope image data compressing apparatus 203 thus constituted will be described below.

Prior to recording an image, the user selects an ID input mode by the data inputting section 139 of the endoscope apparatus 102, and enters the patient data such as the name and the date of birth of a patient. When the ID input mode is selected, the control section 137 superposes the patient data on the RGB video signals, and also outputs a signal to the recording control section 252 of the scope image data compressing apparatus 203 via the communication interface 130 to confirm whether or not the apparatus 203 is in a state able to communicate. In response to this, the recording control section 252 transmits a signal, indicating a state able to communicate, to the communication interface 130. The signal indicating a state able to communicate is sent from the communication interface 130 to the control section 137 which then displays such an indication on the screen of the TV monitor 118, for example. Upon seeing the indication, the user enters a release signal from the data inputting section 139. When the control section 137 receives the release signal, it inhibits writing of the new image data into the image memory 138 so that the image memory 138 brings the image into a standstill and outputs the same image data repeatedly. Furthermore, the control section 137 transmits the release signal from the communication interface 130 to the recording control section 252. Upon sensing the release signal sent thereto, the recording control section 252 sends a control signal to the A/D converter 240 and the image memory 243, causing the image memory 243 to hold the G image of one frame. Likewise, the recording control section 252 sends a control signal to the A/D converter 241 and the image memory 244, causing the image memory 244 to hold the R image of one frame, and also sends a control signal to the A/D converter 242 and the image memory 245, causing the image memory 245 to hold the B image of one frame.

After the respective images have been held in the image memories 243, 244, 245, the recording control section 252 sends a calculation start signal to each of the forecast coders 246, 247, 248, and also sends a control signal to the image memory 243 for delivering the G image data being held from the image memory 243 to the forecast coder 246. Simultaneously, the recording control section 252 sends a control signal to the image memory 244 for delivering the R image data being held from the image memory 244 to the forecast coder 247, and further sends a control signal to the image memory 245 for delivering the B image data being held from the image memory 245 to the forecast coder 248.

In the forecast coder 246, as shown in the following Table 7, original image data Og of a preceding pixel of the G image is subtracted from original image data Og of a current pixel thereof to determine a forecast error Pg. For example, the original image data 12 of the preceding pixel (1) is subtracted from the original image data 9 of the current pixel (2) to determine the forecast error $Pg = -3$. Afterward, the original data Og of each preceding pixel is subtracted from the original data Og of each current pixel successively to determine the forecast errors Pg for one frame, which are then output to the data recording apparatus 251 and the differential calculators 249, 250. In a like manner, the forecast coder 247 determines forecast errors Pr from original image data Or of the R image, and the forecast coder 248 determines forecast errors Pb from original image data Ob of the B image, respectively. The forecast errors Pr are output to the differential calculator 249, and the forecast errors Pb are output to the differential calculator 250.

TABLE 7

|  | (1) | (2) | (3) | (4) | (5) | (6) |
|---|---|---|---|---|---|---|
| G Image |  |  |  |  |  |  |
| Original image data (Og) | 12 | 9 | 11 | 8 | 8 | 10 |
| Forecast error (Pg) | 12 | −3 | 2 | −3 | 0 | 2 |
| R Image |  |  |  |  |  |  |
| Original image data (Or) | 13 | 10 | 14 | 9 | 8 | 10 |
| Forecast error | 13 | −3 | 4 | −5 | −1 | 2 |
| Diff. forecast error (Pg − r) | −1 | 0 | −2 | 2 | 1 | 0 |
| B Image |  |  |  |  |  |  |
| Original image data (Ob) | 11 | 9 | 10 | 8 | 9 | 12 |
| Forecast error | 11 | −2 | 1 | −2 | 1 | 3 |
| Diff. forecast error (Pg − b) | 1 | −1 | 1 | −1 | −1 | −1 |

Note that (1), (2), (3), (4), (5), (6) in the Table 7 stand for pixels of each image.

In the differential calculator 249, the forecast error Pr of the R image is subtracted from the forecast error Pg of the G image to determine a differential forecast error Pg−r. Taking the pixel (1) as an example, the forecast error 13 of the R image is subtracted from the forecast error 12 of the G image to determine the differential forecast error −1. The similar calculation is performed successively to output the differential forecast errors Pg−r for one frame to the data recording apparatus 251.

Likewise, the differential calculator 250 successively subtracts the forecast error Pb of the B image from the forecast error Pg of the G image to determine differential forecast errors Pg−b for one frame, which are then output to the data recording apparatus 251.

The data recording apparatus 251 records the forecast error Pg and the differential forecast errors Pg−r, Pg−b applied thereto. At the completion of recording to the data recording apparatus 251, an end-of-recording signal is delivered to the control section 137 through the recording control section 252 and the communication interface 130, whereupon the control section 137 displays an indication of the end of recording on the screen of the TV monitor 118, for example.

When reproducing the data recorded in the data recording apparatus 251, the image can be reproduced by executing the above operation in a reversed manner.

With this embodiment, since the forecast errors are determined for the respective RGB images and the differential forecast errors are further determined based on the forecast error of the G image, it is possible to reduce a quantity of data of the R and B images.

Such a reduction in a quantity of data of the R and B images makes it possible to increase a quantity of images recordable in the data recording apparatus 51.

Figure 27:
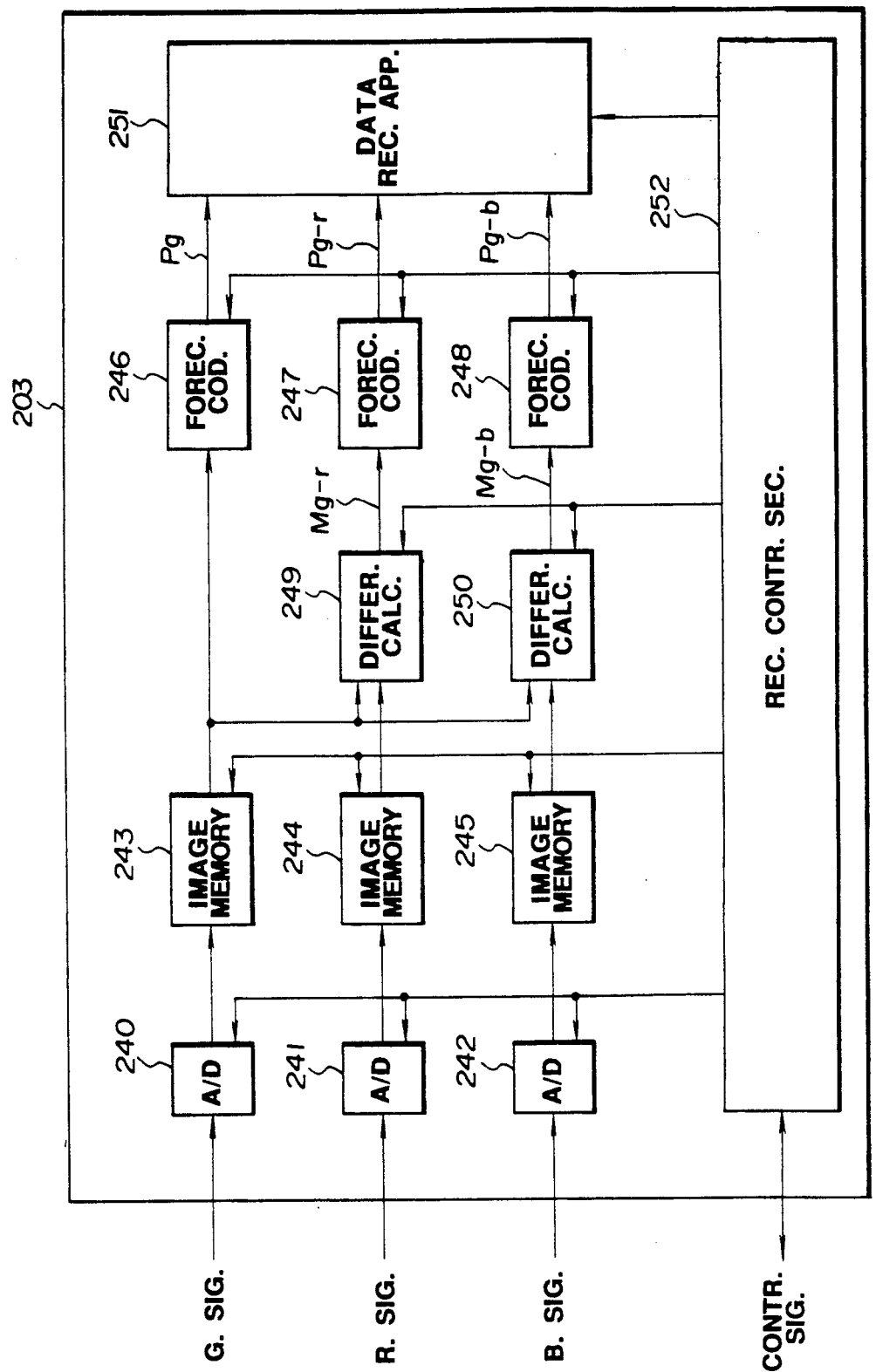
FIG. 27 is a block diagram showing the configuration of a scope image data compression apparatus according to a tenth embodiment of the present invention.

FIG. 27 is a block diagram for explaining the configuration of a scope image data compressing apparatus according to a tenth embodiment of the present invention.

While the differential errors between the component images are determined after forecast coding in the ninth embodiment, differential data are determined before forecast coding in this embodiment.

In a scope data compressing apparatus 203 of this embodiment, the output terminal of the image memory 243 for the G image is connected to the forecast coder 246 and one input terminals of the differential calculators 249, 250. Also, the output terminal of the image memory 244 for the R image is connected to the other input terminal of the differential calculator 249, and the output terminal of the image memory 245 for the B image is connected to the other input terminal of the differential calculator 250.

The output terminal of the differential calculator 249 is connected to the input terminal of the forecast coder 247, while the output terminal of the differential calculator 250 is connected to the input terminal of the forecast coder 248.

The forecast coders 246, 247, 248 have their output terminals connected to the data recording apparatus 251.

Other configuration is similar to that of the ninth embodiment.

Operation of this embodiment will be described below.

When the respective images are held in the image memories 243, 244, 245, the recording control section 252 sends a control signal to the image memory 243 for delivering the G image data being held from the image memory 243 to the forecast coder 246 and the differential calculators 249, 250. Likewise, the recording control section 252 sends a control signal to the image memory 244 for delivering the R image data being held from the image memory 244 to the differential calculator 249, and further sends a control signal to the image memory 245 for delivering the B image data being held from the image memory 245 to the differential calculator 250.

For the G image data applied to the forecast coder 246, as shown in the following Table 8, original image data Og of a preceding pixel of the G image is subtracted from original image data Og of a current pixel thereof to determine a forecast error Pg. For example, the original image data 12 of the preceding pixel (1) is subtracted from the original image data 9 of the current pixel (2) to determine the forecast error Pg=−3. Afterward, the original data Og of each preceding pixel is subtracted from the original data Og of each current pixel successively to determine the forecast errors Pg for one frame, which are then output to the data recording apparatus 251.

TABLE 8

|  | (1) | (2) | (3) | (4) | (5) | (6) |
|---|---|---|---|---|---|---|
| G Image |  |  |  |  |  |  |
| Original image data (Og) | 12 | 9 | 11 | 8 | 8 | 10 |
| Forecast error (Pg) | 12 | −3 | 2 | −3 | 0 | 2 |
| R Image |  |  |  |  |  |  |
| Original image data (Or) | 13 | 10 | 14 | 9 | 8 | 10 |
| Diff. data (Mg − r) | −1 | −1 | −3 | −1 | 0 | 0 |
| Diff. forecast error (Pg − r) | −1 | 0 | −2 | 2 | 1 | 0 |
| B Image |  |  |  |  |  |  |
| Original image data (Ob) | 11 | 9 | 10 | 8 | 9 | 12 |
| Diff. data (Mg − b) | 1 | 0 | 1 | 0 | −1 | −2 |
| Diff. forecast error (Pg − b) | 1 | −1 | 1 | −1 | −1 | −1 |

Note that (1), (2), (3), (4), (5), (6) in the Table 8 stand for pixels of each image.

In the differential calculator 249, the R image data Or is subtracted from the G image data Og to determine differential data Mg−r (or Mg−g). As to the pixel (1), for example, the R image data 13 is subtracted from the G image data 12 to determine the differential data −1. The resultant differential data Mg−r is successively output to the forecast coder 247.

In a like manner, the differential calculator 250 also successively subtracts the B image data Ob from the G image data Og to determined differential data Mg−b (or Mb−g) which is then output to the forecast coder 248.

In the forecast coder 247, the differential data Mg−r of the preceding pixel is subtracted from the differential data Mg−r of the current pixel to determine a differential forecast error Pg−r. For example, the differential data −1 of the preceding pixel (1) is subtracted from the differential data −1 of the current pixel (2) to determine a differential forecast error 0. Then, the differential forecast errors Pg−r for one frame are successively output to the data recording apparatus 251.

Likewise, the forecast coder 248 subtracts the differential data Mg−b of the preceding pixel from the differential data Mg−b of the current pixel to determine a differential forecast error Pb−r. Then, the resultant differential forecast errors Pb−r for one frame are successively output to the data recording apparatus 251.

The data recording apparatus 251 records the forecast error Pg and the differential forecast errors Pg−r, Pg−b applied thereto.

Other operation is similar to that of the ninth embodiment.

This embodiment has the similar advantageous effect to that of the ninth embodiment.

It is to be noted that although the differential data are determined in the foregoing ninth and tenth embodiments by using the G image as the basis, either the R image or the B image may be used as the basis.

Further, although the differential data between the component images are determined above in a digital manner, they may be determined in an analog manner.

With the foregoing ninth and tenth embodiments, since forecast coding in the image and correlation between the respective colors are combined with each other, it is possible to reduce a quantity of data as compared with that as resulted when handling the image data individually.

Therefore, even when the recording capacity is subjected to a limitation, the number of image frames recordable can be increased while suppressing a reduction in the image quality.

Next, there will be described embodiments in which an image is efficiently compressed by making use of an average color.

Figure 28:
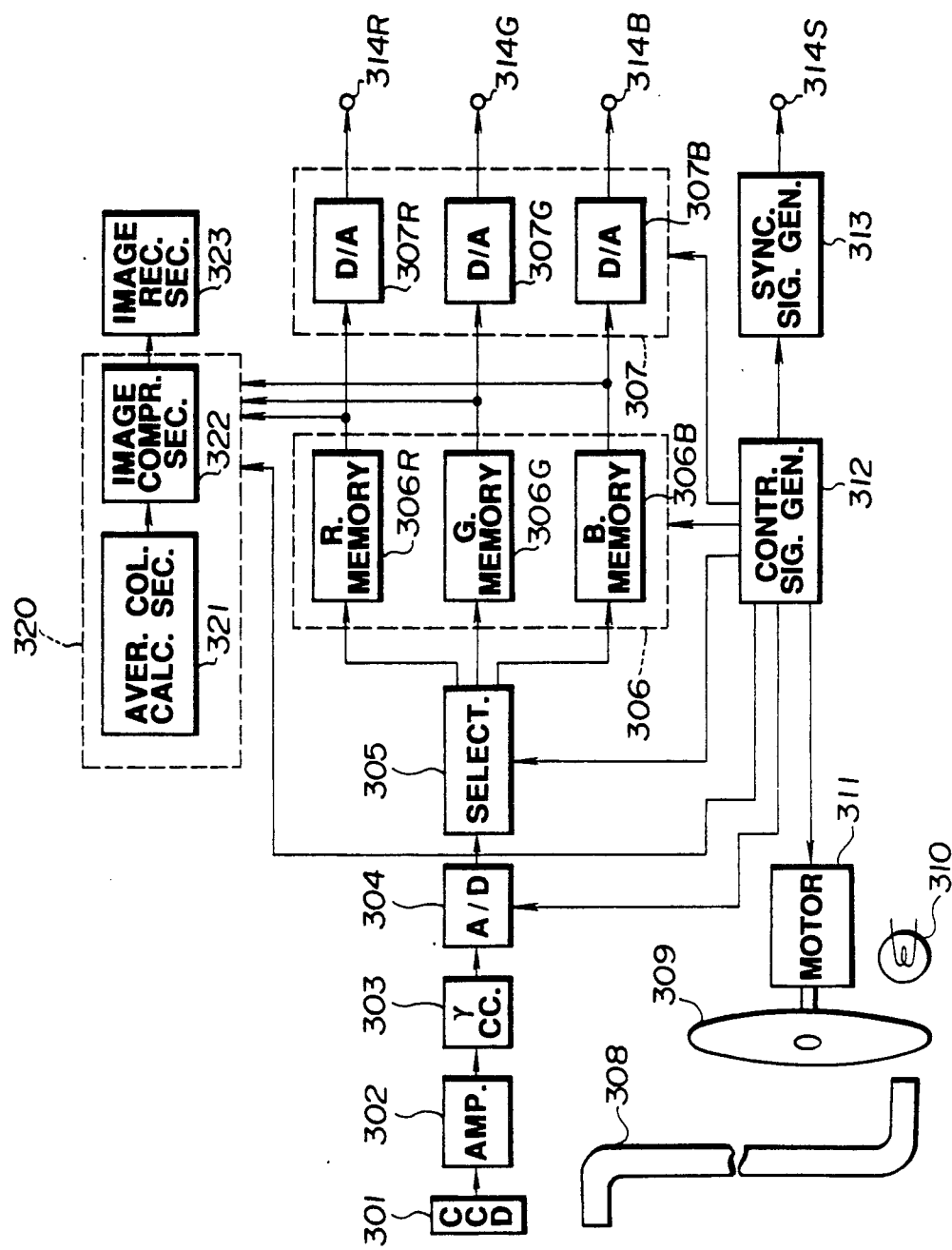

An electronic endoscope apparatus of the frame-sequentially imaging type comprises, as shown in FIG. 28, a control signal generator 312 for generating predetermined control signals to respective blocks explained later; a CCD (Charge Coupled Device) 301 as a solid imaging device adapted to pick up an object image; an amplifier 302 for amplifying and processing an image pick-up signal of the CCD 301 to convert it to a video signal; a gamma ($\gamma$) circuit 303 in which the video signal amplified by the amplifier 302 is subjected to $\gamma$ correction; an analog/digital converter (hereinafter referred to as an A/D converter) 304 for converting the $\gamma$-corrected video signal in the form of an analog signal to data in the form of a digital signal in accordance with the control signal from the control signal generator 312; a selector 305 for successively outputting the digital signal to respective memories of a memory section 306 in turns in accordance with the control signal from the control signal generator 312; a red (R) memory 306R, a green (G) memory 306G and a blue (B) memory 306B all provided in the memory section 306 for storing data contained in a red wavelength region, a green wavelength region and a blue wavelength region, respectively; a digital/analog converter (hereinafter referred to as a D/A converter) 307 for converting the data stored in the memory section 306 from digital signals to analog signals in accordance with the control signal from the control signal generator 312, and comprising a D/A converter 307R corresponding to the R memory 306R, a D/A converter 307G corresponding to the G memory 306G and a D/A converter 307B corresponding to the B memory 306B; a synchronizing signal generator 313 for generating a predetermined synchronizing signal such as a horizontal synchronizing signal, which is required by a monitor (not shown), in accordance with the control signal from the control signal generator 312; a lamp 310 for emitting a beam of illumination light supplied to a location of which image is to be picked up by the CCD 301, or the like; a rotating filter 309 including three filters adapted to separate the illumination light from the lamp 310 into three beams corresponding to red, green and blue wavelength regions; a motor 311 adapted to rotate the rotating filter 309 in accordance with the control signal from the control signal generator 312; and a light guide 308 for introducing the aforesaid illumination light, separated into the respective wavelength regions, to a location of which image is to be picked up by the CCD 301, or the like.

The CCD 301 is connected to an input terminal of the amplifier 302, of which output terminal is in turn connected to an input terminal of the $\gamma$ circuit 303. The $\gamma$ circuit 303 has its output terminal connected to an input terminal of the A/D converter 304.

Input terminals of the R memory 306R, the G memory 306G and the B memory 306B are connected to respective output terminals of the selector 305. An output terminal of the R memory 306R is connected to both an input terminal of the D/A converter 307R and an input terminal of a scope image data compressing apparatus (hereinafter referred to as an image data compressing apparatus) 320 explained later. An output terminal of the G memory 306G is connected to both an input terminal of the D/A converter 307G and an input terminal of the image data compressing apparatus 320 explained later. An output terminal of the B memory 306B is connected to both an input terminal of the D/A converter 307B and an input terminal of the image data compressing apparatus 320 explained later.

An output of the D/A converter 307R is connected to a monitor (not shown) or the like through an output terminal 314R. An output of the D/A converter 307G is connected to the monitor (not shown) or the like through an output terminal 314G. An output of the D/A converter 307B is connected to the monitor (not shown) or the like through an output terminal 314B. An output of the synchronizing signal generator 313 is connected to the monitor (not shown) or the like through an output terminal 314S.

Control signal input terminals of the A/D converter 304, the selector 305, the memory section 306, the D/A converter 307, the motor 311 and the synchronizing signal generators 313 are connected to respective output terminals of the control signal generator 312. Furthermore, one output terminal of the control signal generator 312 is connected to an input terminal of the image data compressing apparatus 320 explained later.

The image data compressing apparatus 320 comprises an average color calculating section 321 for calculating an average color from the data in the memory section 306, and an image compressing section 322 for compressing the data from the average color calculating section 321.

An image recording section 323 is to record the data compressed by the image data compressing apparatus 320 by using a recording medium of large capacity such as an optical disk or an opto-magnetic disk.

Figure 29:
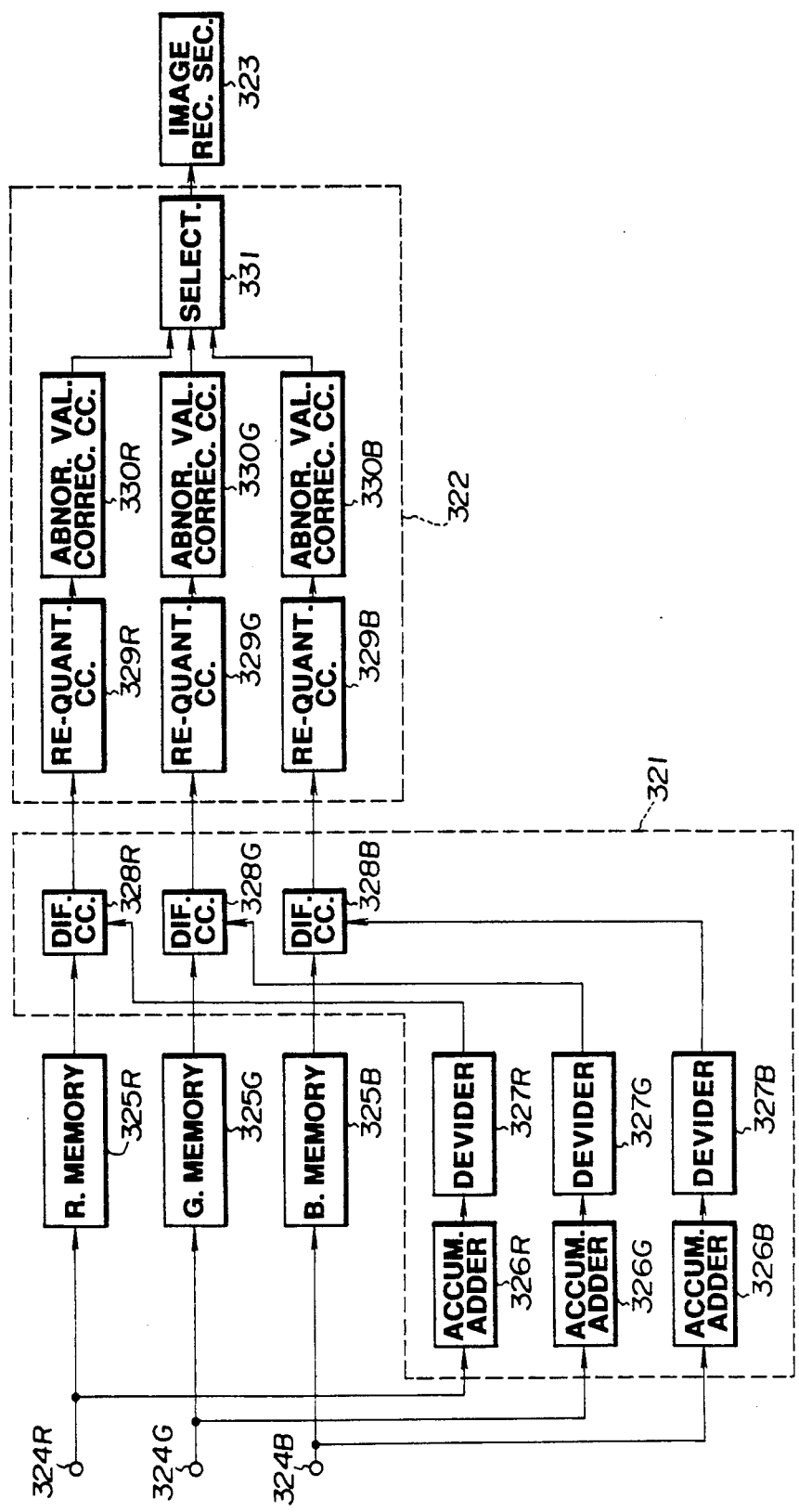

The image data compressing apparatus 320 includes, as shown in FIG. 29, an R memory 325R as a working memory to store the input data in the red wavelength region, a G memory 325G as a working memory to store the input data in the green wavelength region, and a B memory 325B as a working memory to store the input data in the blue wavelength region, in addition to the average color calculating section 321 and the image compressing section 322.

The average color calculating section 321 comprises an accumulating adder 326R for accumulatively adding the input data in the red color region, a divider 327R for dividing the accumulated data in the accumulating adder 326R by the predetermined number of pixels, a differential circuit 328R for calculating a difference between each data in the R memory 325R and the division result of the divider 327R, a similar set of an accumulating adder 326G, a divider 327G and a differential circuit 328G corresponding to the green color region, as well as another similar set of an accumulating adder 326B, a divider 327B and a differential circuit 328B corresponding to the blue color region.

The image compressing section 322 comprises a re-quantization circuit 329R for re-quantizing the data from the differential circuit 328R as the differential data in the red wavelength region, an abnormal value correction circuit 330R for correcting an abnormal value of the re-quantized data, a similar set of a re-quantization circuit 329G and an abnormal value correction circuit 330G corresponding to the green wavelength region, a similar set of a re-quantization circuit 329B and an abnormal value correction circuit 330B corresponding to the blue wavelength region, as well as a selector 331 successively changed over to deliver outputs of the abnormal value correction circuits 330R, 330G, 330B to the image recording section 323 in turns.

Input terminals of the R memory 325R and the accumulating adder 326R are both connected to the aforesaid input terminal 324R, input terminals of the G memory 325G and the accumulating adder 326G are both connected to the aforesaid input terminal 324G, and input terminals of the B memory 325B and the accumulating adder 326B are both connected to the aforesaid input terminal 324B, respectively.

An output terminal of the accumulating adder 326R is connected to an input terminal of the divider 327R, an output terminal of the accumulating adder 326G is connected to an input terminal of the divider 327G, and an output terminal of the accumulating adder 326B is connected to an input terminal of the divider 327B.

The differential circuit 328R has a first input terminal connected to an output terminal of the R memory 325R, and a second input terminal connected to an output terminal of the divider 327R. The differential circuit 328G has a first input terminal connected to an output terminal of the G memory 325G, and a second input terminal connected to an output terminal of the divider 327G. The differential circuit 328B has a first input terminal connected to an output terminal of the B memory 325B, and a second input terminal connected to an output terminal of the divider 327B.

An output terminal of the differential circuit 328R is connected to an input terminal of the re-quantization circuit 329R, and an output terminal of the re-quantization circuit 329R is in turn connected to an input terminal of the abnormal value correction circuit 330R. An output terminal of the differential circuit 328G is connected to an input terminal of the re-quantization circuit 329G, and an output terminal of the re-quantization circuit 329G is in turn connected to an input terminal of the abnormal value correction circuit 330G. An output terminal of the differential circuit 328B is connected to an input terminal of the re-quantization circuit 329B, and an output terminal of the re-quantization circuit 329B is in turn connected to an input terminal of the abnormal value correction circuit 330B.

The selector 331 has a first input terminal connected to an output terminal of the abnormal value correction circuit 330R, a second input terminal connected to an output terminal of the abnormal value correction circuit 330G, and a third input terminal connected to an output terminal of the abnormal value correction circuit 330B.

An output terminal of the selector 331 is connected to the image recording section 323.

Operation of the image data compressing apparatus thus constituted will be described below.

The rotating filter 309 is rotated by a motor 311 which is driven in synchronism with the control signal from the control signal generator 312, for separating the illumination light of the lamp 310 into three serial beams in the red, green and blue wavelength regions, as shown in FIG. 28. The three beams of illumination light separated into the respective wavelength regions are successively guided through the light guide 308 and then irradiated to the object.

The reflected light from the object under irradiation of the illumination light is focused by an objective lens system (not shown) on an image sensing surface of the CCD 301 and, after photoelectric conversion, a resultant image pick-up signal is input to the amplifier 302.

The amplifier 302 removes noises or the like away from the image pick-up signal to provide a video signal, which is amplified to a certain voltage range of 0–1V, for example, and then output to the γ circuit 303.

The γ circuit 303 shapes the video signal to have a gamma characteristic, followed by outputting it to the A/D converter 307.

The A/D converter 307 converts or quantize the video signal having a gamma characteristic to a digital signal of eight bits, for example, following by outputting the 8-bit digital signal to the selector 305.

The selector 305 outputs the digital signal to the respective memories of the memory section 306 in synchronism with the control signal from the control signal generator 312 in turns. Specifically, when the separated wave-length region of the illumination light passing through the rotating filter 309 is red, the digital signal is output to the R memory 306R. Likewise, the digital signal is output to the G memory 306G when the separated wavelength region is green, and to the B memory 306B when it is blue. In other words, the digital signal is input to and stored in the respective memories corresponding to the wavelength regions of the reflected light from the object.

The respective memories of the memory section 306 output the data stored therein to the D/A converter section 307 and the image data compressing apparatus 320 in accordance with the control signal from the control signal generator 312. On this occasion, the memories output the data, which are successively or serially applied through the selector 305, to the D/A converter section 307 at the same time or in parallel. In other words, three images of the reflected light from the object in the respective wave-length regions sensed successively are here given with simultaneity.

The D/A converter 307R of the D/A converter section 307 converts the data stored in the R memory 306R from the digital signal to an analog signal, followed by delivering the analog signal to the output terminal 314R. The D/A converter 307G converts the data stored in the G memory 306G from the digital signal to an analog signal, followed by delivering the analog signal to the output terminal 314G. The D/A converter 307B converts the data stored in the B memory 306B from the digital signal to an analog signal, followed by delivering the analog signal to the output terminal 314B.

Simultaneously, the synchronizing signal generator 313 generates the predetermined synchronizing signal such as a horizontal synchronizing signal, which is required by the monitor (not shown), in accordance with the control signal from the control signal generator 312, and then delivers the synchronizing signal to the output terminal 314S.

Based on the signals delivered to the output terminals 314R, 314G, 314B, 314S, the monitor (not shown) displays the object sensed by the CCD 301 in the form of a color image.

Further, the data stored in the R memory 306R of the memory section 306 is applied to the input terminal 324R of the image data compressing apparatus 320 in accordance with the control signal from the control signal generator 312, as shown in FIG. 29. Likewise, the data stored in the G memory 306G is applied to the input terminal 324G, and the data stored in the B memory 306B is applied to the input terminal 324B.

The data in the red wavelength region applied to the input terminal 324R is stored in the R memory 325R and also applied to the accumulating adder 326R.

The accumulating adder 326R accumulatively adds the applied data for one picture and delivers the total sum to the divider 327R, as mentioned above.

The divider 327R divides the total sum of the data for one picture applied from the accumulating adder 326R by the total number of pixels in one picture (e.g., 262,144 if the number of pixels is 512 in each of the vertical and horizontal directions), for calculating an average color R' in the red plane.

Likewise, the data in the green wavelength region applied to the input terminal 324G is stored in the G memory 325G, and an average color G' in the green plane is calculated by a combination of the accumulating adder 326G and the divider 327G. The data in the blue wavelength region applied to the input terminal 324B is stored in the B memory 325B, and an average color B' in the blue plane is calculated by a combination of the accumulating adder 326G and the divider 327G.

The average color R' calculated by the divider 327R is applied to the differential circuit 328R.

The differential circuit 328R subtracts the average value R' for one picture, which has been obtained by the divider 327R as mentioned above, from the respective data for one picture in the red wavelength region stored in the R memory 325R, followed by delivering the resultant differential data to the re-quantization circuit 329R.

The re-quantization circuit 329R re-quantizes the above differential data dependent on its value and delivers the re-quantized data to the abnormal value correction circuit 330R.

If the re-quantized data departs from a data range in which the data is recordable, the abnormal value correction circuit 330R corrects that data. For example, if the requantized data exceeds above an upper limit, the circuit 330R sets that data to an upper limit value, and if it exceeds below a lower limit, the circuit 330R sets that data to a lower limit value. As a result, the respective differential data thus converged into the data recordable range are output to the selector 331.

Likewise, the data for one picture in the green wavelength region are processed through the G memory 325G, the divider 327G, the differential circuit 328G, the re-quantization circuit 329G and the abnormal value correction circuit 330G to become the differential data converged into the data recordable range, which are then output to the selector 331. The data for one picture in the blue wavelength region are processed through the B memory 325B, the divider 327B, the differential circuit 328B, the requantization circuit 329B and the abnormal value correction circuit 330B to become the differential data converged into the data recordable range, which are then output to the selector 331.

The selector 331 successively delivers the differential data, which have been converged into the data recordable range as mentioned above, to the image recording section 323 as an image recording apparatus in the order of the red wavelength region, the green wavelength region and the blue wavelength region, for example.

The image recording section 323 records the input data in a recording medium of large capacity such as an optical disk or opto-magnetic disk.

Figure 30A:
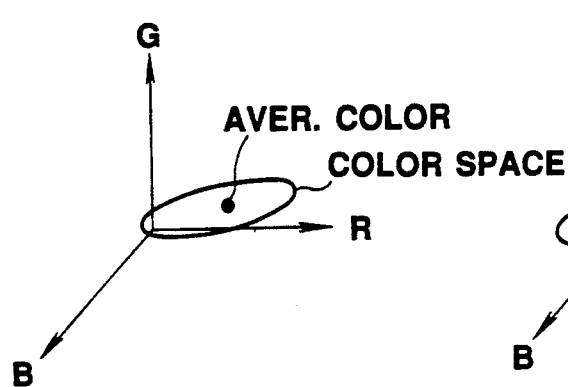
FIGS. 30a and 30b are a graphic representation for explaining coordination conversion using an average color.

The above mentioned data and average colors in the respective wavelength regions are three-dimensionally illustrated as shown in FIG. 30a, for example. When normally observing the body cavity, the video signal has a high-brightness level in the red wavelength region (R), while it has a low-brightness level in the green wavelength region (G) and the blue wavelength region (B), because a flesh color is predominated in the body cavity. Accordingly, a color space of the video signal has a substantially ellipsoidal shape oblongly extending from the low-brightness level in the green wavelength region (G) and the blue wavelength region (B) toward the high-brightness level in the red wavelength region (R). Thus, the coordinate of the average color of the video signal is also positioned offset toward the red wavelength region (R).

Figure 30B:
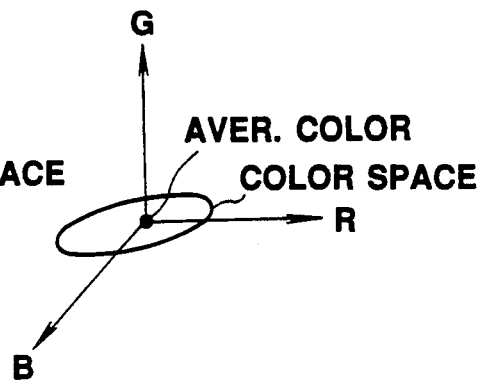

Furthermore, by taking the differences between the average color of the respective wavelength regions and the data of the video signal in the respective wavelength regions illustrated in FIG. 30a, as mentioned above, the average color of the video signal is now positioned at the origin of the coordinates as illustrated in FIG. 30b. In other words, the video signal is averagely distributed over the respective wavelength regions such that the aforesaid color space of the video signal is distributed about the average color locating at the origin of the coordinates. Thus, the data of the video signal result in ones having a color space suitable for re-quantization explained later.

Figure 31A:
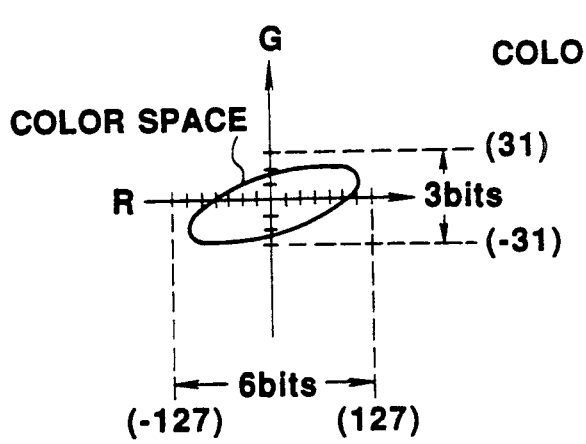
FIGS. 31a and 31b are a graphic representation for explaining re-quantization in the R-G color coordinate.
Figure 31B:
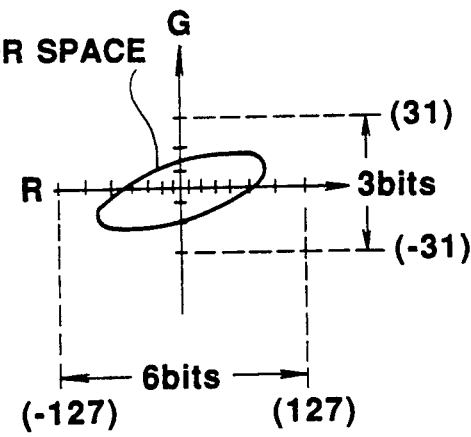

As mentioned before, the data of the video signal converted in color space are then re-quantized and recorded. At this time, the data are re-quantized into data coded with quantizing bits different from each other in the different signal ranges of the red wavelength region (R), the green wavelength region (G) and the blue wavelength region (B). To describe the re-quantization in connection with the red wavelength region (R) and the green wavelength region (G), as illustrated in FIG. 31a, the signal range of $-127 \sim 127$ in the red wavelength region (R) is quantized into codes of six bits and the signal range of $-31 \sim 31$ in the green wavelength region (G) is quantized into codes of three bits, for example. The signal range in the blue wavelength region (B) is quantized as with the green wavelength region (G). Moreover, while FIG. 31a illustrates linear quantization in which the signal range is evenly divided to make the foregoing re-quantization, the signal range may be subjected to non-linear quantization such that data are quantized densely in a range near the origin and more coarsely in ranges gradually remote from the origin, as shown in FIG. 31b.

Stated otherwise, taking into account the fact that the wavelength region of an observed image of the body cavity can be extremely limited, the quality of the recorded image can be improved by increasing a quantity of information of those signals in the red wavelength region which have their signal levels of wider range, and the compression ratio of the recorded image can be increased by reducing a quantity of information of those signals in the green and blue wavelength regions which have their signal levels of narrower range.

FIG. 32 shows a twelfth embodiment of the present invention. Note that similar components to those in the eleventh embodiment are denoted by the same reference characters and are not explained here.

In an electronic endoscope apparatus of the frame-sequentially imaging type of this embodiment, as shown in FIG. 32, the data in the R memory 306R, the G memory 306G and the B memory 306B are output, along with one control signal from the control signal generator 312, to a (scope) image data compressing apparatus 340 in accordance with another control signal from the control signal generator 312.

The image data compressing apparatus 340 includes a color space converting section 341, an average color calculating section 342 and an image compressing section 343, with the image recording section 323 connected to the image data compressing apparatus 340.

Figure 33:
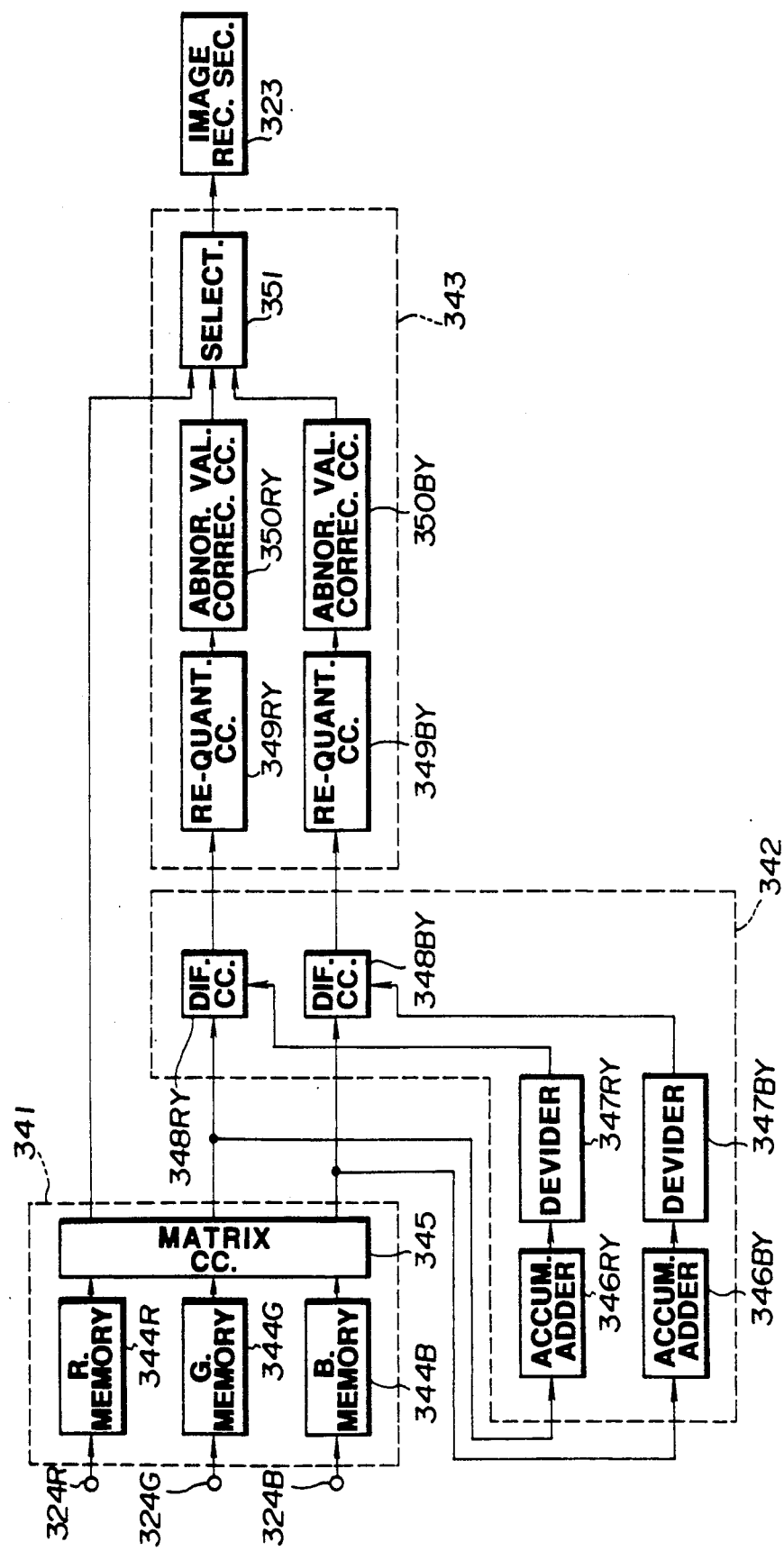

The color space converting section 341 of the image data compressing apparatus 340 comprises, as shown in FIG. 33, an R memory 344R as a working memory to store the input data in the red wavelength region, a G memory 344G as a working memory to store the input data in the green wavelength region, a B memory 344B as a working memory to store the input data in the blue wavelength region, and a matrix circuit 345 for converting the signals in the respective wavelength regions to both a brightness signal and color difference signals in conformity with the NTSC standards, for example.

The average color calculating section 342 comprises an accumulating adder 346RY for accumulatively adding the input data in a region of the color difference signal $R-Y$, a divider 347RY for dividing the accumulated data in the accumulating adder 346RY by the predetermined number of pixels, a differential circuit 348RY for calculating differences between the data in the R memory 344R and the division result of the divider 347RY, as well as a similar set of an accumulating adder 346BY, a divider 347BY and a differential circuit 348BY for a region of the color difference signal $B-Y$.

The image compressing section 343 comprises a re-quantization circuit 349RY for re-quantizing the data from the differential circuit 348RY as the differential data in the region of the color difference signal $R-Y$, an abnormal value correction circuit 350RY for correcting an abnormal value of the re-quantized data, a similar set of a re-quantization circuit 349BY and an abnormal value correction circuit 350BY for the region of the color difference signal $B-Y$, as well as a selector 351 successively changed over to deliver outputs of the abnormal value correction circuits 350RY, 350BY and the brightness signal Y of the matrix circuit 345 to the image recording section 323 in turns.

An input terminal of the R memory 344R is connected to the aforesaid input terminal 324R, an input terminal of the G memory 344G is connected to the aforesaid input terminal 324G, and an input terminal of the B memory 344B is connected to the aforesaid input terminal 324B, respectively.

An output terminal of the accumulating adder 346RY is connected to an input terminal of the divider 347RY, and an output terminal of the accumulating adder 346BY is connected to an input terminal of the divider 347BY.

The differential circuit 348RY has a first input terminal connected to an output terminal of the matrix circuit 345 for the color difference signal $R-Y$, and a second input terminal connected to an output terminal of the divider 347RY. The differential circuit 348BY has a first input terminal connected to an output terminal of the matrix circuit 345 for the color difference signal $B-Y$, and a second input terminal connected to an output terminal of the divider 347BY.

An output terminal of the differential circuit 348RY is connected to an input terminal of the re-quantization circuit 349RY, and an output terminal of the re-quantization circuit 349RY is in turn connected to an input terminal of the abnormal value correction circuit 350RY. An output terminal of the differential circuit 348BY is connected to an input terminal of the re-quantization circuit 349BY, and an output terminal of the re-quantization circuit 349BY is in turn connected to an input terminal of the abnormal value correction circuit 350GY.

The selector 351 has a first input terminal connected to an output terminal of the matrix circuit 345 for the brightness signal Y, a second input terminal connected to an output terminal of the abnormal value correction circuit 350RY, and a third input terminal connected to an output terminal of the abnormal value correction circuit 350BY.

An output terminal of the selector 351 is connected to the image recording section 323.

Operation of the image data compressing apparatus thus constituted will be described below.

As with the eleventh embodiment, the data stored in the R memory 306R of the memory section 306 shown in FIG. 32 is applied to the input terminal 324R of the image data compressing apparatus 340 in accordance with the control signal from the control signal generator 312, as shown in FIG. 33. Likewise, the data stored in the G memory 306G is applied to the input terminal 324G, and the data stored in the B memory 306B is applied to the input terminal 324B.

The data in the red wavelength region applied to the input terminal 324R is stored in the R memory 344R, the data in the green wavelength region applied to the input terminal 324G is stored in the G memory 344G, and the data in the blue wavelength region applied to the input terminal 324B is stored in the B memory 344B.

The matrix circuit 345 reads out the respective data stored in the R memory 344R, the G memory 344G and the B memory 344B for converting them to the brightness signal data Y and the color difference signal data R−Y, B−Y in conformity with the NTSC standards. The brightness signal Y is output to the selector 351, the color difference signal R−Y is output to both the accumulating adder 346RY and the differential circuit 348RY, and the color difference signal B−Y is output to both the accumulating adder 346BY and the differential circuit 348BY.

The accumulating adder 346RY accumulatively adds the applied data for one picture and delivers the total sum to the divider 347RY, as mentioned above.

The divider 347RV divides the total sum of the data for one picture applied from the accumulating adder 346RY by the total number of pixels in one picture (e.g., 262,144 if the number of pixels is 512 in each of the vertical and horizontal directions), for calculating an average color difference R−Y' of the color differences R−Y.

Likewise, an average color difference B−Y' of the color differences B−Y is calculated based on the aforesaid color difference signal data B−Y by a combination of the accumulating adder 346BY and the divider 347BY.

The differential circuit 348RY subtracts the average color difference R−Y' for one picture, which has been obtained by the divider 347RY as mentioned above, from each of the color difference signal data R−Y for one picture from the matrix circuit 345, followed by delivering the resultant differential data to the re-quantization circuit 349RY.

The re-quantization circuit 349RY re-quantizes the above differential data dependent on its value and delivers the re-quantized data to the abnormal value correction circuit 350RY.

If the re-quantized data departs from a data range in which the data is recordable, the abnormal value correction circuit 350RY corrects that data. For example, if the requantized data exceeds above an upper limit, the circuit 350RY sets that data to an upper limit value, and if it exceeds below a lower limit, the circuit 350RY sets that data to a lower limit value. As a result, the respective differential data thus converged into the data recordable range are output to the selector 351.

Likewise, the data for one picture in the green wavelength region are processed through the divider 347BY, the differential circuit 348BY, the re-quantization circuit 349BY and the abnormal value correction circuit 350BY to become the differential data converged into the data recordable range, which are then output to the selector 351.

The selector 351 successively delivers the brightness signal Y, the differential data of the color difference signal R−Y which have been converged into the data recordable range, and the differential data of the color difference signal B−Y which have been converged into the data recordable range, to the image recording section 323 as an image recording apparatus in the above order, for example.

The image recording section 323 records the input data in a recording medium of large capacity such as an optical disk or opto-magnetic disk.

Figure 34A:
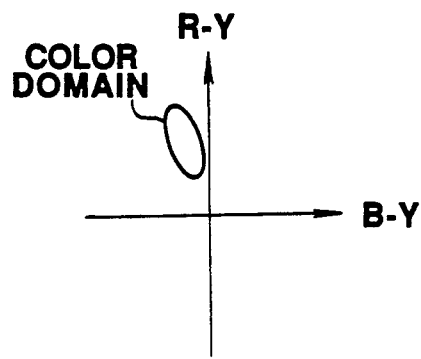
FIGS. 34a and 34b and 35a and 35b are graphic representations for explaining re-quantization for a color difference signal.

When normally observing the body cavity, a color domain of the foregoing color difference signals is plotted as shown in FIG. 34a by way of example. This is why the video signal has a high-brightness level in the red wavelength region (R), while it has a low-brightness level in the green wavelength region (G) and the blue wavelength region (B), because a flesh color is predominated in the body cavity. Accordingly, the color difference signal R−Y has a high signal level and the color difference signal B−Y has a low signal level such that the color domain of the color difference signals is located in the second quadrant in the form of an extremely limited elliptic area.

Figure 34B:
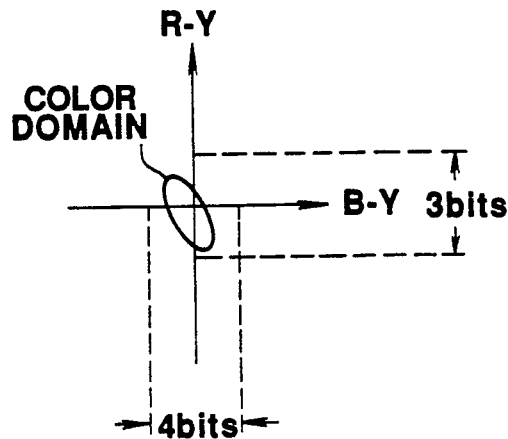

Furthermore, by taking the differences between the average color differences of the respective color difference signals and the respective color difference signal data of the video signal as explained in connection with FIG. 34a, as mentioned above, the color domain of the color differential signals is now positioned at the origin of the coordinates as illustrated in FIG. 34b. In other words, the color domain of the color difference signals is averagely distributed over the respective quadrants about the origin of the coordinates. Thus, the data of the color difference signals result in ones having a color domain suitable for re-quantization explained later.

As mentioned before, the data of the color difference signals converted in color domain are then re-quantized and recorded. At this time, the data are re-quantized into data coded with quantizing bits different from each other such that, for example, the color difference signal R−Y is quantized into codes of three bits and the color difference signal B−Y is quantized into codes of four bits.

Figure 35A:
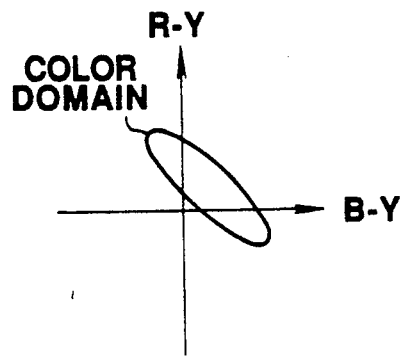

Meanwhile, when observing the body cavity or other object after dyeing same, a resultant color domain is plotted as shown in FIG. 35a by way of example. This is why the video signal has a low-brightness level in the red wavelength region (R), while it has a high-brightness level in the green wavelength region (G) and the blue wavelength region (B), because the body cavity or the like is dyed. Accordingly, both of the color difference signal R−Y and the color difference signal B−Y have a high signal level such that the color domain of the color difference signals has a substantially elliptic shape located mainly in the first quadrant and extending over the second and fourth quadrants.

Figure 35B:
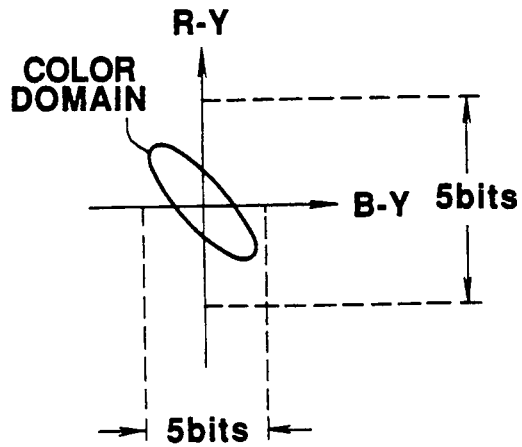

Furthermore, by taking the differences between the average color differences of the respective color difference signals and the respective color difference signal data of the video signal as explained in connection with FIG. 35a, as mentioned above, the color domain of the color differential signals is now positioned at the origin of the coordinates as illustrated in FIG. 35b. In other words, the color domain of the color difference signals is averagely distributed over the respective quadrants about the origin of the coordinates. Thus, the data of the color difference signals result in ones having a color domain suitable for re-quantization explained later.

As mentioned before, the data of the color difference signals converted in color domain are then re-quantized and recorded. At this time, the data are re-quantized such that the color difference signal R−Y and the color difference signal B−Y are both quantized into codes of five bits, for example.

Either the re-quantization in the case of normal observation or the re-quantization in the case of observation after dyeing is selectively carried out through an exchange switch (not shown), for example.

Thus, taking into account the fact that the region of each color differential signal derived from an observed image of the body cavity is extremely limited, the quality of the recorded image can be improved by recording the brightness signal without compressing it.

In addition, by changing the number of bits used for re-quantizing the data between the case of normal observation and the case of observation after dyeing, it is possible to increase the compression ratio in the case of normal observation and to improve the quality of the recorded image in the case of observation after dyeing.

Figure 36:
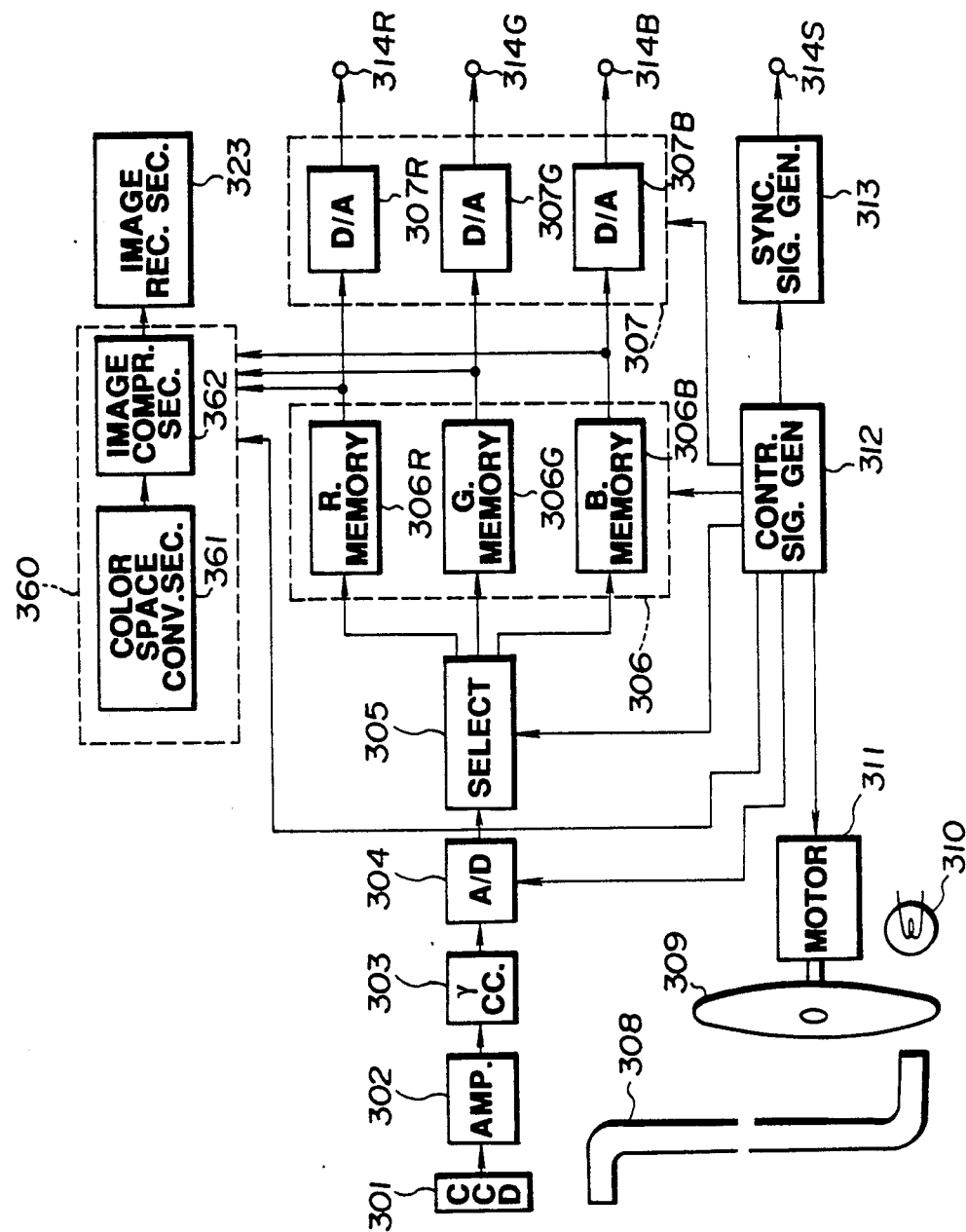

FIG. 36 shows a thirteenth embodiment of the present invention. Note that the same components as those in the eleventh embodiment are denoted by the same reference characters and are not explained here.

As shown in FIG. 36, the data in the R memory 306R, the G memory 306G and the B memory 306B are output, along with one control signal from the control signal generator 312, to a (scope) image data compressing apparatus 360 in accordance with another control signal from the control signal generator 312.

The image data compressing apparatus 360 includes a color space converting section 261 and an image compressing section 362, with the image recording section 323 connected to the image data compressing apparatus 360.

Figure 37:
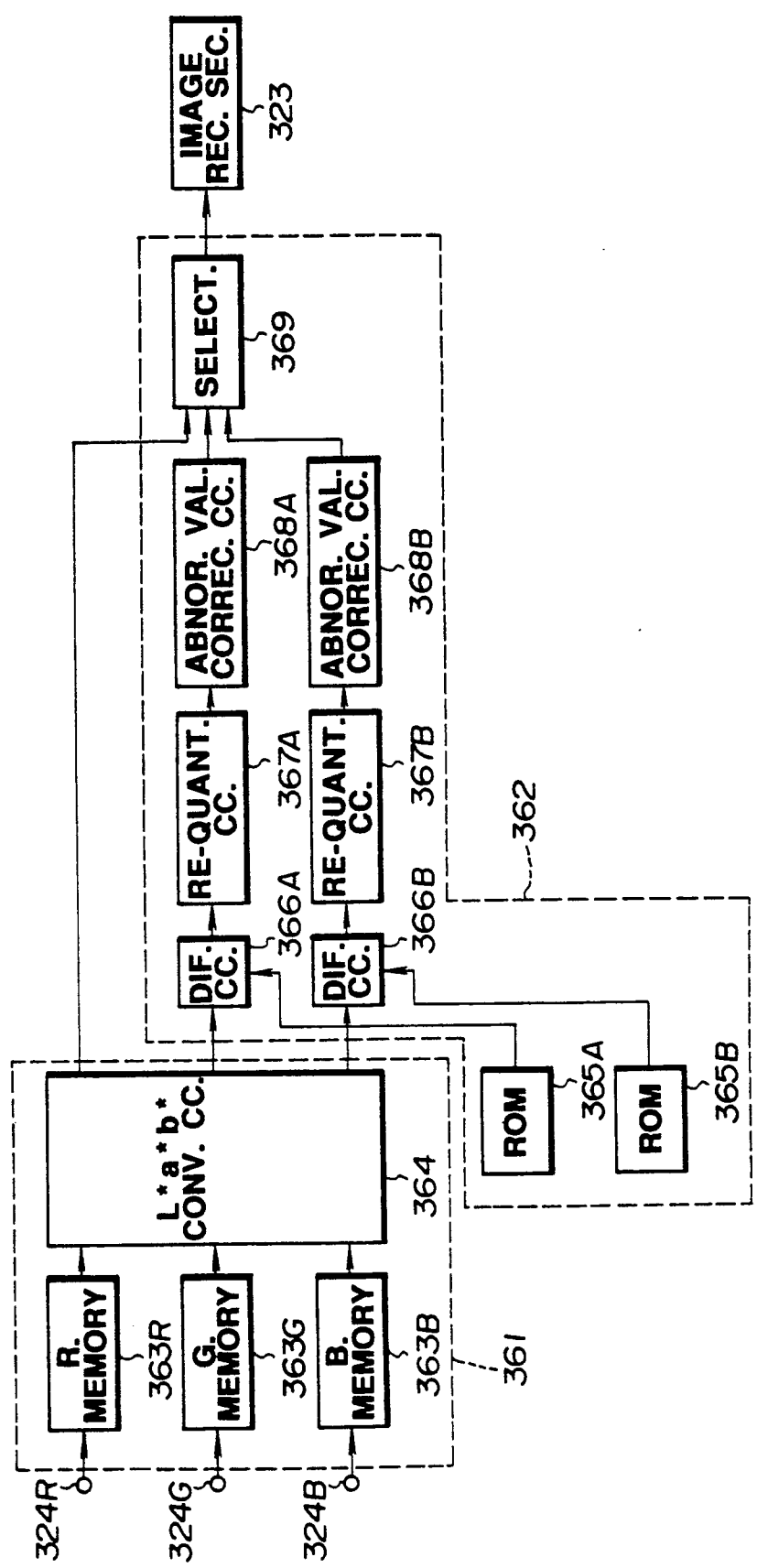

The color space converting section 361 of the image data compressing apparatus 360 comprises, as shown in FIG. 37, an R memory 363R as a working memory to store the input data in the red wavelength region, a G memory 363G as a working memory to store the input data in the green wavelength region, a B memory 363B as a working memory to store the input data in the blue wavelength region, and an L*a*b* conversion circuit 364 for converting the signals in the respective wavelength regions to signals in conformity with CIE1976 (L*, a*, b*) stipulations of CIE (International Commission on Illumination), for example.

The image compressing section 362 comprises an average color ROM 365A storing an average color a*′ for the color signal a* which has been calculated from distribution of the color signal a* of an image to be typically observed, for example, a differential circuit 366A for calculating a difference between the data in the region of the color signal a* applied from the L*a*b* conversion circuit 364 and the data stored in the average color ROM 365A, a re-quantization circuit 367A for re-quantizing the data from the differential circuit 366A as the differential data in the region of the color signal a*, an abnormal value correction circuit 368A for correcting an abnormal value of the re-quantized data, a similar set of an average color ROM 365B storing an average color b*′ for the color signal b* as with the case of the color signal a*, a differential circuit 366B, a re-quantization circuit 367B and an abnormal value correction circuit 368B, as well as a selector 369 successively changed over to deliver outputs of the abnormal value correction circuits 368A, 368B and the L*a*b* conversion circuit 364 to the image recording section 323 in turns.

An input terminal of the R memory 363R is connected to the aforesaid input terminal 324R, an input terminal of the G memory 363G is connected to the aforesaid input terminal 324G, and an input terminal of the B memory 363B is connected to the aforesaid input terminal 324B, respectively.

The differential circuit 366A has a first input terminal connected to an output terminal of the L*a*b* conversion circuit 364 for the color signal a*, and a second input terminal connected to the average color ROM 365A.

The differential circuit 366B has a first input terminal connected to an output terminal of the L*a*b* conversion circuit 364 for the color signal b*, and a second input terminal connected to the average color ROM 365B.

An output terminal of the differential circuit 366A is connected to an input terminal of the re-quantization circuit 367A, and an output terminal of the re-quantization circuit 367A is in turn connected to an input terminal of the abnormal value correction circuit 368A. An output terminal of the differential circuit 366B is connected to an input terminal of the re-quantization circuit 367B, and an output terminal of the re-quantization circuit 367B is in turn connected to an input terminal of the abnormal value correction circuit 368B.

The selector 369 has a first input terminal connected to an output terminal of the L*a*b* conversion circuit 364 for the brightness signal L*, a second input terminal connected to an output terminal of the abnormal value correction circuit 368A, and a third input terminal connected to an output terminal of the abnormal value correction circuit 368B.

An output terminal of the selector 369 is connected to the image recording section 323.

Operation of the image data compressing apparatus thus constituted will be described below.

As with the eleventh embodiment, the data stored in the R memory 306R of the memory section 306 shown in FIG. 36 is applied to the input terminal 324R of the image data compressing apparatus 360 in accordance with the control signal from the control signal generator 312, as shown in FIG. 37. Likewise, the data stored in the G memory 306G is applied to the input terminal 324G, and the data stored in the B memory 306B is applied to the input terminal 324B.

The data in the red wavelength region applied to the input terminal 324R is stored in the R memory 344R, the data in the green wavelength region applied to the input terminal 324G is stored in the G memory 344G, and the data in the blue wavelength region applied to the input terminal 324B is stored in the B memory 344B.

The L*a*b* conversion circuit 364 reads out the respective data stored in the R memory 363R, the G memory 363G and the B memory 363B for converting them to the brightness signal L* and the color signals a*, b* stipulated by CIE1976 (L*, a*, b*). The brightness signal L* is output to the selector 369, the color signal a* is output to the differential circuit 366A, and the color signal b* is output to the differential circuit 366B.

The differential circuit 366A subtracts the data of the average color a* out of the average color ROM 365A from each data of the color signal a* for one picture applied from the L*a*b* conversion circuit 364, followed by delivering the resultant differential data to the re-quantization circuit 367A.

The re-quantization circuit 367A re-quantizes the above differential data dependent on its value and delivers the re-quantized data to the abnormal value correction circuit 368A.

If the re-quantized data departs from a data range in which the data is recordable, the abnormal value correction circuit 368A corrects that data. For example, if the requantized data exceeds above an upper limit, the circuit 368A sets that data to an upper limit value, and if it exceeds below a lower limit, the circuit 368A sets that data to a lower limit value. As a result, the respective differential data thus converged into the data recordable range are output to the selector 369.

Likewise, the data of the color signal b* for one picture are processed through the differential circuit 366B, the re-quantization circuit 367B and the abnormal value correction circuit 368B to become the differential data converged into the data recordable range, which are then output to the selector 369.

The selector 369 successively delivers the brightness signal L*, the differential data of the color signal a* which have been converged into the data recordable range, and the differential data of the color signal b* which have been converged into the data recordable range, to the image recording section 323 as an image recording apparatus in the above order, for example.

The image recording section 323 records the input data in a recording medium of large capacity such as an optical disk or opto-magnetic disk.

As a modification, it is possible to provide plural average color ROM's for each color signal and to exchange them, as required, dependent on different observing methods inclusive of observation after dyeing, different locations to be observed, and others.

Furthermore, although the above embodiment has been explained as using the L*a*b* uniform color space, any other type of color space may also be used.

Thus, taking into account the fact that the region of each color signal derived from an observed image of the body cavity is extremely limited, the quality of the recorded image can be improved by recording the brightness signal without compressing it.

Moreover, although the above explanation has been made by referring to the electronic endoscope apparatus of the frame-sequentially imaging type, a composite video signal may be applied by providing means to decode the composite video signal at the stage prior to the input terminal of the video signal for each wavelength region, as an alternative example.

In addition, the above embodiment may be applied to a video processor apparatus connected to a TV camera of the externally mounting type which is attachable to an endoscope using an image guide.

With the foregoing eleventh through thirteenth embodiments, by calculating an average color of the observed image and making such conversion as to shift the image data to be positioned about the average color, most of the image data can be distributed in the vicinity of the average value. It is therefore possible to express the respective image data in the reduced number of bits and hence to increase the number of image frames recordable.

Next, there will be described embodiments in which image data are compressed by utilizing colorant density.

Figure 38:
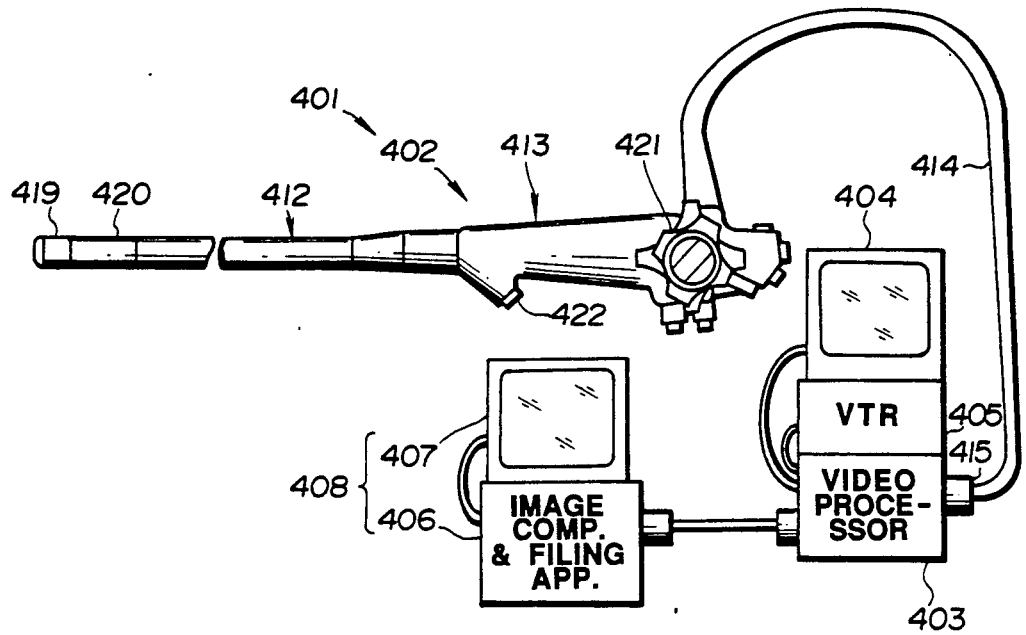

An endoscope system 401 of a fourteenth embodiment comprises, as shown in FIG. 38, an electronic endoscope 402 provided with image sensing means, a video processor 403 for supplying a beam of illumination light to the electronic endoscope 402 and carrying out signal processing, a TV monitor 404 for displaying a video signal resulted through the signal processing in the video processor 403, a VTR (video tape recorder) 405 for recording the video signal, an (scope) image compressing & filing apparatus 406 for compressing an endoscope image signal from the video processor 403, and a TV monitor 407 for displaying an endoscope image obtained by the image compressing & filing apparatus 406.

The electronic endoscope 402, the video processor 403, the TV monitor 404 and the VTR 405 jointly constitute an endoscope apparatus, while the image compressing & filing apparatus 406 and the TV monitor 407 jointly constitute a scope image compressing apparatus 408.

The electronic endoscope 402 includes an elongate insert section 412 which is flexible, for example, and a larger-diameter operating section 413 continuously provided at the rear end of the insert section 412. A flexible universal cord 414 is extended laterally from the rear end of the operating section 413, and a connector 415 is provided at the rear end of the universal cable 414. The electronic endoscope 402 is connectable through the connector 415 to the video processor 403 which incorporates a light source section and a video signal processing section therein. Further, the TV monitor 404 as display means is connected to the video processor 403.

On the front end side of the insert section 412, there are provided a hard distal end portion 419 and a bendable portion 420 contiguously provided behind the distal end portion 420, in this order from the front end. By rotating a bending operation knob 421 provided in the operating section 413, the bendable portion 420 can be bent in the horizontal or vertical direction. Further, the operating section 413 is formed with an insertion opening 422 which is communicated with an appliance channel provided through the insert section 412.

Figure 40:
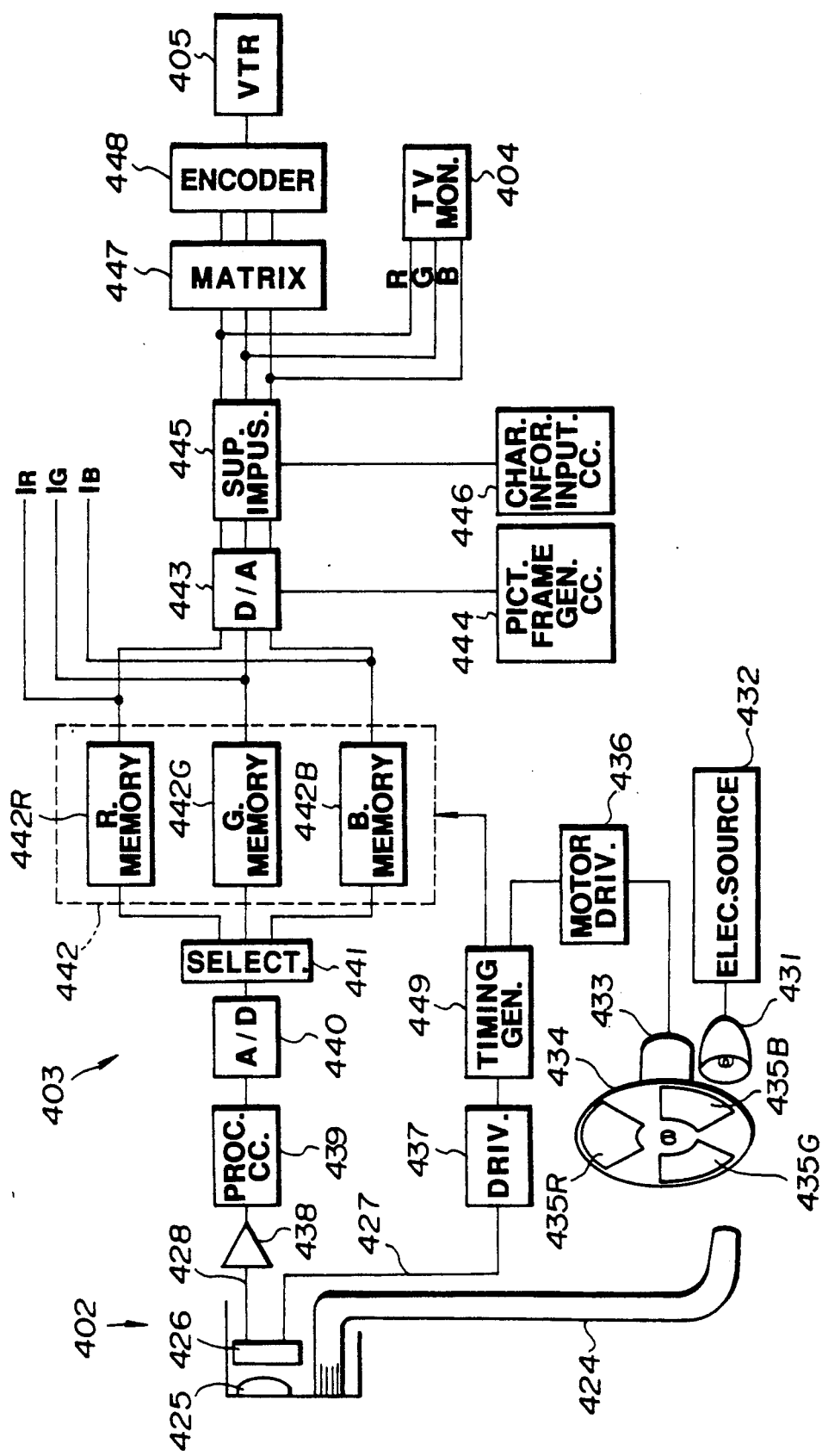

As shown in FIG. 40, a light guide 424 for transmitting the illumination light is extended through the insert section 412 of the electronic endoscope 402. The emergent end face of the light guide 424 is disposed in the distal end portion 419 of the insert section 412, allowing the illumination light to be emitted from the distal end portion 419. The incident end face of the light guide 424 is extended through the universal cord 414 for connection to the connector 415. In the distal end portion 419 of the insert section 412, there is also provided an objective lens system 425. A solid imaging device 426 is disposed at a focus position of the objective lens system 425. The solid imaging device 426 is sensitive to light over a wide wavelength region ranging from the ultraviolet band to the infrared band inclusive of the visible band.

Connected to the solid imaging device 426 are signal lines 427, 428 which are extended through the insert section 412 and the universal cord 414 for connection to the connector 415.

On the other hand, the video processor 403 includes a lamp 431 which is able to emit the beam of illumination light over a wide band ranging from a ultraviolet ray to an infrared ray. A conventional xenon lamp, stroboscopic lamp or the like can be used as the lamp 431. The xenon lamp or stroboscopic lamp emits not only a visible ray, not only ultrasonic and infrared rays in a large amount. Electric power is supplied from an electric source 432 to the lamp 431. Disposed in front of the lamp 431 is a rotating filter 434 which is driven by a motor 433 to rotate. The rotating filter 434 has color transmission filters 435R, 435G, 435B mounted to arrange in the circumferential direction with equal angular distances and capable of passing beams of red (R), green (G) and blue (B) light therethrough for normal observation, respectively.

The motor 433 is driven to rotate under control of a motor driver 436.

The light having passed through the rotating filter 434 enters the incident end face of the light guide 424, led through the light guide 424 to the distal end portion 419 of the insert section 412, and then emitted from the distal end portion 419 for illuminating a location to be observed.

The light returned from the observed location reflecting the illumination light is focused by the objective lens system 425 on the solid imaging device 426 for photoelectric conversion. Drive pulses from a driver 437 in the video processor 403 are applied to the solid imaging device 426 through the signal line 427 so that the video signal is read out and transferred in accordance with the drive pulses. The video signal read out of the solid imaging device 426 is applied through the signal line 428 to a preamplifier 438 provided in the video processor 403 or the electronic endoscope 402. The video signal having been amplified by the preamplifier 438 is applied to a processing circuit 439 to undergo signal processing, e.g., $\gamma$ correction and carrier removal, such that the halation area is processed to have a knee characteristic and the dark area is processed to have a bias of pedestal level. Afterward, the processed analog signal is converted to a digital signal. This digital video signal is selectively stored through a selector 441 into three memories corresponding to red (R), green (G) and blue (B) colors, i.e., an R memory 442R, a G memory 442G and B memories 442B, for example. The digital signals stored in the memories 442R, 442G, 442B, jointly constituting a memory circuit 442, are read out at the same time and then converted analog signals by a D/A converter 443 to be delivered as R, G, B color signals.

Meanwhile, the analog signals output from the D/A converter 443 are masked partially (in peripheral edges) in accordance with a control signal from a picture frame generator circuit 444, which is designed to generate a picture frame for display, in order to be converted to color signals for displaying a picture within the display frame, followed by being delivered to a superimposer 445. In the superimposer 445, the patent data applied from a character information inputting circuit 446 is superimposed on the image information.

The video signals thus added with the frame for display and the character information such as the patient information are delivered as R, G, B color signals for being displayed on the TV monitor 404.

The R, G, B color signals are separated or rearranged by a matrix circuit 447 into color difference signals and a brightness signal, which are converted to NTSC signals by an encoder 448 for encoding input signals in conformity with NTSC standards, followed by being recorded in the VTR 405.

The synchronous timing relationship between the respective circuits is kept using a synchronizing signal generated from a timing generator 449.

Figure 39:
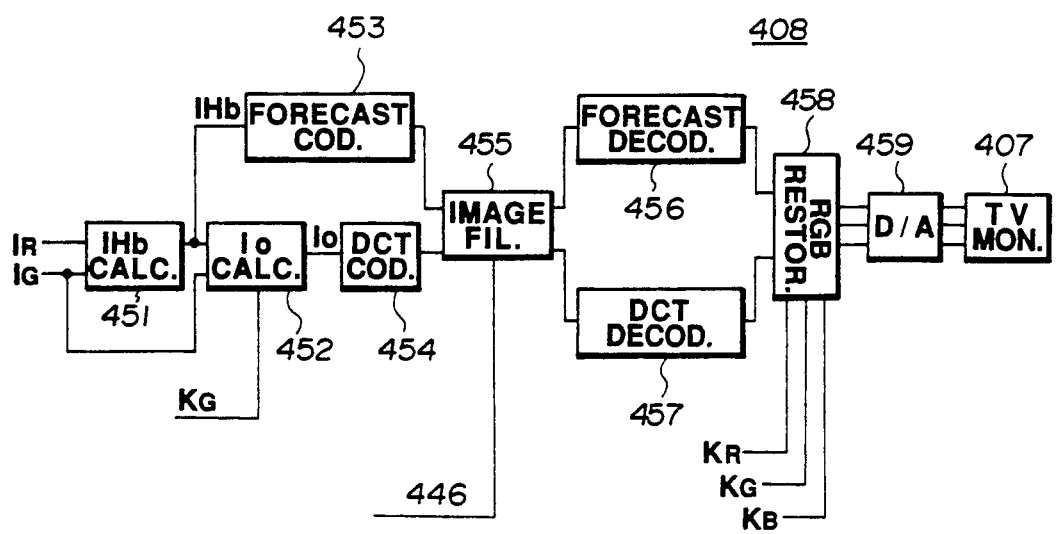

Outputs of the R memory 42R for storing the R image and the G memory 442G for storing the G image in the memory circuit 442 are applied a hemoglobin calculator (hereinafter referred to as an IHb calculator) 451 in the scope image compressing apparatus 408, as shown in FIG. 39.

Here, endoscope images have a feature that the image is mostly dominated by a red tone.

Figure 41:
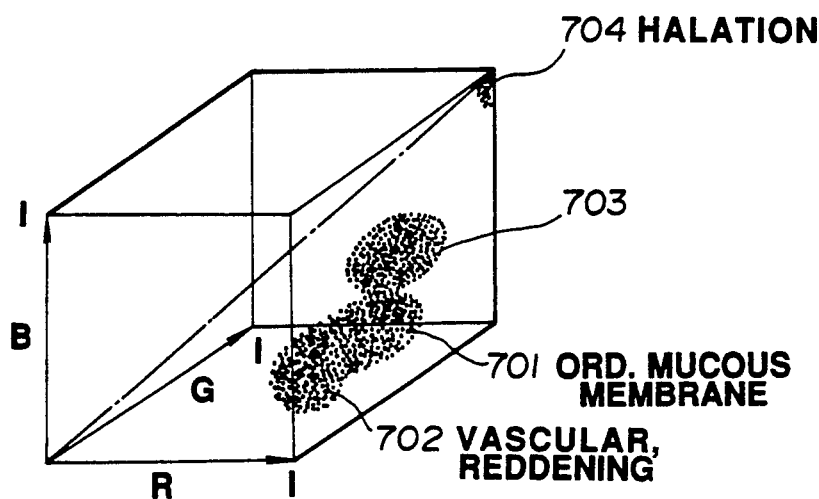
Figure 42:
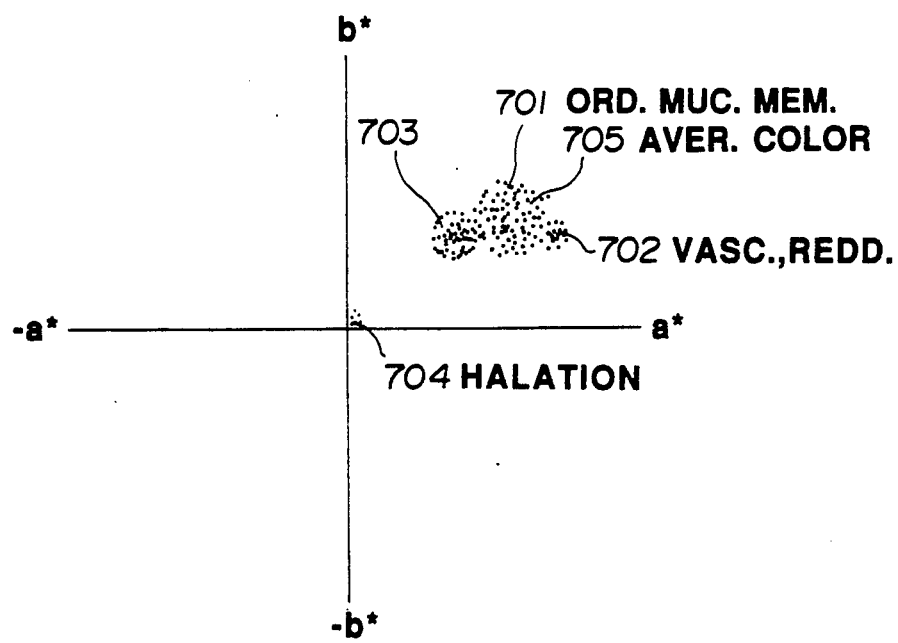

Color distribution of the endoscope image is illustrated in FIGS. 41 and 42.

FIGS. 41 and 42 are explained in Japanese Patent Laid-Open No. 63-173182(1988) in detail. FIG. 41 shows one example of distribution of the endoscope image data over an R, G, B space. FIG. 42 shows the same data converted to the coordinates of a uniform color space in conformity with CIE 1976 L*a*b* (CIE-LAB).

Examining color distribution of the endoscope image over the chromaticity coordinates, it will be found from FIG. 42 that vascular tracts and reddenings 702, white hepatics 703 and the like are distributed near a distribution area of ordinary mucous membranes 701 in a flesh color virtually as a background color, and the endoscope image is made up by colors in extremely narrow regions. To review the distribution diagram of FIG. 42 in more detail, it is generally understood that as compared with the color of the ordinary mucous membranes 701, the white hepatics 703 are high in luminosity but low in chroma, whereas the vasculars and reddenings 702 are high in chroma but low in luminosity. No substantial difference is found in hue therebetween in many cases. However, there is a tendency that the ordinary mucous membranes 701 is somewhat more yellowish than the vasculars and reddenings 702. Incidentally, the numeral 705 in FIG. 42 denotes an average color.

As described above, the color tone of the endoscope image is distributed in a considerably limited range as compared with general natural pictures.

The reason is in that most of colorants which determine various color tones of mucous membranes of a living body are hemoglobin as colorants contained in blood.

Figure 43A:
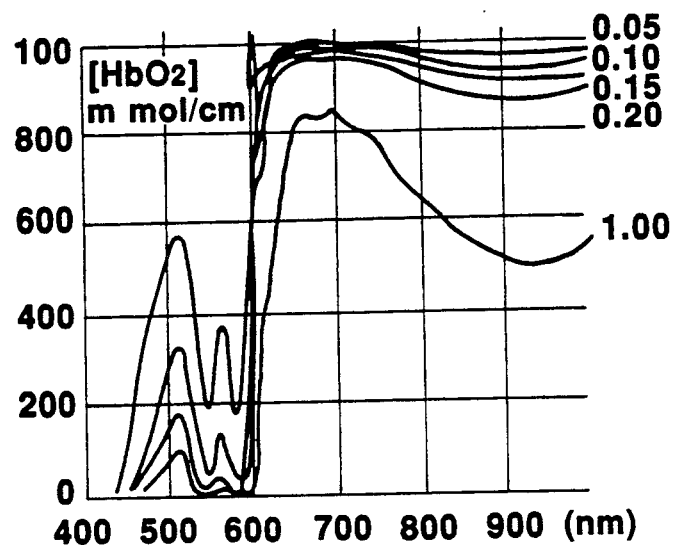
FIGS. 43a and 43b are characteristic graphs showing spectral transmissivity and absorbance of oxyhemoglobin, respectively.

FIG. 43a shows spectral transmissivity of oxyhemoglobin dominating a great part of colorants in mucous membranes of a living body.

Figure 43B:
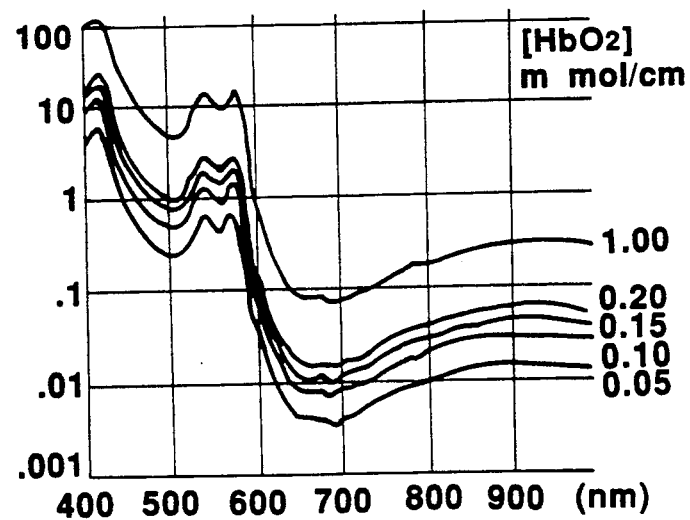

The graph of FIG. 43a can be converted to a graph of spectral absorbance as shown in FIG. 43b according to the law of Beer.

Now, in order to represent R, G, B images a hemoglopin index IHb which indicates an amount of hemoglobin, the intensities $I_R$, $I_G$, $I_B$ of the R, G, B image data are first expressed below;

$$I_R = I_{OR} \cdot RHb \qquad (1)$$

$$I_G = I_{OG} \cdot GHb \qquad (2)$$

$$I_B = I_{OB} \cdot BHb \qquad (3)$$

where $I_{OR}$, $I_{OG}$, $I_{OB}$ stand for the intensity of illumination light in the R, G, B wavelength regions and RHb, GHb, BHb stand for the transmissivity of hemoglobin (IHb) in the R, G, B wavelength regions, respectively.

Under a condition that the R, G, B beams of illumination light are balanced, the relationship of;

$$I_{OR} = I_{OG} = I_{OB} = I_O \qquad (4)$$

is established. Here, $I_O$ stands for the intensity of illumination light at the time when the respective color beams of illumination light are balanced.

Based on the law of Beer, the other two transmissivities RHb, BHb can be expressed below using one transmissivity GHb;

$$\log RHb = C_R \log GHb \qquad (5)$$

$$\log BHb = C_B \log GHb \qquad (6)$$

where $C_R$, $C_B$ are coefficients of the relationships between log GHb and log RHb and between log GHb and log BHb, respectively, which are determined from spectral characteristics.

The equation (5) can be rewritten as follows using an exponent:

$$RHb = (GHb)^{C_R} \qquad (7)$$

Likewise, the equation (6) can be rewritten to:

$$BHb = (GHb)^{C_B} \qquad (8)$$

Putting the equations (7), (8) and (4) into the equations (1), (2) and (3) results in:

$$I_R = I_O (GHb)^{C_R} \qquad (9)$$

$$I_G = I_O \cdot GHb \qquad (10)$$

$$I_B = I_O (GHb)^{C_B} \qquad (11)$$

Then, the amount of hemoglobin is calculated using the equations (1), (2) and (3). The index indicating the amount of hemoglobin is expressed below:

$$\begin{aligned} IHb &= \log I_R - \log I_G \\ &= \log(I_{OR} \cdot RHb) - \log(I_{OG} \cdot GHb) \\ &= \log RHb - \log GHb + \log I_{OR} - \log I_{OG} \end{aligned}$$

Here, since $I_{OR} = I_{OG}$ holds in approximation, the above equation can be turned to:

$$IHb = \log RHb - \log GHb \qquad (12)$$

Putting the equation (5) into the equation (12) results in:

$$\begin{aligned} IHb &= \log RHb - \log GHb \\ &= C_R \log GHb - \log GHb \\ &= (C_R - 1) \log GHb \end{aligned}$$

Therefore, the following equation is obtained:

$$GHb = 10^{IHb/(C_R - 1)} \qquad (13)$$

Putting the equation (13) into the equations (9), (10) and (11) results in:

$$\begin{aligned} I_R &= I_O \cdot RHb \\ &= I_O \cdot 10^{IHb \, C_R/(C_R - 1)} \end{aligned} \qquad (14)$$

$$\begin{aligned} I_G &= I_O \cdot GHb \\ &= I_O \cdot 10^{IHb/(C_R - 1)} \end{aligned} \qquad (15)$$

$$\begin{aligned} I_B &= I_O \cdot BHb \\ &= I_O \cdot 10^{IHb \, C_B/(C_R - 1)} \end{aligned} \qquad (16)$$

By substitution of $K_R = C_R/(C_R - 1)$, $K_G = 1/(C_R - 1)$ and $K_B = C_B/(C_R - 1)$, the equations (14), (15) and (16) are rewritten as follows, respectively:

$$I_R = I_O \cdot 10^{IHb \, K_R} \qquad (17)$$

$$I_G = I_O \cdot 10^{IHb \, K_G} \qquad (18)$$

$$I_B = I_O \cdot 10^{IHb \, K_B} \qquad (19)$$

From the equation (18):

$$I_O = I_G / 10^{IHb \, K_G} \qquad (20)$$

Besides, from the equations (5) and (6):

$$C_R = \log RHb / \log GHb$$

$$C_B = \log BHb / \log GHb.$$

Because $C_R$ and $C_B$ are calculated as constant values from FIG. 43 without depending on the density of hemoglobin, $K_R$, $K_G$ and $K_B$ can set in advance using respective constant values.

As will be seen from the equations (17), (18) and (19), the R, G, B images can be reproduced if the colorant density given by IHb and a level of the illumination light are both determined.

In view of the above, as shown in FIG. 39, the image signal data $I_R$, $I_G$ respectively output from the memories 442R, 442B are applied to the IHb calculator 451 for performing the arithmetic process of the equation (12). The resultant value is applied to both an $I_O$ calculator 452 and a forecast coder 453.

In the $I_O$ calculator 452, the arithmetic process of the equation (20) is performed to calculate $I_O$ from IHb, $K_G$ and $I_O$.

Since the IHb image representing the information such as vascular tracts, white hepatics and reddenings includes the high-frequency component to a substantial extent, it is subjected in the forecast coder 453 to forecast coding with a high compression effect.

On the other hand, the $I_O$ image output from the $I_O$ calculator 452 and hardly including the high-frequency component are applied to a DCT (discrete cosine transform) coder 454, which makes coding in accordance with the DCT method at a high compression ratio, for being subjected to image compression at such a high compression ratio.

The image signals respectively compressed in the forecast coder 453 and the DCT coder 454 are stored in an image filing apparatus 455 along with the patient data from the character information inputting circuit 446.

When reproducing the image data stored in the image filing apparatus 455, the IHb and $I_O$ images compressed in different manners are read out of the image filing apparatus 455 and decoded by respective decoders. Specifically, the IHb image is decoded by a forecast decoder 456, while the $I_O$ image is decoded by a DCT decoder 457. The decoded signals are both restored by an RGB restoring circuit 458 to RGB image signals on the basis of the equations (17), (18) and (19).

The image data restored by the RGB restoring circuit 458 are converted to analog signals by a D/A converter 459 and then displayed on the TV monitor 407.

With this fourteenth embodiment, by separating the RGB image data into the distribution image of hemoglobin and the image of illumination light based on spectral characteristics of colorants in a living body as a feature of the endoscope image, and then applying the optimum compression techniques to the respective images, it is possible to provide a compression method which is suitable for the endoscope image and also ensures high efficiency and high image quality.

Figure 44:
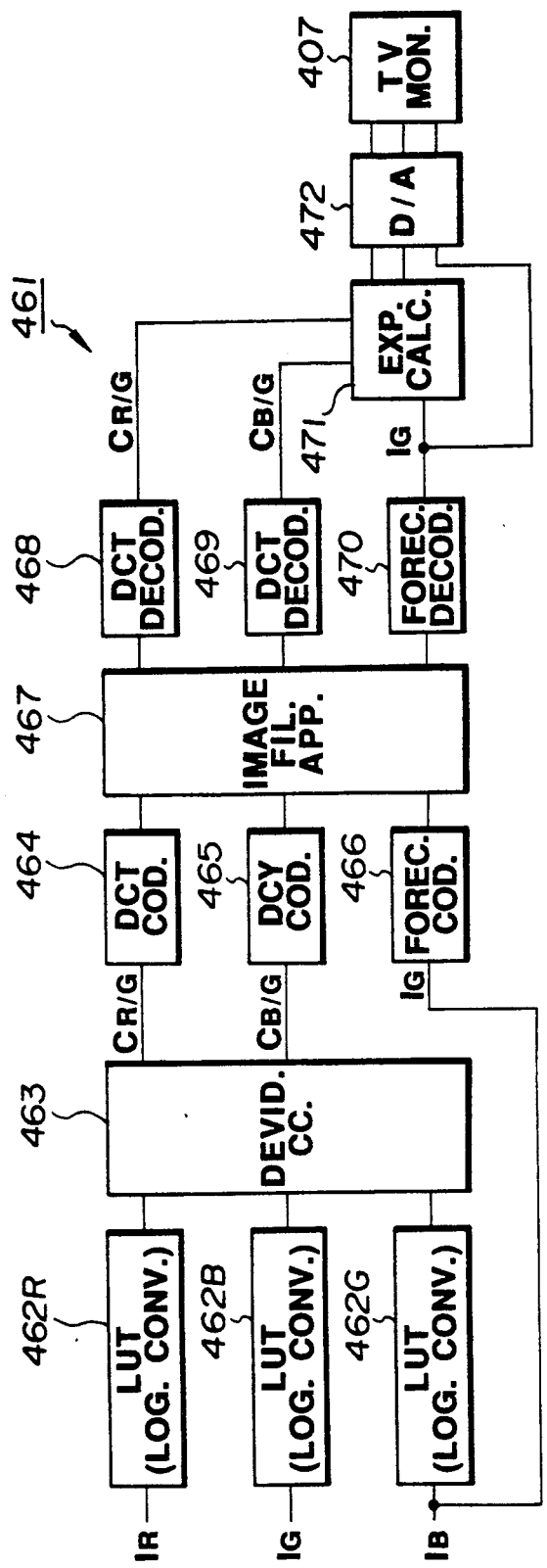

FIG. 44 shows an endoscope image compressing apparatus 461 according to a fifteenth embodiment of the present invention.

Figure 45A:
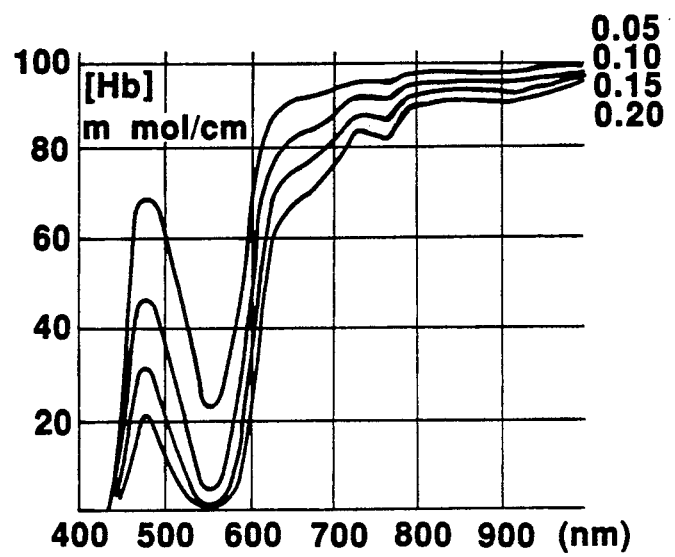
FIGS. 45a and 45b are characteristic graphs showing spectral transmissivity and absorbance of deoxyhemoglobin, respectively.
Figure 45B:
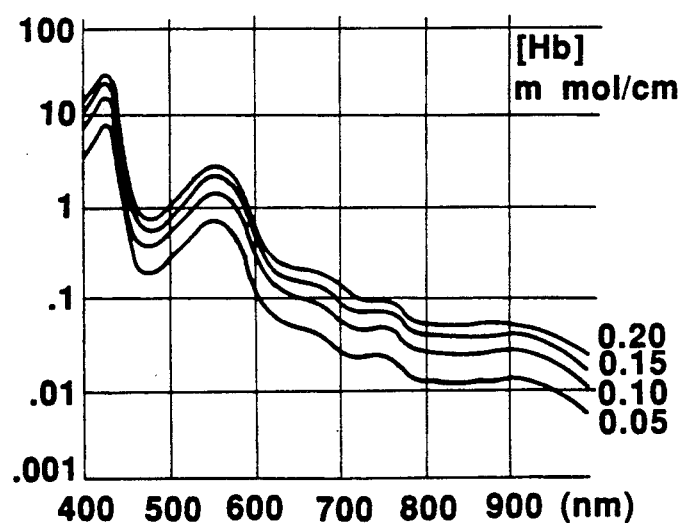

Hemoglobin dominates a large part of colorants present in a living body. FIGS. 45a and 45b show one example of spectral transmissivity and absorbance of deoxyhemoglobin, respectively. However, the spectral characteristic of hemoglobin is varied dependent on a degree of oxidization, and other colorants such as cytochrome and myoglobin are also present in addition to hemoglobin. For the reason, estimation based on a single spectral characteristic entails an error to some extent.

In view of the above, this fifteenth embodiment is intended to perform compression of an endoscope image while ensuring high efficiency and high image quality, by employing the density of colorants in a living body and features of spectral characteristics.

The R, G, B image data $I_R$, $I_G$, $I_B$ output from the memories 442R, 442G, 442B, which constitute the memory circuit 442 of the video processor 403 shown in FIG. 40, are applied to look-up table circuits (hereinafter referred to as LUT circuits) 462R, 462G, 462B constituting a part of a scope image compressing apparatus 461 shown in FIG. 44, respectively.

The LUT circuits 462R, 462G, 462B are each designed to make log conversion of an input signal by using data previously written therein as output data of the log conversion. Thus, the applied R, G, B image data are output from the LUT circuits 462R, 462G, 462B after being subjected to the log conversion, respectively.

The R, G, B image data log-converted by the LUT circuits 462R, 462G, 462B are applied to a divider circuit 463 where ratios C(R/G), C(B/G) of the R and B image data to the G image data are calculated.

While hemoglobin dominates most of colorants in mucous membranes of a living body, the ratio of absorbances of hemoglobin at the respective wavelengths is constant. This is equally applied to the other colorants. Accordingly, even in those images which include colorants other than hemoglobin, the above log ratios are not so varied and have certain constant values in many cases. Therefore, the foregoing step provides the preprocessing suitable for an effective compression method. The two R and B image data are expressed as follows by using data calculated from the log ratios between RGB data as well as the G image data.

Given the log ratio of the R image data to the G image data being C(R/G) and the log ratio of the B image data to the G image data being C(B/G) by definition, the following equations are obtained:

$$\log I_R / \log I_G = C(R/G) \quad (21)$$

$$\log I_B / \log I_G = C(B/G) \quad (21).$$

From the equation (21):

$$\log I_R = C(R/G) \cdot \log I_G$$
$$= \log I_G^{C(R/G)}$$

Using an exponent, the above equation can be rewritten to:

$$I_R = (I_G)^{C(R/G)} \quad (23).$$

Likewise, from the equation (22):

$$I_B = (I_G)^{C(B/G)} \quad (24).$$

Accordingly:

$$I_R = (I_G)^{C(R/G)} \quad (23)$$

$$I_G = I_G) \quad (25)$$

$$I_B = (I_G)^{C(B/G)} \quad (24).$$

Thus, the R, G, B image data $I_R$, $I_G$, $I_B$ can be converted data expressed using $I_G$, C(R/G) and C(B/G).

In view of the above, the divider circuit 463 shown in FIG. 44 performs the arithmetic processes of the equations (21), (22). The log ratios C(R/G), C(B/G) obtained by the divider circuit 463 and less fluctuated in their values are compressed by DCT coders 464, 465 with the DCT coding technique, respectively. As to the G image which is likely to yield at proper exposure, the $I_G$ image data is applied to a forecast coder 466 for direct forecast coding.

The image signals coded by the DCT coders 464, 465 and the forecast coder 466 are recorded in an image filing apparatus 467.

Of the image data recorded in the image filing apparatus 467, the image data given by the log ratios C(R/G) and C(B/G) are decoded by DCT decoders 468, 469, respectively, and the G image data is decoded by a forecast decoder 470.

The respective image data decoded by the DCT decoders 468, 469 and the forecast decoder 470 are applied to an exponent calculator 471 for being converted based on the equations (23), (24) to R, B image data. These R, B data are then applied, along with the G image data, to a D/A converter 472 for conversion to analog signals, followed by being displayed on the TV monitor 407.

With this fifteenth embodiment, even when the spectral characteristic is varied dependent on a degree of oxidization of hemoglobin, or other colorants than hemoglobin are also present, it is possible to perform the image compression which ensures high image quality, has high efficiency and is hence suitable for the endoscope image, by making use of spectral characteristics of colorants in a living body, as characteristics of the endoscope image, to convert and compress the image data.

Note that image sensing means for producing the endoscope image is not limited to the electronic endoscope 402, it may be provided by mounting a TV camera to an eyepiece portion of a fiberscope.

In the above embodiment, the signals picked up by the electronic endoscope 402 are input to the scope image compressing & filing apparatus 408 and the like through the video processor 403. It is however apparent that the foregoing image compression is also applicable to the endoscope images already recorded in a scope image filing apparatus, VTR and so forth.

Further, although the image conversion has been performed on the R, G, B images, the wavelength regions of the converted images may be divided in a different manner dependent on cases.

In short, the scope image compressing apparatus in the fourteenth and fifteenth embodiments is featured in comprising compression means to make image conversion of the endoscope component images of the respective wavelength regions based on the colorant density and to optimaly compress the resultant image information individually.

According to the fourteenth and fifteenth embodiments as mentioned above, since the endoscope images separated into the respective wavelength regions by color separating means are converted to image data based on the density of a colorant, and the image data thus converted are then compressed, it is possible to achieve the image compression at high efficiency.

Figure 46:
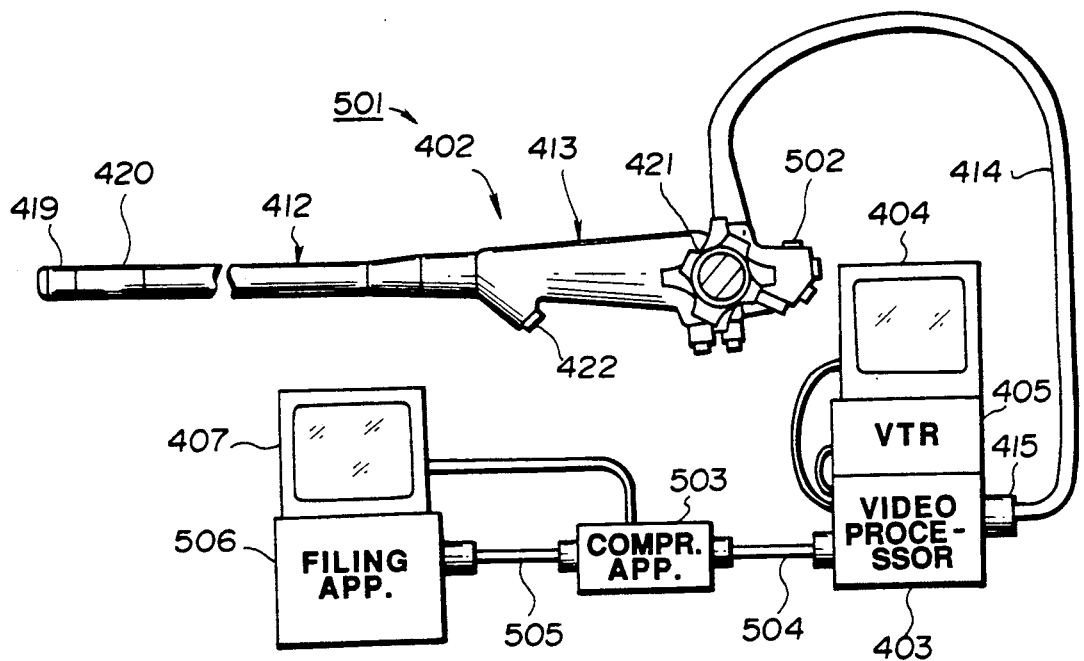
Figure 47:
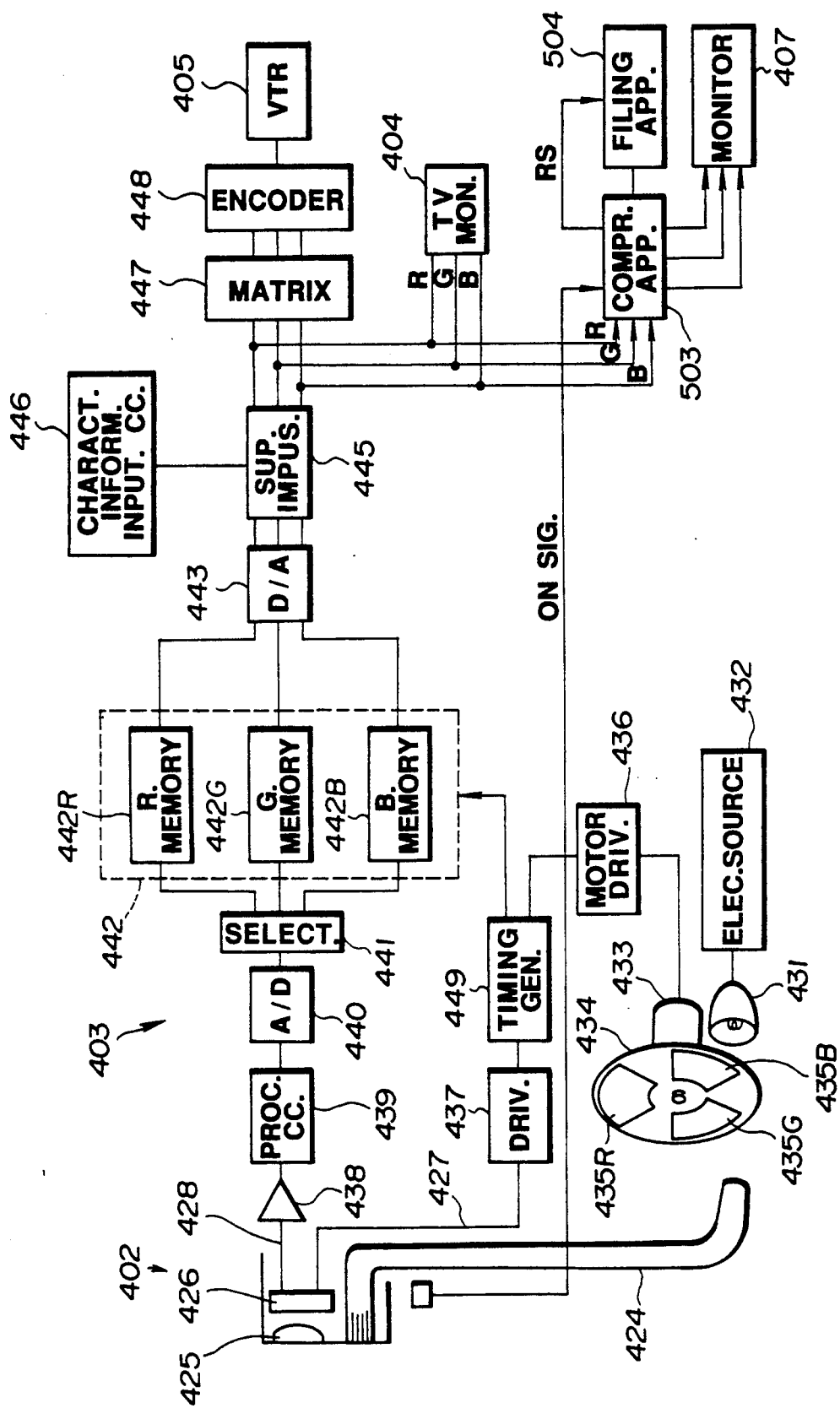

Next, FIG. 46 shows the entire configuration of an endoscope image recording system 501 according to a sixteenth embodiment in which the compressing operation is effected by actuating a release switch, and FIG. 47 shows the internal configuration thereof.

An appearance of the endoscope image recording system 501 shown in FIG. 46 is different from the endoscope system 401 shown in FIG. 38 in that a release switch 502 is provided on the operating section 413 of the electronic endoscope 402.

Furthermore, the video processor 403 is connected to a compression apparatus 503 through a cable 504, and the compression apparatus 503 is connected to both a filing apparatus 506 through a cable 505 and the monitor 407.

Upon the release switch 502 being actuated to turn on, a release-on signal is issued and transmitted to the compression apparatus 503 through the universal cord 414, the video processor 403 and the cable 504.

As shown in FIG. 47, the RGB output signals are applied to the compression apparatus 503 from the video processor 403. In response to the release-on signal, the compression apparatus 403 stores the RGB output signals into its internal memories and starts the compressing operation of the RGB output signals. After the compressing operation, a recording start signal RS is delivered to the filing apparatus 504. In response to this recording start signal RS, the filing apparatus 504 records the compressed image information from the compression apparatus 503.

Moreover, the monitor 407 doubles to display the images compressed by the compression apparatus 503, and to display the images resulted from expanding the compressed image information stored in the filing apparatus 504 by the compression apparatus 503.

The electronic endoscope 402 and the video processor 403 have the same internal configuration as that shown in FIG. 40.

Note that the internal configuration of the endoscope system 501, e.g., the configuration of the video processor 403, is not limited to that shown in FIG. 47 and may have the configuration of the observation apparatus 3 shown in FIG. 3, or the like.

It is apparent the many embodiments of the present invention varying over a wide range can be constituted based on the foregoing disclosure without departing from the spirit and scope of the invention. The present invention will be limited by only the attached claims and will not be restricted by specific embodiments of the invention.

What is claimed is:

1. An endoscope image compressing apparatus for receiving an endoscope image, compressing the endoscope image and outputting the compressed image, comprising:
    means for receiving the endoscope image while separating same into a plurality of color components,
    means for performing inter-image compression for each of said plural color components by making use of correlation between the images, and
    means for further performing intra-image compression by making use of correlation between said plural color components substantially at the same position in each picture,
    said inter-image compression means and said intra-image compression means being provided in series.

2. An endoscope image compressing apparatus according to claim 1, wherein said inter-image compression means is forecast coding means and said intra-image compression means is differential calculating means.

3. An endoscope image compressing apparatus according to claim 2, wherein said receiving means receives color signals in red (R), green (G) and blue (B) to first introduce said color signals to said inter-image compression means, then said inter-image compression means introduces the compressed R, G, B signals to said intra-image compression means, and thereafter said intra-image compression means obtains signals representing a differential between G and R, a differential between G and B, as well as G.

4. An endoscope image compressing apparatus according to claim 2, wherein said receiving means receives color signals in red (R), green (G) and blue (B) to first introduce said color signals to said intra-image compression means, then said intra-image compression means obtains signals representing a differential between G and R, a differential between G and B, as well as G and introduces these signals to said inter-image compression means, and thereafter said inter-image compression means compresses said signals representing a differential between G and R, a differential between G and B, as well as G.

5. An endoscope image recording system according to claim 4, wherein said image sensing means divides the image from said observing optical system of said endoscope and outputs the image into a plurality of color signals.

6. An endoscope image recording system according to claim 5, wherein said compression means changes a compression ratio dependent on said plurality of color signal.

7. An endoscope image recording system according to claim 6, wherein said plurality of color signals are three primary color signals, and a color signal among said plurality of color signals corresponding to a longest wavelength is compressed at a compression ratio higher than that for other color signals.

8. An endoscope image recording system according to claim 7, wherein said compression means sets a number of gradations used for quantization at a minimum for the color signal corresponding to the longest wavelength.

9. An endoscope image recording system according to claim 8, wherein said compression means has selection means to change the number of said gradations.

10. An endoscope image recording system according to claim 7, wherein said compression means sets an amount of thinning-out at a maximum for the color signal corresponding to the longest wavelength.

11. An endoscope image recording system according to claim 7, wherein said compression means sets an amount of band limiting at a maximum for the color signal corresponding to the longest wavelength.

12. An endoscope image recording system according to claim 7, wherein said compression means has smoothing means and sets a smoothing factor of said smoothing means at a maximum for the color signal corresponding to the longest wavelength.

13. An endoscope image recording system according to claim 7, wherein when a plurality of pixels are set as one block and an image is compressed in units each including a number of pixels less than that contained in one block, said compression means sets a number of pixels in one block at a maximum for the color signal corresponding to the longest wavelength.

14. An endoscope image recording system according to claim 7, wherein said color signals have wavelength regions of red (R), blue (B) and green (G), and the compression ratios are set to become larger in this order.

15. An endoscope image recording system according to claim 4, wherein said system further comprises retrieving means for retrieving the recorded endoscope image information from said recording means.

16. An endoscope image recording system according to claim 5, wherein said compression means includes first compression means for carrying out intra-image compression by making use correlation between said plural color signals in the image, and second compression means for carrying out inter-image compression for each of said color signals by making use of correlation between the images, said first and second compression means being operated in succession.

17. An endoscope image recording system according to claim 16, wherein said color signals have wavelength regions of red (R), green (G) and blue (B), and said first compression means takes differentials between R and G and between B and G.

18. An endoscope image recording system according to claim 16, wherein said compression means operates said first compression means and then said second compression means in succession.

19. An endoscope image recording system according to claim 16, wherein said compression means operates said second compression means and then said first compression means in succession.

20. An endoscope image recording system according to claim 5, wherein said compression means compresses said color signals by using an average value of the endoscope image as a reference.

21. An endoscope image recording system according to claim 20, wherein said compression means includes means for determining an average color from said color signals.

22. An endoscope image recording system according to claim 20, wherein said compression means stores an initial average color value of the endoscope image.

23. An endoscope image recording system according to claim 20, wherein said compression means includes means for determining at least one of differences and ratios between said color signals and said average color value.

24. An endoscope image recording system according to claim 23, wherein said compression means determines at least one of differences and ratios between said color signals and said average color value, and then quantizes said color signals with gradations different for each of said color signals.

25. An endoscope image recording system according to claim 20, wherein said compression means includes abnormal value correcting means for correcting those ones of the compressed signals, which exceed a data range recordable by said recording means, to be kept within said data range.

26. An endoscope image recording system according to claim 5, wherein said compression means includes conversion means for obtaining image data from said color signals based on a density of a colorant, and compresses said image data.

27. An endoscope image recording system according to claim 26, wherein said conversion means comprises first calculating means for obtaining transmissivity of hemoglobin and second calculating means for obtaining an intensity of illumination light, said compression means compresses said transmissivity of hemoglobin through forecast coding and compresses said intensity of illumination light through discrete cosine transform.

28. An endoscope image recording system according to claim 26, wherein said conversion means log-converts R, G, B signals as said color signals by using a look-up table, and said compression means divides the log-converted R, B signals by the log-converted G signal, compresses resultant quotients through discrete cosine transform, and also compresses a non-converted G signal through forecast coding.

29. An endoscope image compressing apparatus for receiving an endoscope image, compressing the endoscope image and outputting the compressed image, comprising:
   means for receiving the endoscope image while separating the endoscope image into three primary colors; and
   at least three compression means for compressing image signals associated with said three primary colors, wherein the compression means includes at least two compression means for compressing the image signals associated with two of said three primary colors, respectively, and long wavelength compression means for compressing the image signal associated with the remaining color of the longest wavelength at a compression ratio higher than compression ratios of said two compression means, wherein said long wavelength compression means, which includes smoothing means, sets a smoothing factor of said smoothing means at a maximum for an image signal corresponding to a longest wavelength.

30. An endoscope image compressing apparatus according to claim 29, wherein said three compression means are operated upon receiving a release signal from an endoscope apparatus.

31. An endoscope image compressing apparatus according to claim 29, wherein said long wavelength compression means sets a number of gradations used for quantization at a minimum for an image signal corresponding to a longest wavelength.

32. An endoscope image compressing apparatus according to claim 31, wherein said long wavelength compression means has selection means to change a number of said gradations.

33. An endoscope image compressing apparatus according to claim 29, wherein said long wavelength compression means sets an amount of thinning-out at a maximum for an image signal corresponding to a longest wavelength.

34. An endoscope image compressing apparatus according to claim 29, wherein said long wavelength compression means sets an amount of band limiting at a maximum for an image signal corresponding to a longest wavelength. has smoothing means and sets a smoothing factor of said smoothing means at a maximum for an image signal corresponding to a longest wavelength.

35. An endoscope image compressing apparatus according to claim 29, wherein when a plurality of pixels are set as one block and an image is compressed in units each including a number of pixels less than that contained in one block, said long wavelength compression means sets a number of pixels in one block at a maximum for an image signal corresponding to a longest wavelength.

36. An endoscope image recording system, comprising:

an endoscope having an observing optical system at the distal end of an insert section;

image sensing means for converting an image from said observing optical system of said endoscope to an electric signal;

compression means for receiving an image information signal from said image sensing means and for compressing said image information signal;

digital recording means for recording said image information signal compressed by said compression means; and release operation means for generating a trigger signal to produce a still picture, said release operation means is operatively connected to said compression means, wherein said compression means compresses the image from said image sensing means in response to said trigger signal and outputs the compressed image to said digital recording means.

* * * * *